(12) United States Patent
Sonderegger et al.

(10) Patent No.: US 7,897,364 B2
(45) Date of Patent: Mar. 1, 2011

(54) METHOD FOR DETERMINING INHIBITORS OF NEUROTRYPSIN

(75) Inventors: Peter Sonderegger, Zürich (CH); Stefan Hettwer, Zürich (CH); Marc F. Bolliger, Brittnau (CH); Birgit Dreier, Adlikon (CH); Beat Kunz, Winterthur (CH); Daniel Lüscher, Holziken (CH); Raymond Reif, Zürich (CH); Susanne Sales, Zürich (CH)

(73) Assignee: University of Zurich, Zurich (CH)

( * ) Notice: Subject to any disclaimer, the term of this patent is extended or adjusted under 35 U.S.C. 154(b) by 634 days.

(21) Appl. No.: 11/887,136

(22) PCT Filed: Mar. 29, 2006

(86) PCT No.: PCT/EP2006/061152
§ 371 (c)(1), (2), (4) Date: Oct. 19, 2007

(87) PCT Pub. No.: WO2006/103261
PCT Pub. Date: Oct. 5, 2006

(65) Prior Publication Data
US 2009/0170950 A1     Jul. 2, 2009

(30) Foreign Application Priority Data
Mar. 30, 2005 (EP) .................. 05102481

(51) Int. Cl.
*C12Q 1/37* (2006.01)
(52) U.S. Cl. .......................... 435/23; 435/18
(58) Field of Classification Search ......... None
See application file for complete search history.

(56) References Cited

U.S. PATENT DOCUMENTS 6,783,949 B1   8/2004   Muller et al.

FOREIGN PATENT DOCUMENTS

WO   98/49322   11/1998
WO   2004/035810   4/2004

OTHER PUBLICATIONS

Molinari F. et al. Truncating neurotrypsin mutation in autosomal recessive nonsyndromic mental retardation, Science, 29th Nov. 2002, vol. 298, pp. 1779-1781.*

Tseng C-N et al. Calcium plays a critical role in determining the AChR-clustering activities of alternatively spliced isoforms of agrin, JBC Papers in Press, Published on Mar. 5, 2003 as Manuscript M300282200, pp. 1-27 and figures 1-9.*

Reif R. et al. Specific cleavage of agrin by neurotrypsin, a synaptic protease linked to mental retardation, FASEB Journal, Research Communication, Published online Jun. 22, 2007, pp. 1-11.*

International Search Report issued in the International (PCT) Application of which the present application is the U.S. National Stage, mailed on Dec. 22, 2006.

* cited by examiner

*Primary Examiner*—Jon P Weber
*Assistant Examiner*—Satyendra K Singh
(74) *Attorney, Agent, or Firm*—Wenderoth, Lind & Ponack, L.L.P.

(57) ABSTRACT

The invention relates to a method for determining whether a compound is a neurotrypsin inhibitor, characterized in that the compound is incubated together with neurotrypsin, a variant thereof or a fragment comprising the protease domain and with a protein or peptide comprising agrin, a variant thereof or a fragment comprising the α- or the β-cleavage site of agrin, in an aqueous buffer solution, and the amount of cleavage of agrin is measured. Additionally, the invention relates to inhibitors of neurotrypsin found by this method, in particular to compounds of formula (1)

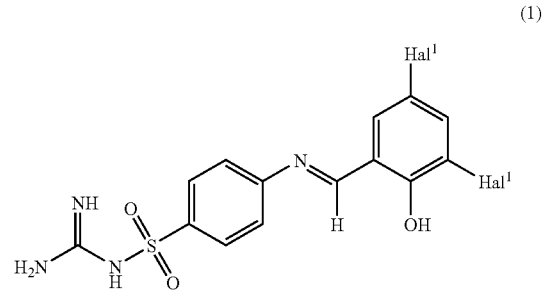

wherein $Hal^1$ and $Hal^2$ are fluorine, chlorine or bromine, and the use of such inhibitors for the treatment and/or prophylaxis of diseases caused by deficiency of synapses, for example skeletal muscle atrophy, schizophrenia, and cognitive disturbance.

11 Claims, 24 Drawing Sheets

A

B

METHOD FOR DETERMINING INHIBITORS OF NEUROTRYPSIN

This application is a U.S. national stage of International Application No. PCT/EP2006/061152 filed Mar. 29, 2006.

FIELD OF THE INVENTION

The invention relates to a method for determining whether a compound is a neurotrypsin inhibitor, to particular inhibitors of neurotrypsin, to the use of such inhibitors for the treatment and/or prophylaxis of skeletal muscle atrophy and schizophrenia, and the use as cognitive enhancers.

BACKGROUND OF THE INVENTION

Serine proteases belong to the group of proteolytic enzymes that have an intensively studied catalytic mechanism in common. Serine proteases are found in viruses, bacteria and eucaryotes. They include exopeptidases, endopeptidases and oligopeptidases. There are similarities in the reaction mechanism for several of the peptidases with different evolutionary origins. The geometric orientation of the catalytic residues is closely similar, despite the fact that otherwise the protein folds are quite different. A catalytic triad of serine, histidine and aspartate residues in the active site is responsible for efficient hydrolytic cleavage of the peptide bond. Examples of serine proteases include thrombin, factor XIIa, factor IXa, factor Xa, plasmin, tPA, trypsin, chymotrypsin and further proteins like urokinase, tryptase, elastase, kallikrein, complement C, protease A, serine carboxypeptidase II. They are involved in a variety of important processes like, for example, blood coagulation and food digestion. It has been shown that serine protease inhibitors inhibit cellular processes, such as adhesion, migration, free radical production and apoptosis. Intravenously administered serine protease inhibitors provide a protective effect against tissue damage. Small molecule inhibitors have been shown to have a high potential in treatment of different diseases related to hematology, oncology, asthma, inflammation, neurology, pulmonary medicine and immunology. Appropriate serine protease inhibitors may be useful in treatment of disfunctions in the field of thrombotic diseases, asthma, cirrhosis, arthritis, carcinoma, melanoma, restenosis, atheroma, trauma, shock and reperfusion injury.

The investigated enzyme neurotrypsin (WO 98/49322) belongs to the chymotrypsin family, whose members are almost entirely confined to animals. The amino acid sequence of neurotrypsin defines a mosaic protein of 875 amino acids consisting of a Kringle domain, followed by four scavenger receptor cysteine-rich repeats (three in the mouse), and the serine protease domain (FIGS. 1, A and B). Neurotrypsin contains, like thrombin, tPA, trypsin and some other enzymes, an aspartate residue in the bottom of its S1 pocket, therefore showing specificity for basic amino acids at this binding site. The structural similarity of neurotrypsin to the proteases of the blood coagulation cascade and the fibrinolytic system, such as factor X, factor IX, thrombin, tissue plasminogen activator, and plasmin suggests that it may be an element of a protease-driven extracellular signaling mechanism in the nervous system. (Gschwend, T. P., et al., Molec. Cell Neurosci. 9: 207-219, 1997; Proba, K., et al., Biochim. Biophys. Acta 1396: 143-147, 1998).

As will be shown hereinbelow, neurotrypsin is located at the presynaptic nerve terminal of synapses of the central nervous system (CNS) and at the neuromuscular junction (NMJ). The synapse is the connection between nerve cells (neurons) where messages are communicated in the form of chemical substances, termed neurotransmitters. The synapse is composed of a presynaptic terminal formed by the signal-emitting cell and the postsynaptic specialization of the signal-receiving cell. Neurotransmitters released from the presynaptic terminal cross the synaptic cleft and bind to the neurotransmitter receptors in the postsynaptic specialization. Upon binding of the neurotransmitter the receptor induces the generation of an electrical pulse in the postsynaptic cell. Signal transmission between two neurons is the basis of neuronal function. Brain functions are the result of the specific assembly of an enormous number of neurons to information-processing networks.

The majority of synapses is found in the central nervous system (CNS, brain), where every synapse connects two neurons. By such bilateral point-to-point connections, every neuron may connect to thousands of other neurons. However, synapses also connect a neuron to a gland or a muscle cell. The neuromuscular junction (NMJ, muscle end-plate) is the synapse that connects a nerve cell with a striated muscle cell. Synapses located outside of the brain, the brain stem and the spinal cord are termed peripheral nervous system (PNS) synapses. CNS synapses and PNS synapses exhibit many structural and functional commonalities and share many of their molecular components (synaptic molecules). Therefore, synaptic target molecules may be useful for targeting synaptic functions of both the CNS and the PNS.

Skeletal muscle atrophy (sarcopenia), defined as the loss of muscle mass and strength, plays a major role in the pathogenesis of frailty and functional impairment that occurs with old age. It plays a major role in the loss of muscular strength, decreased metabolic rate, gradual reduction of bone density and decreased aerobic capacity (Doherty, T. J., J. Appl. Physiol. 95: 1717-1727, 2003). The loss of muscle mass manifests as a decrease in the cross-sectional area of the muscle with age, which has been determined to result from a combined effect of a reduction in both the number of muscle fibers and the thickness of the individual remaining fibers.

Over the past years, considerable progress has been made in the identification and characterization of factors contributing to the degradation of muscle mass. Important genes associated with these processes encode ubiquitin protein ligases that were found increased in atrophic muscle. Among the factors that have a hypertrophic activity and, as such, block atrophy, insulin-like growth factor 1 (IGF-1) has been found to play an essential role. This and several other regulatory pathways controlling skeletal muscle mass have been investigated intensively (for a review see: Glass, D. J., Nature Cell Biol. 5: 87-90, 2003). In spite of important progress in both the characterization of the molecular mechanisms that control muscle degradation leading to atrophy and the hypertrophic effects of insulin-like growth factor, and in spite of the fact that several companies work on the development of drugs capable of stimulating the increase of muscle mass, no drugs have been approved up to now.

A morphological hallmark of the skeletal muscle atrophy found at old age (sarcopenia) is a considerable reduction of the number of muscle fibers. Ample evidence from numerous independent studies supports that neural input to a fraction of the muscle fibers is disrupted with age, resulting in subsequent atrophy and eventually the disappearance of the denervated fibers (Kamal, H. K., Nutrition Reviews 61: 157-167, 2003). Another characteristic feature of the skeletal muscle atrophy found at old age is a coincidence of the muscular atrophy with a considerable reduction of the number of motoneurons (Welle, S., Can. J. Appl. Physiol. 27: 19-41, 2002) and a marked structural alteration of the neuromuscular junction (Tapia, J. C. et al., Abstract Viewer/Itinerary Planner, Washington D.C.: Society for Neuroscience). These characteristics indicate that a significant age-related deterioration of the structure and the function of the neuromuscular junction is a major contributing factor to a process that ultimately results in a structural and functional denervation. Denervated muscle fibers that do not receive compensatory reinnervation within weeks become progressively atrophic and eventually disappear.

Schizophrenia is a chronic, severe, and disabling brain disease. Approximately 1% of the world population develops schizophrenia during their lifetime. Individuals who develop schizophrenia experience severe suffering. Approximately 10% commit suicide. Although schizophrenia affects men and women with equal frequency, the disorder often appears earlier in men, usually in the late teens or early twenties, than in women, who are generally affected in the twenties to early thirties. People with schizophrenia often suffer terrifying symptoms such as hearing internal voices not heard by others, or believing that other people are reading their minds, controlling their thoughts, or plotting to harm them. These symptoms may leave them fearful and withdrawn. Their speech and behavior can be so disorganized that they may be incomprehensible or frightening to others. The currently available treatments of schizophrenia reduce suffering considerably, but approximately ⅔ of the people affected by schizophrenia require public assistance within a few years after onset. The majority of them are unable to return to work or school and have relatively little or no social interactions, and most people with schizophrenia continue to suffer some symptoms throughout their lives. It has been estimated that no more than one in five individuals recovers completely. Therefore schizophrenia is one of the most important public health problems world-wide, and the costs to society are counted in billions of dollars.

The currently most consistent neuropathological finding in brains of schizophrenic patients is a reduction of the number of synapses in the gray matter of the central nervous system, which is reflected by a decrease in the volume of the neuropil (the synaptic area). No evidence for neuronal degeneration is observed. Typically, the number of neurons counted per area of tissue is rather increased, an observation explained by a selective decrease in the number of synapses in the neuropil area between the neurons while the number of neuronal cell somas remained constant. The phenomenon has been reported over the past two decades by several independent studies on post mortem material and has been found most extensive in the prefrontal cortex. The literature documenting this observation has been carefully reviewed by Selemon, L. D. and Goldman-Rakic, P. S. (Psychiatry 45: 17-25, 1999). McGlashan, T. H. and Hoffman, R. E. (Arch. Gen. Psychiatry 57: 637-648, 2000) summarized the essential morphological, developmental, electrophysiological, and metabolic observations in schizophrenia in the light of the "excessive synaptic pruning" hypothesis and came to the conclusion that "excessive synaptic pruning" or "developmentally reduced synaptic connectivity" is an increasingly attractive pathophysiological model of schizophrenia. Based on this model, schizophrenia arises from critically reduced synaptic connectedness as a result of developmental disturbances of synaptogenesis during gestation and early childhood and/or excessive synaptic pruning during adolescence. The model accounts for the phenomenology of the disorder, the symptomatic states, the onset, neurodevelopmental deficits, window of deterioration, sex differences in clinical presentation, course determined by age of onset, and preservation of the schizophrenic genotype in the population despite diminished phenotypic fecundity.

Cognitive enhancers are drugs aimed at preventing, improving, or treating cognitive deficits at both the clinical and subclinical level. Such drugs are beneficial for the treatment of memory difficulties of elderly people who have not progressed to Alzheimer's disease (mild cognitive impairment). However, such drugs are also beneficial for the improvement of cognitive functions in patients with the established diagnosis of Alzheimer's disease or other diseases associated with dementia or for the improvement of cognitive functions in posttraumatic cognitive dysfunction, as well as for the improvement of the age-related impairment of cognitive functions that are considered as a normal feature of the ageing process.

Mild cognitive impairment is a widely cited concept in clinical research on ageing-related cognitive disorders (Ritchie, K. and Touchon, J., The Lancet 355: 225-228, 2000). It refers generally to subclinical complaints of memory functioning in elderly people, which are judged to have a high probability of evolving towards Alzheimer's disease. The identification of people at potential risk for dementia with a view to early therapeutic intervention is important, because it may lessen distress for both patient and family, minimize the risk of accidents, prolong autonomy, and perhaps even ultimately prevent the onset of the process leading to dementia itself.

The impairment of cognitive functions without dementia is so common among elderly people that it is considered by many as an inevitable feature of the ageing process. Nonetheless, it has acquired clinical significance because of the difficulties patients may have with carrying out everyday activities. Although the range of impairments seen in populations without dementia is extremely broad, several clinical labels have been proposed to describe this tail-end of the normal cognitive range. One of the earliest was benign senescent forgetfulness. Its clinical features include an inability to recall minor detail, the forgetting of remote as opposed to recent events, and awareness of memory problems. The term ageing-associated cognitive decline refers to a wider range of cognitive functions (attention, memory, learning, thinking, language, and visuospatial function), and is diagnosed by reference to norms for elderly people. Prescription of cognitive enhancers may prolong the capacity of the affected individuals to carry out their daily activities and, thus, prolong their autonomy. Other disorders associated at least in part of the affected individuals with cognitive impairments that may eventually lead to dementia include Parkinson's disease, multiple sclerosis, stroke, and head trauma. The prescription of cognitive enhancer drugs may also improve cognitive functions in these patients.

SUMMARY OF THE INVENTION

The invention relates to a method for measuring the catalytic activity of neurotrypsin, characterized in that neurotrypsin, a variant thereof or a fragment comprising the protease domain of neurotrypsin and a protein or peptide comprising agrin, a variant thereof or a fragment comprising the α- or the β-cleavage site of agrin, are incubated together in an aqueous buffer solution, and the amount of cleavage of agrin is measured. Furthermore, the invention relates to a method for determining whether a compound is a neurotrypsin inhibitor, characterized in that the compound is incubated together with neurotrypsin, a variant thereof or a fragment comprising the protease domain of neurotrypsin and with a protein or peptide comprising agrin, a variant thereof or a fragment comprising the α- or the β-cleavage site of agrin, in an aqueous buffer solution, and the amount of cleavage of agrin is measured.

Additionally, the invention relates to inhibitors of neurotrypsin found by this method, in particular to compounds of formula

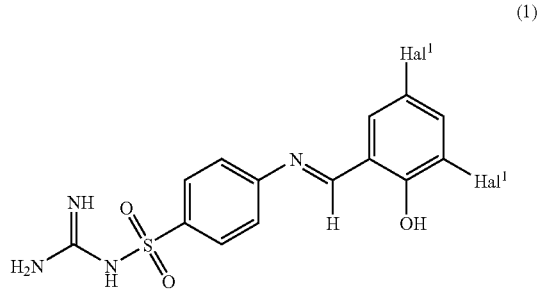

(1)

wherein Hal[1] and Hal[2] are, independently of each other, fluorine, chlorine or bromine; and pharmaceutically acceptable addition salts thereof.

The invention further relates to the use of such inhibitors as medicaments, in particular for the treatment and/or prophylaxis of diseases caused by deficiency of synapses, for example skeletal muscle atrophy, schizophrenia and cognitive disturbance, and to the use of such inhibitors for the manufacture of a medicament for the treatment and/or prophylaxis of skeletal muscle atrophy, schizophrenia and cognitive disturbance.

(A) hNt: human neurotrypsin.

(B) mNt: mouse neurotrypsin.

Neurotrypsin is composed of a proline-rich basic domain (PB), a kringle domain (KR), three (mNt) or four (hNt) scavenger receptor cysteine-rich domains (SRCR1, SRCR2, SRCR3, and SRCR4), and a protease domain (PROT).

Figure 2:
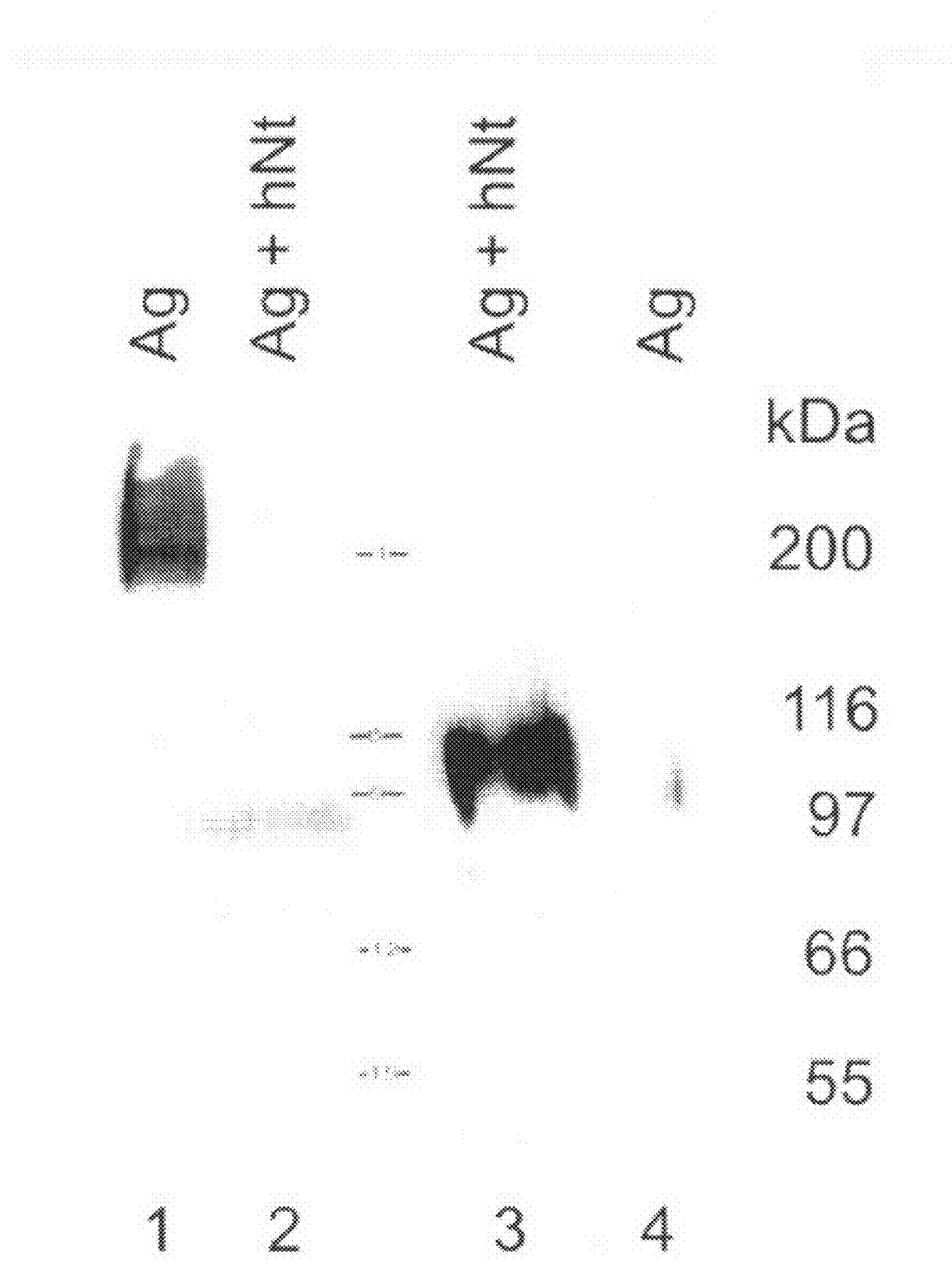

FIG. 2: Neurotrypsin-mediated cleavage of agrin: Western blot analysis of agrin from HEK293 cells cotransfected with agrin and neurotrypsin.

Semi-confluent HEK293T cells were transiently transfected with either pcDNA3.1-neurotrypsin or pcDNA3.1-agrin, or both. Samples were separated by SDS-PAGE. The membrane was incubated with a polyclonal anti-agrin antibody directed against the C-terminal moiety of agrin, followed by incubation with a secondary peroxidase-coupled antibody.

| (Lane 1, Ag) | Detergent extract of cells that are single-transfected with agrin. |
| (Lane 2, Ag + hNt) | Detergent extract of cells that are double-transfected with agrin and neurotrypsin. Note that agrin is strongly reduced. |
| (Lane 3, Ag + hNt) | Culture medium of cells that are double-transfected with agrin and neurotrypsin. A 100-kDa band is detected with the anti-agrin antibody directed against the C-terminal moiety of agrin. |
| (Lane 4, Ag) | Culture medium of cells that are single-transfected with agrin. |

The production of neurotrypsin under all conditions was confirmed after reprobing the blot with anti-neurotrypsin antibodies. Analysis of the culture medium revealed that the agrin immunoreactivity that was lost from the cell extract of the double transfected cells had been released into the supernatant medium. No signal was detected in the supernatant medium of HEK293T cells transfected with agrin and catalytically inactive neurotrypsin.

Figure 3:
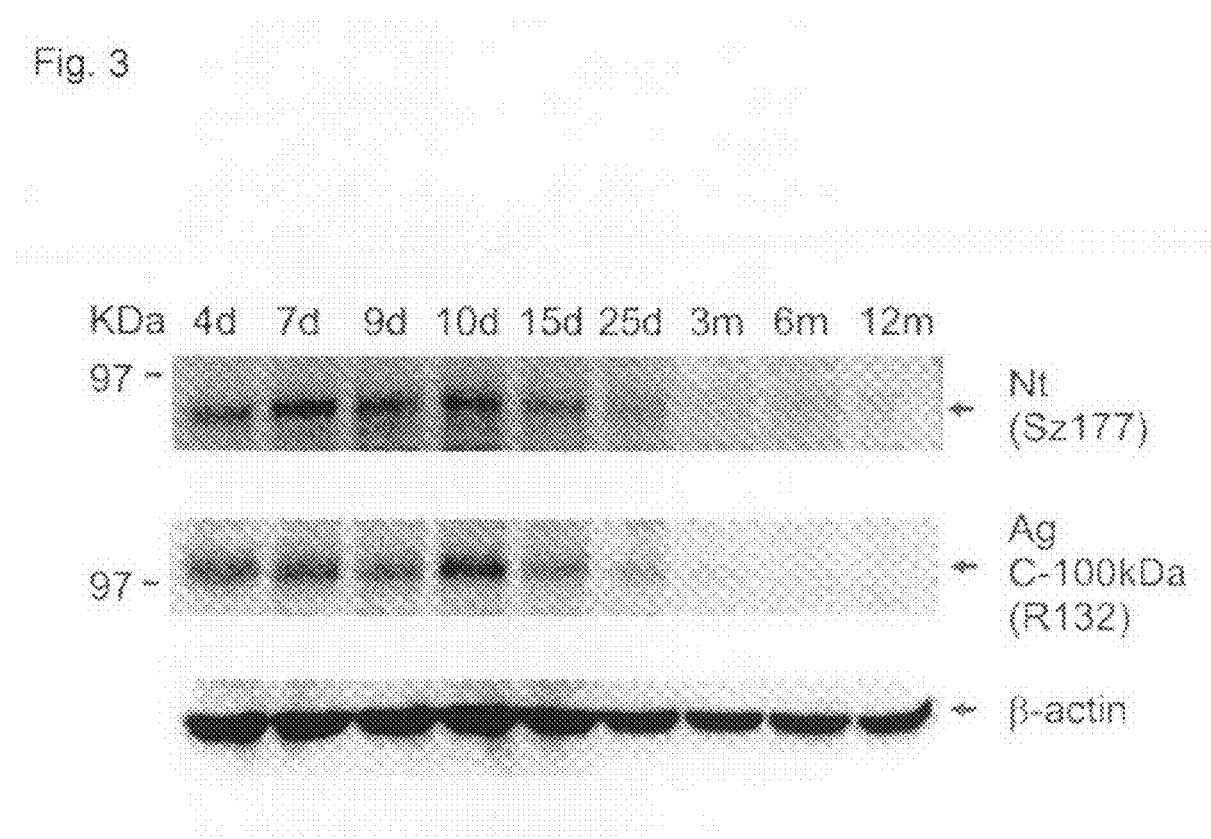

FIG. 3: The temporal pattern of agrin cleavage in vivo coincides with the temporal pattern of neurotrypsin expression.

Homogenates of spinal cords of mice of different ages were subjected to SDS-PAGE and Western blot analysis, and then probed for neurotrypsin and the C-terminal 100-kDa fragment of agrin, using the specific antibodies SZ 177 versus neurotrypsin and R132 versus the C-terminal 100-kDa fragment of agrin. β-actin was probed as a control for equal amounts of tissue homogenate in the different samples.

Figure 4:
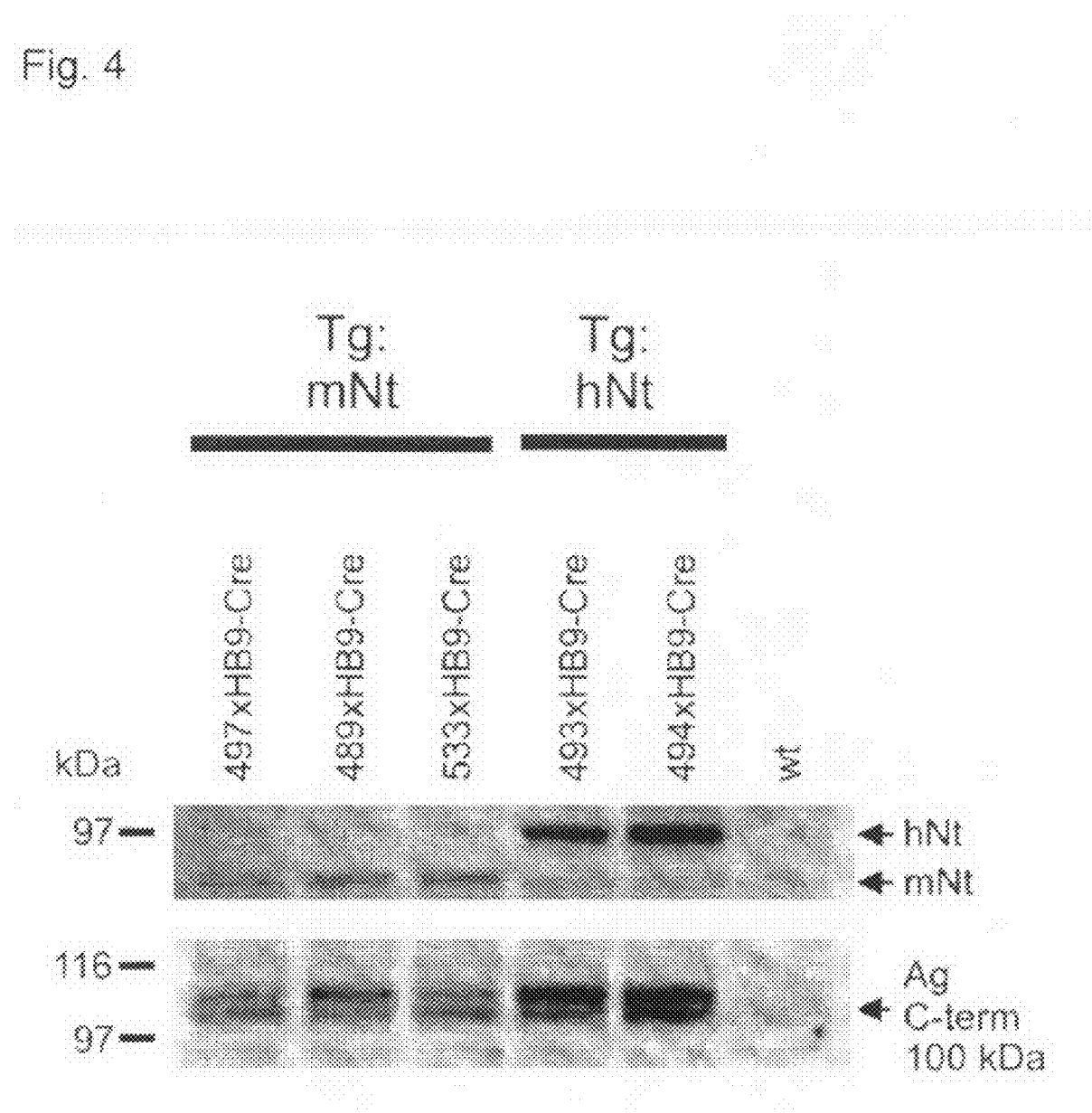

FIG. 4: Transgenic overexpression of neurotrypsin in motoneurons results in an increased cleavage of agrin.

Western blots of spinal cord extracts were probed with antibodies against human (hNt) and mouse (mNt) neurotrypsin as well as with antibodies against the C-terminal 100-kDa fragment of agrin. The results demonstrate an increased occurrence of the C-terminal 100-kDa fragment of agrin in the mice overexpressing neurotrypsin.

Figure 5:
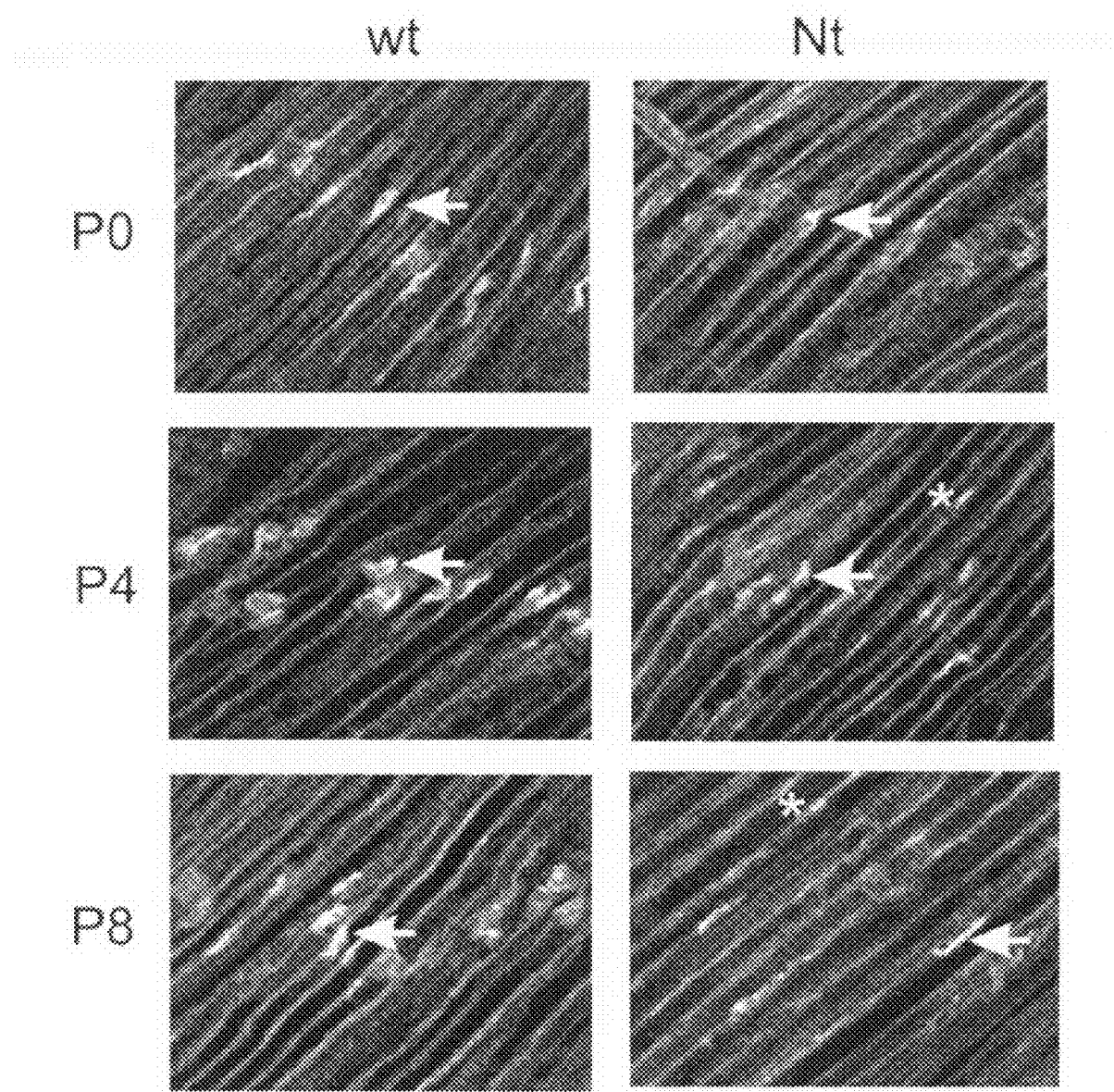

FIG. 5: Neurotrypsin removes agrin from the neuromuscular junction (NMJ).

NMJs of the diaphragm of mice immunostained for agrin at postnatal days 0 (P0), 4 (P4), and 8 (P8). In transgenic mice overexpressing neurotrypsin in motoneurons, agrin disappears from the NMJ within hours to days after the onset of overexpression. P4: transition state. Partial loss of agrin from the NMJs. Arrows point to individual well-formed NMJs. Asterisks indicate partially dispersed NMJs. P8: almost complete loss of agrin from the NMJs. Arrows point to individual well-formed NMJs. Asterisks indicate partially dispersed NMJs.

Figure 6:
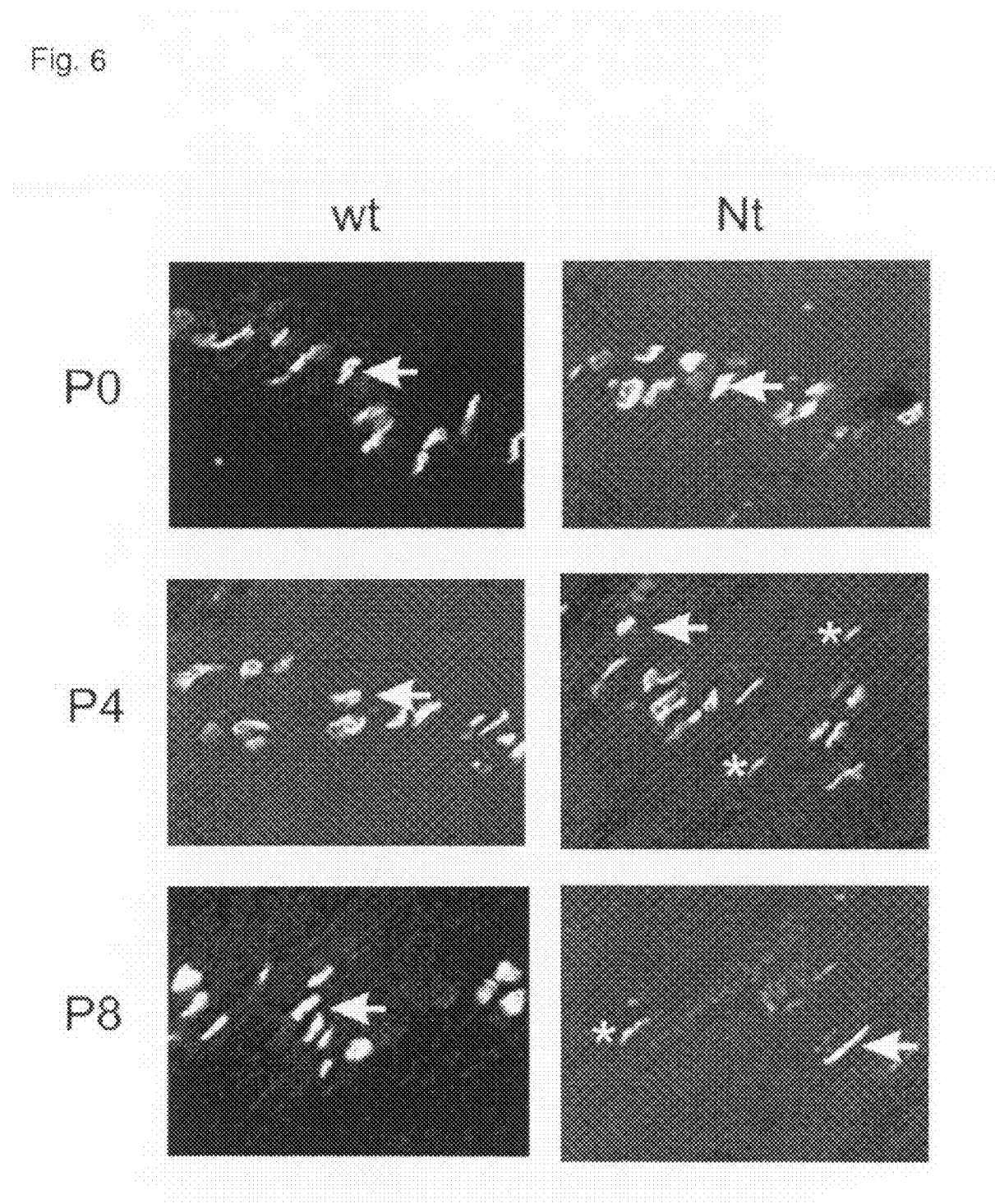

FIG. 6: Neurotrypsin-dependent removal of agrin from the NMJ is accompanied by dispersal of the postsynaptic apparatus.

Figure 7:
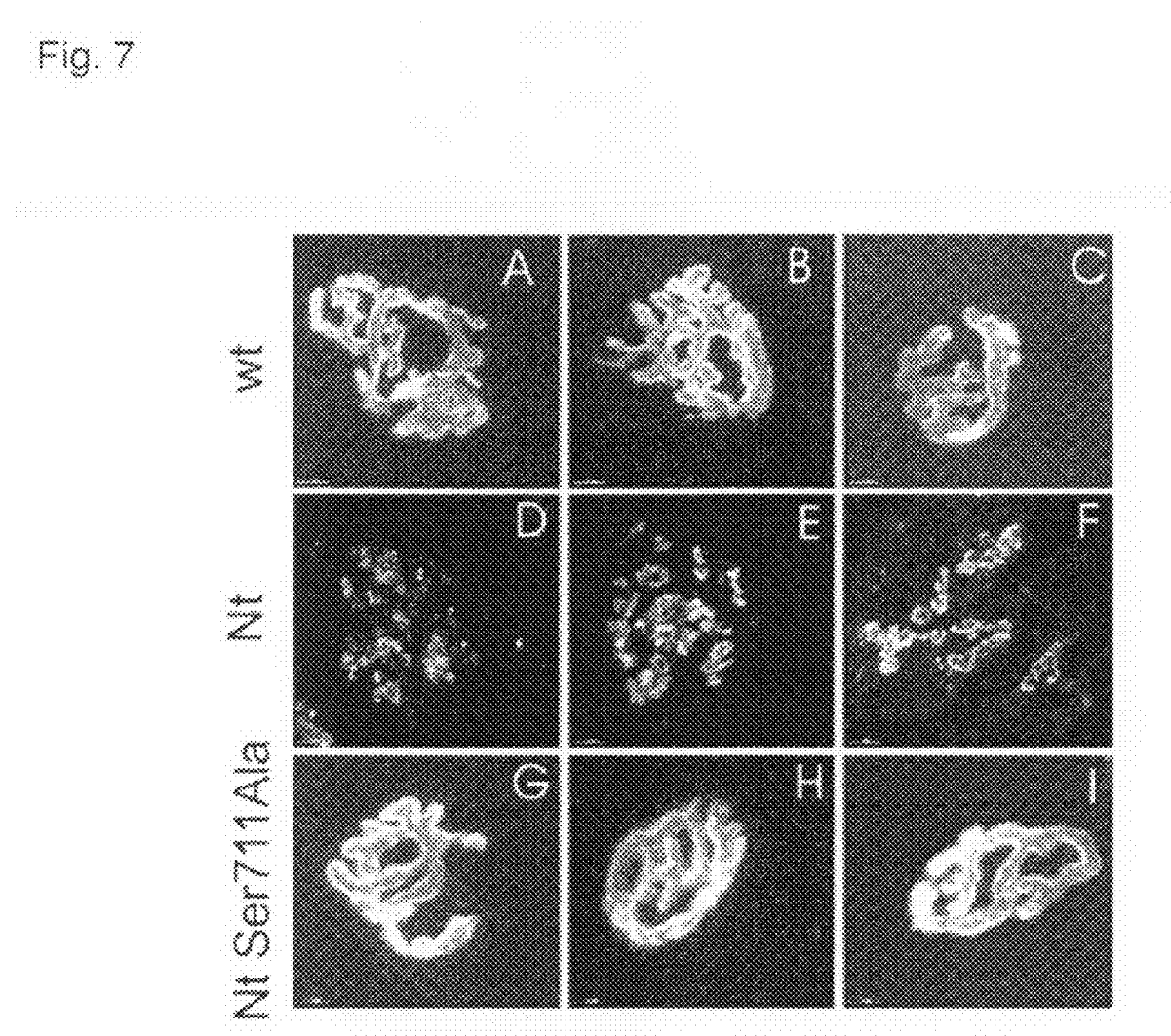

NMJs of the diaphragm of the same mice as in FIG. 7 stained for acetylcholine receptors with fluorescently labeled α-bungarotoxin (α-Btx). The acetylcholine receptors disappear within hours to days after the onset of overexpression. P4: transition state. Partial loss of NMJs. Arrows point to individual well-formed NMJs. Asterisks indicate partially dispersed NMJs. P8: almost complete loss of NMJs. Arrows point to individual well-formed NMJs. Asterisks indicate partially dispersed NMJs.

FIG. 7: Fragmentation of the NMJs in the soleus muscle of Nt-overexpressing mice. (A-C) α-Bungarotoxin (α-Btx) staining of NMJs of wild-type mice shows a typical Pretzel-like structure.

(D-F) α-Btx staining of NMJs of Nt-overexpressing mice shows a pronounced fragmentation of the postsynaptic apparatus.

(G-I) NMJs of transgenic mice overexpressing a catalytically inactive form of Nt (Neurotrypsin Ser711Ala) are unaltered.

Figure 8:
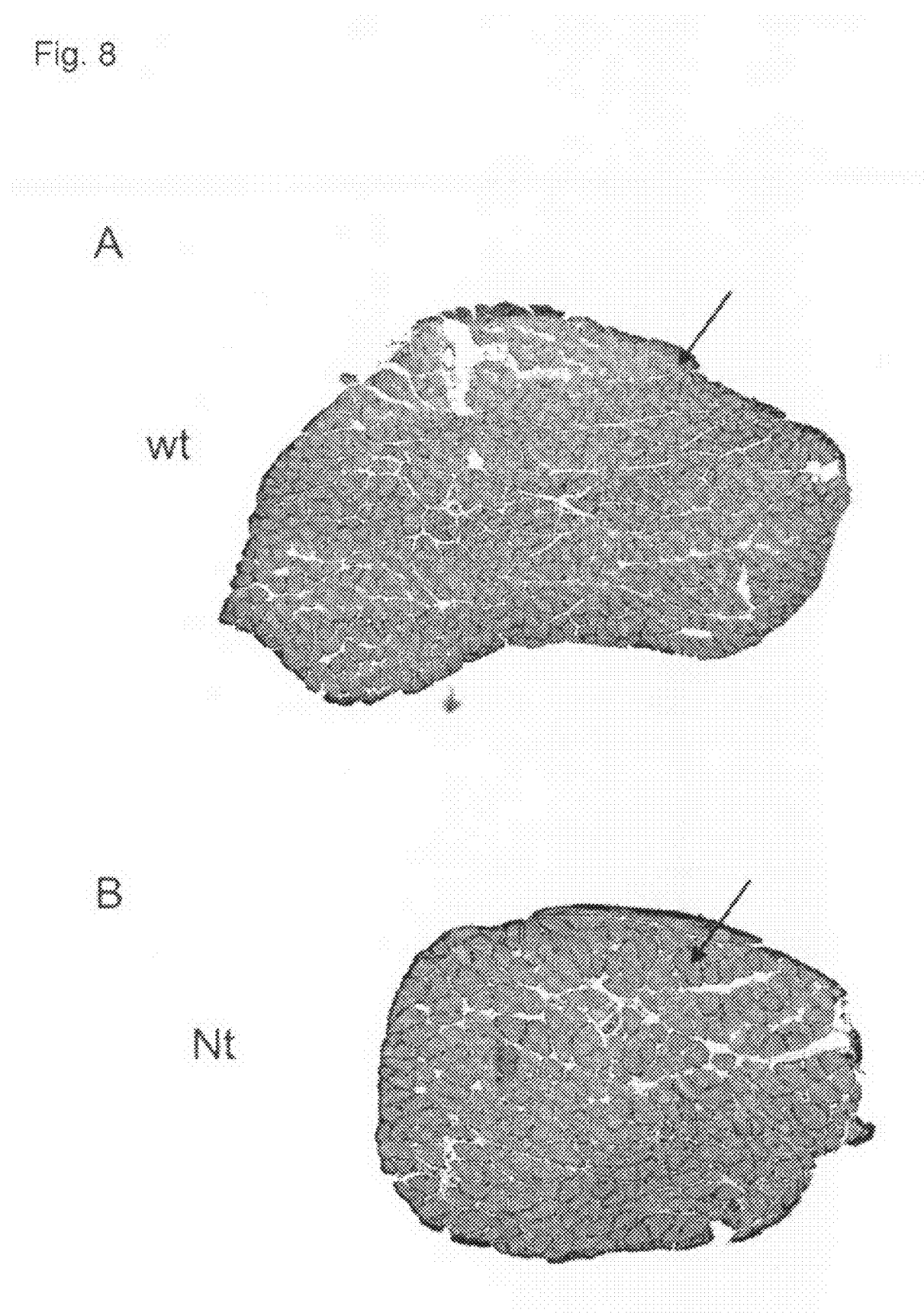

FIG. 8: Cross-sections through the soleus muscle of a wild-type and a neurotrypsin-overexpressing mouse.

(A) Wild-type mouse (B) Neurotrypsin-overexpressing mouse.

Compared to wild-type mice muscles of Nt-overexpressing mice contain fewer muscle fibers. Arrows in (A) and (B) point to a single muscle fiber.

Figure 9:
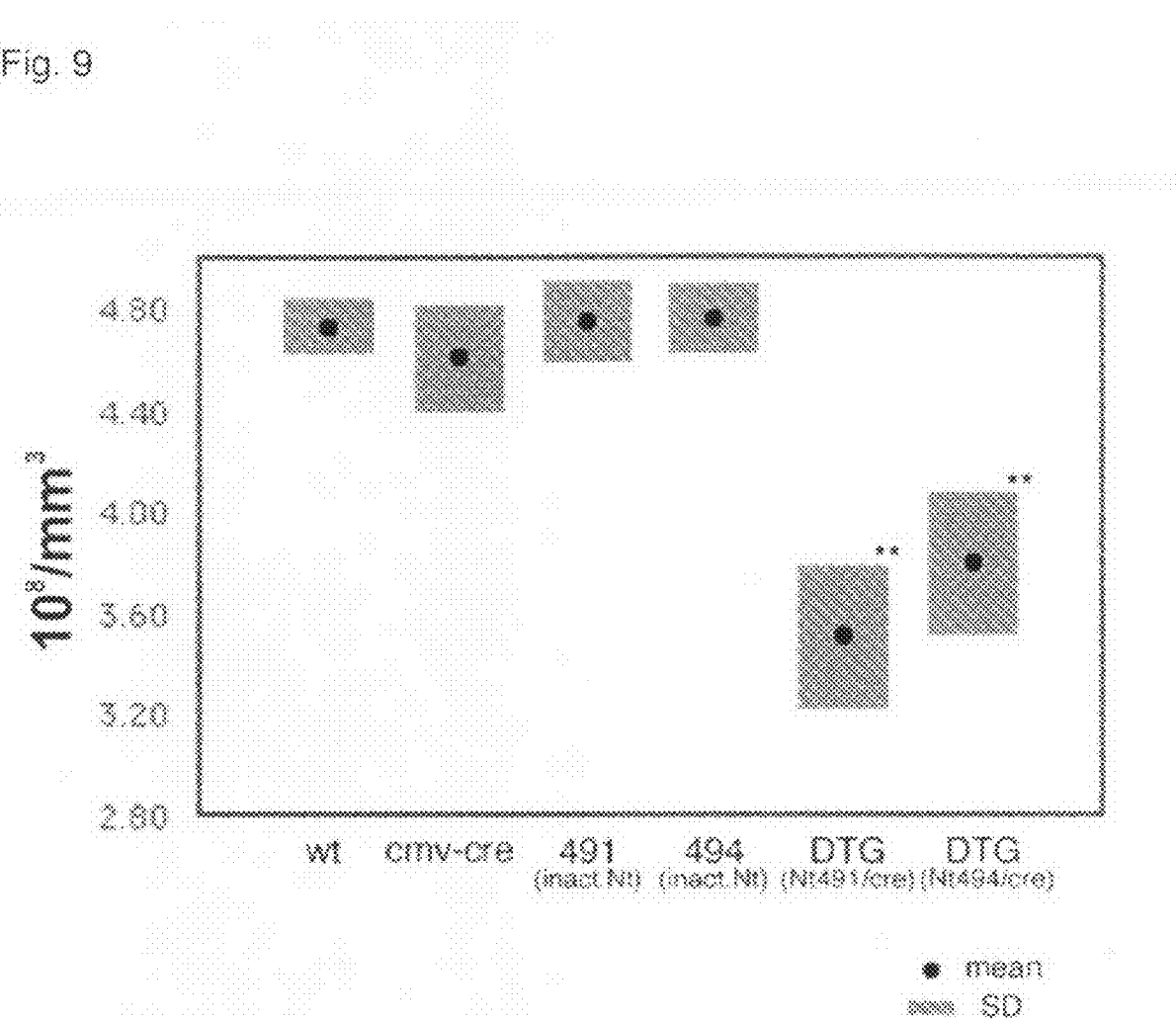

FIG. 9: Quantification of the number of synapses per volume of tissue in the neuropil of the stratum radiatum of the CA1 region of the hippocampus.

In all experimental animals, the number of synapses per volume of tissue was determined from electron-microscopic sections taken from the same location in the stratum radiatum of the CA1 region of the hippocampus.

| | |
|---|---|
| wt: | wild-type; |
| CMV-Cre: | transgenic line expressing the Cre recombinase under the control of the CMV promoter; |
| 491(inact. Nt): | transgenic line 491, bearing the inactive transgene, containing a transcriptional stop segment; |
| 494(inact. Nt): | transgenic line 494, bearing the inactive transgene, containing a transcriptional stop segment; |
| DTG(Nt491/cre): | double transgenic mouse derived from the line 491, in which the inactive neurotrypsin transgene has been activated by crossing in the Cre recombinase; |
| DTG(Nt494/cre): | double transgenic mouse derived from the line 494, in which the inactive neurotrypsin transgene has been activated by crossing in the Cre recombinase. |

** $p < 0.01$.

Figure 10:
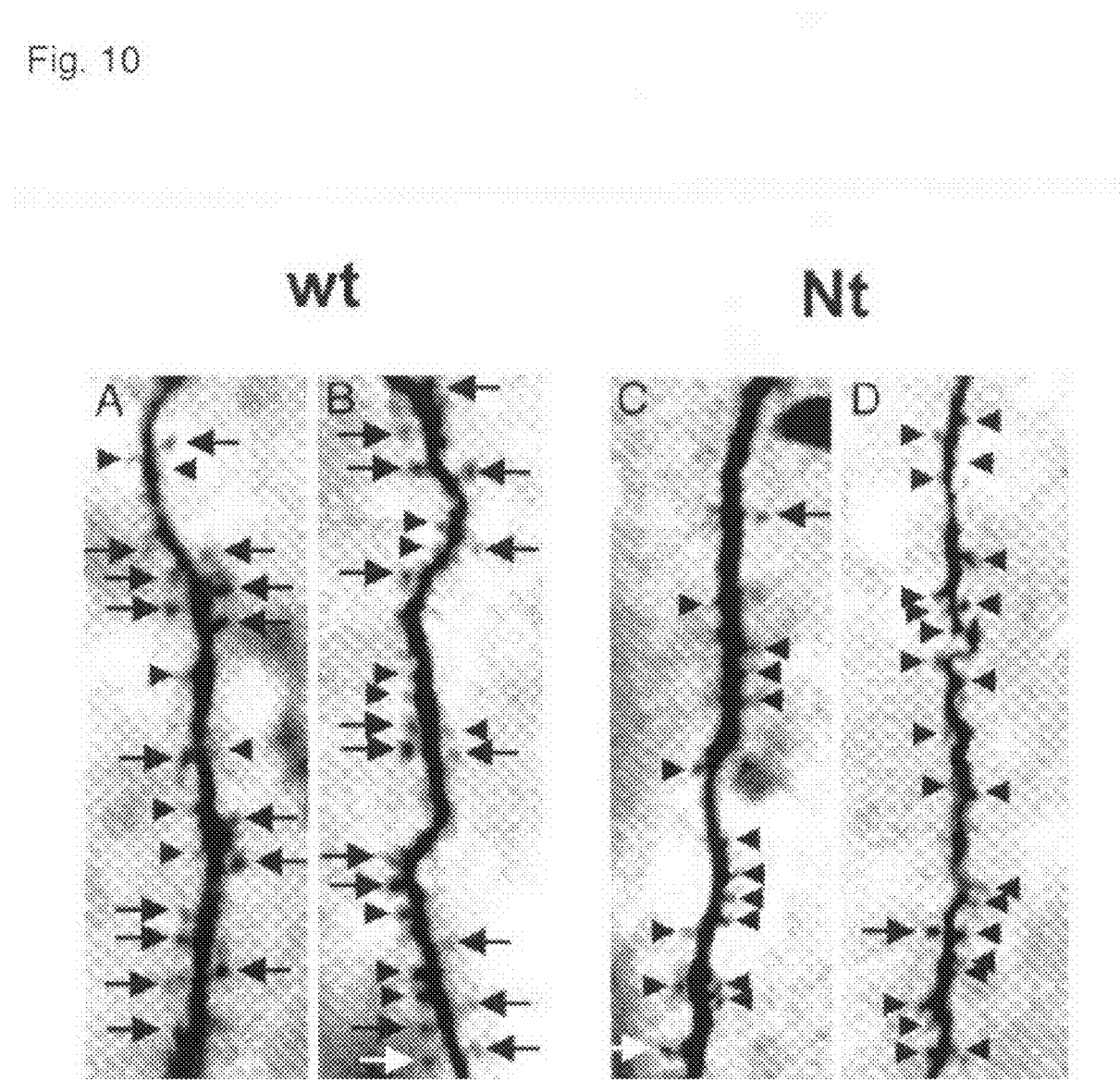

FIG. 10: Spines on secondary dendritic branches of CA1 pyramidal neurons. Spines on secondary dendritic branches of CA1 pyramidal neurons of wild-type mice (A and B) and double-transgenic mice overexpressing neurotrypsin (C and D). CA1 pyramidal cells were iontophoretically filled with biocytin during electrophysiological in vitro studies and visualized using avidin-biotin-peroxidase histochemistry. Dendrites of wild-type mice have many long, well-developed spines (large arrows); in addition, many short, stubby-shaped spines (small arrowheads) are also found. Dendrites of neurotrypsin-overexpressing mice (littermates) are dominated by short stubby-shaped spines (small arrowheads); long, well-developed spines (large arrows) are very rare. The total spine density (number of spines per unit length of dendrite) is markedly lower in neurotrypsin-overexpressing mice (C and D).

Figure 11:
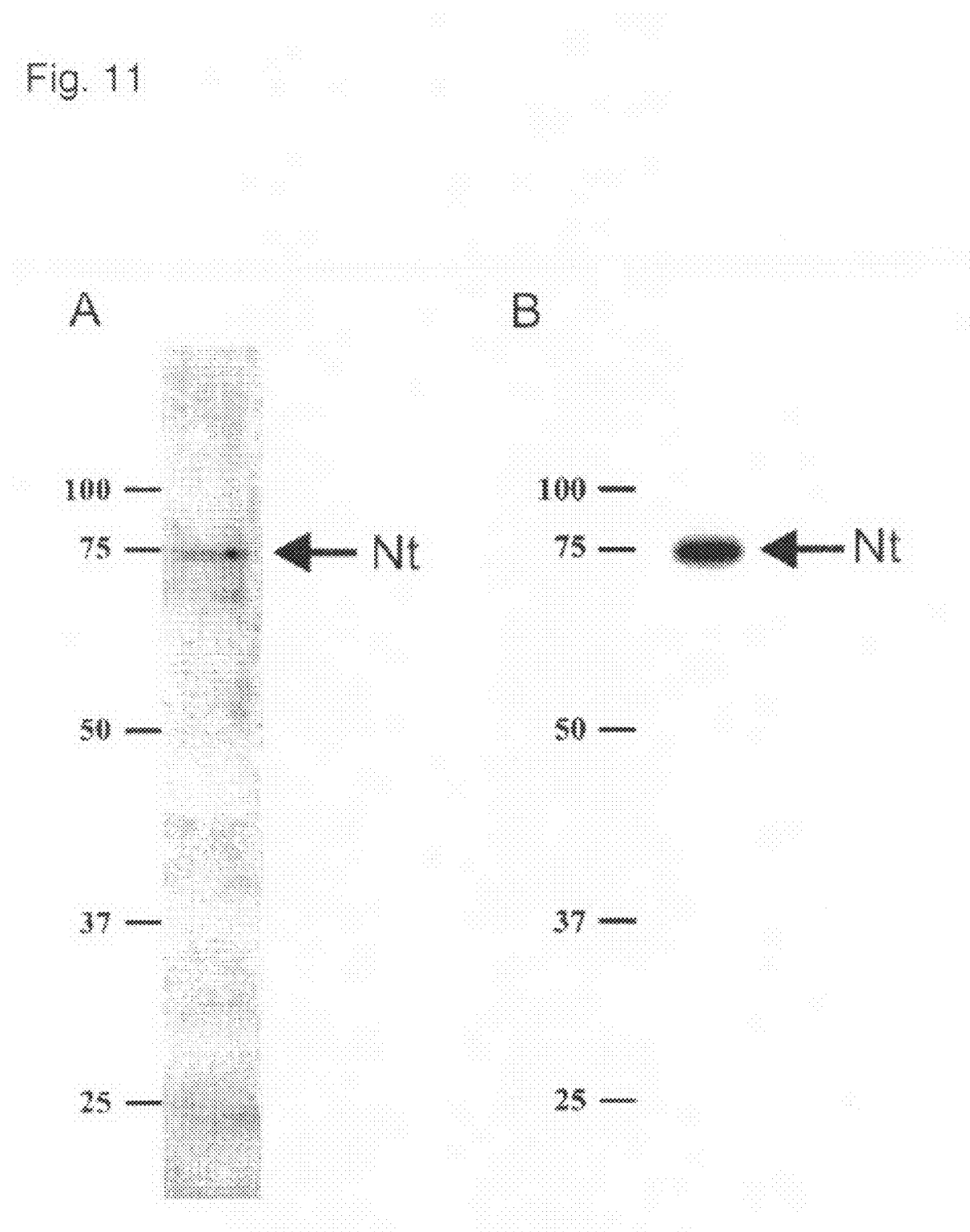

FIG. 11: Purified full-length human neurotrypsin.

SDS-PAGE followed by silver staining (A) and Western blotting (B) showed a single band of the full-length human neurotrypsin (indicated by arrows) migrating at a position corresponding to approximately 75 kDa under non-reducing conditions. Immunodetection (B) was performed using an anti-neurotrypsin antibody. Molecular masses of standards (kDa) are indicated in the left margins.

Figure 12:
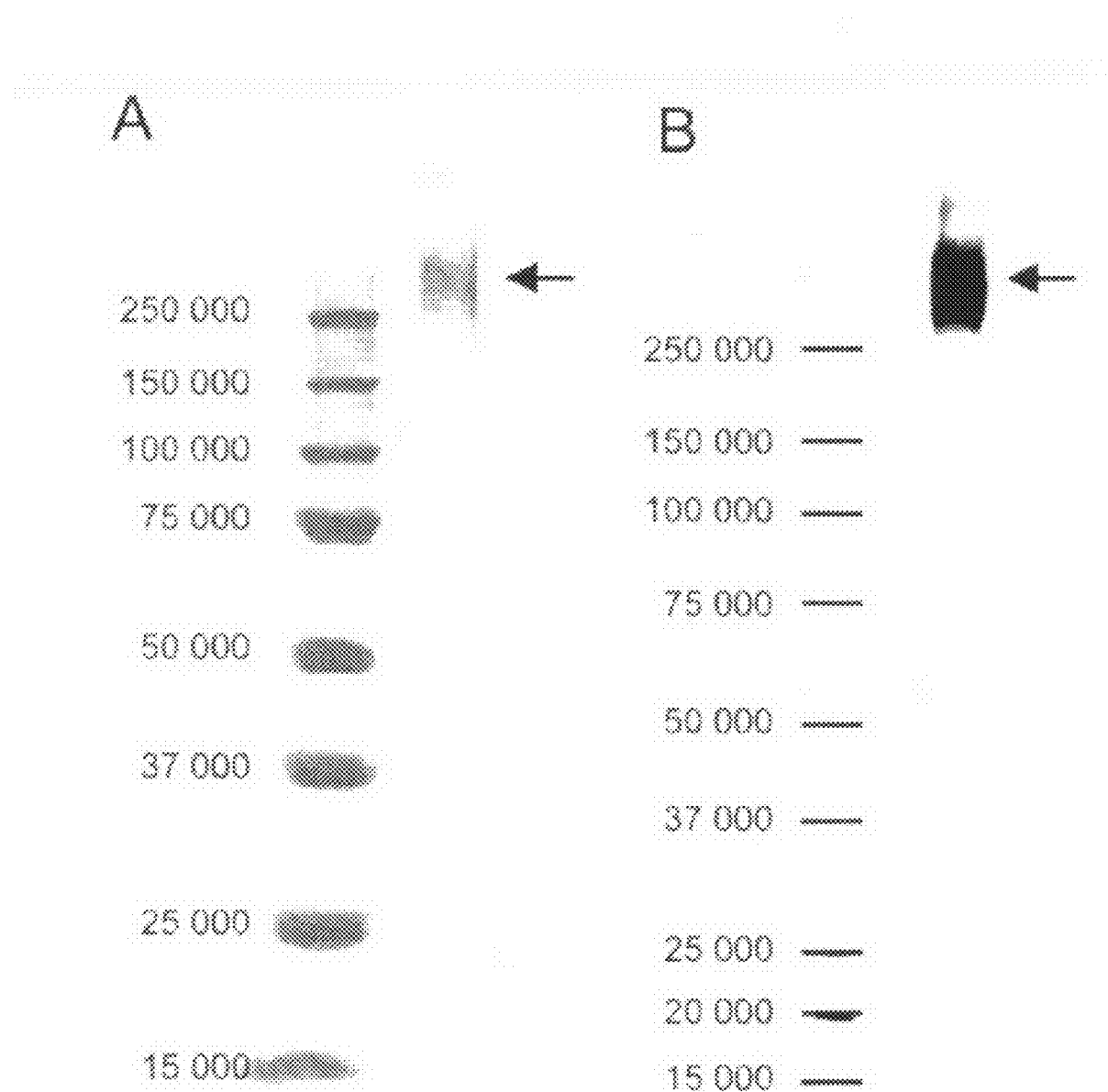

FIG. 12: Purified agrin-EGFP.

Purified engineered agrin-EGFP (indicated by arrows) shown on a silver-stained SDS gel (A) and on a Western blot, detected by an antibody raised against the C-terminal half of agrin (B). Molecular masses of standards (kDa) are indicated at the left margins. Note that EGFP is only used as a placeholder in this construct which has been designed to contain only the cleavage site α, but not the cleavage site β.

Figure 13:
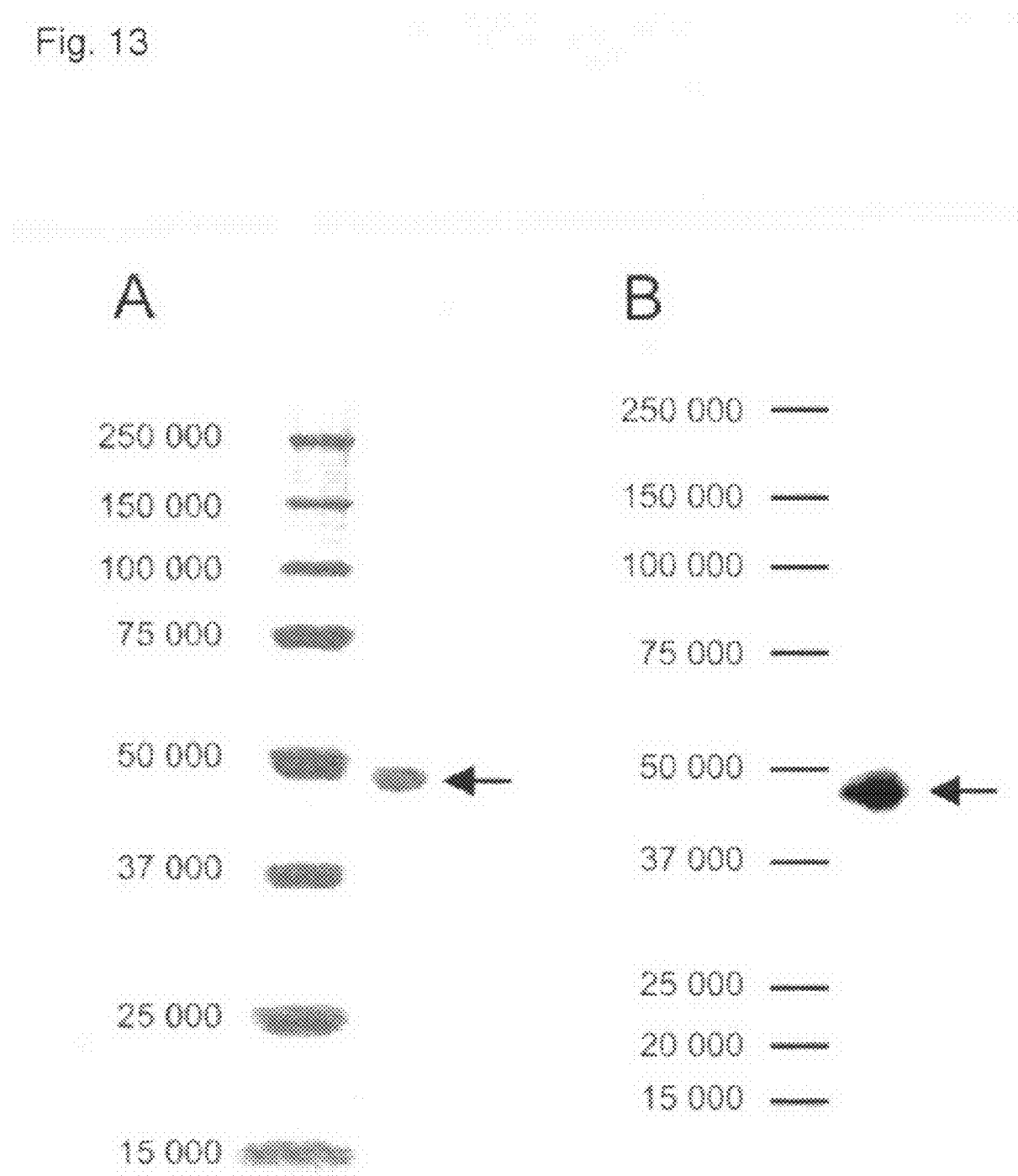

FIG. 13: Purified agrin-C45 fragment.

(A) Silver stained SDS-PAGE gel showing purified agrin-C45 fragment (indicated by arrows) migrating below 50 kilodaltons. The numbers indicate the molecular weights of the precision plus protein standard (BIORAD).

(B) Western blot detecting purified agrin-C45 fragment (indicated by arrows) using StrepTactin to detect the C-terminal strep tag. The numbers indicate the molecular weights of the precision plus protein standard (BIORAD).

Figure 14:
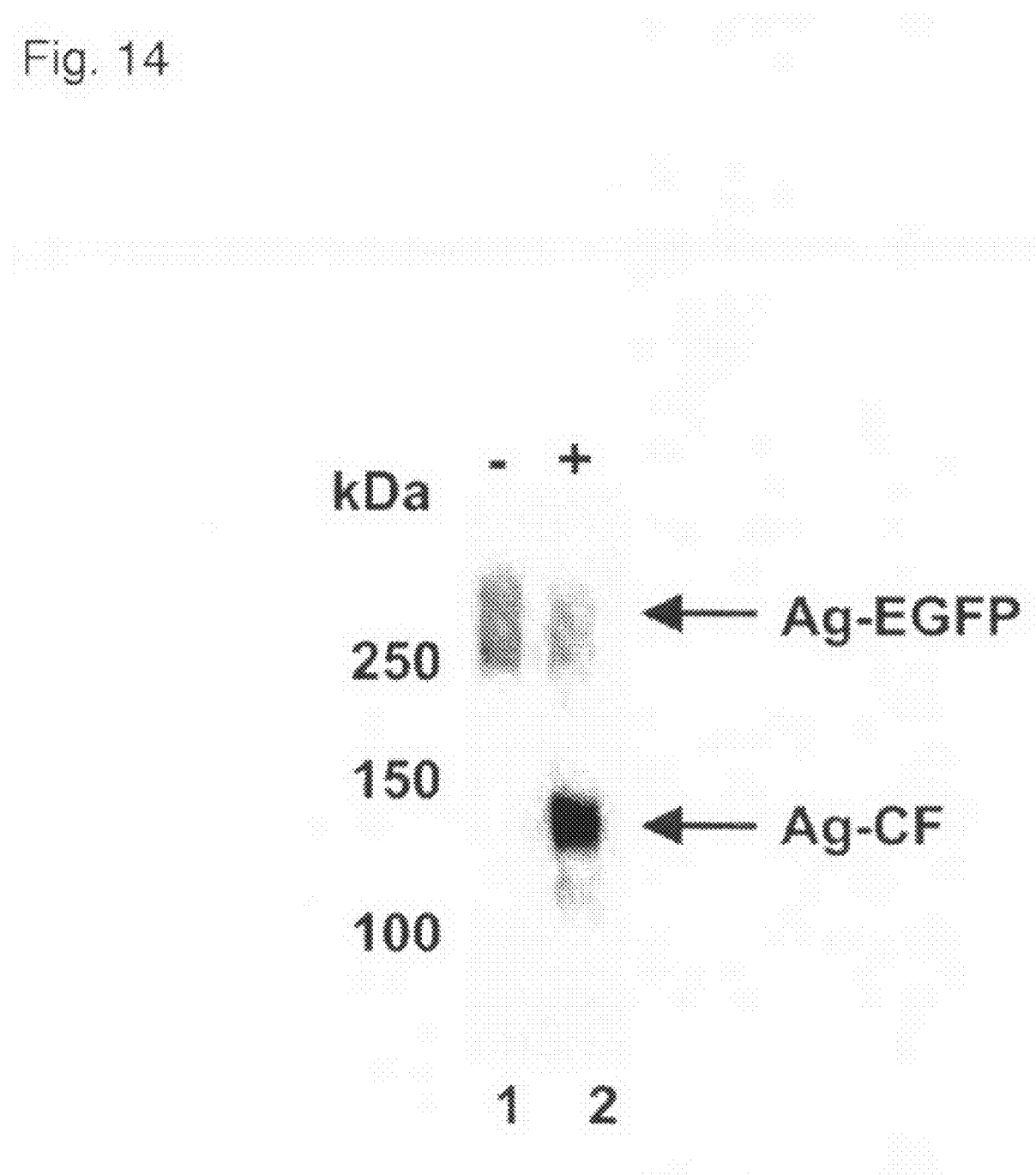

FIG. 14: Assay for neurotrypsin activity using agrin-EGFP as substrate.

To test for the activity of purified neurotrypsin on the cleavage site α, the substrate containing only the cleavage site α (agrin-EGFP) was incubated alone (−) and together with neurotrypsin (+), and then subjected to SDS-PAGE, followed by Western blotting using an antibody against the C-terminal cleavage fragment of agrin (see Example 22). Lane 1 shows agrin-EGFP (indicated by arrow marked Ag-EGFP) without neurotrypsin treatment as control. Lane 2 shows the agrin-EGFP (indicated by arrow marked Ag-EGPF) and the C-terminal fragment of approximately 150 kDa generated by neurotrypsin activity (indicated by arrow marked Ag-CF). Molecular weight marker in kDa (kilo dalton).

Figure 15:
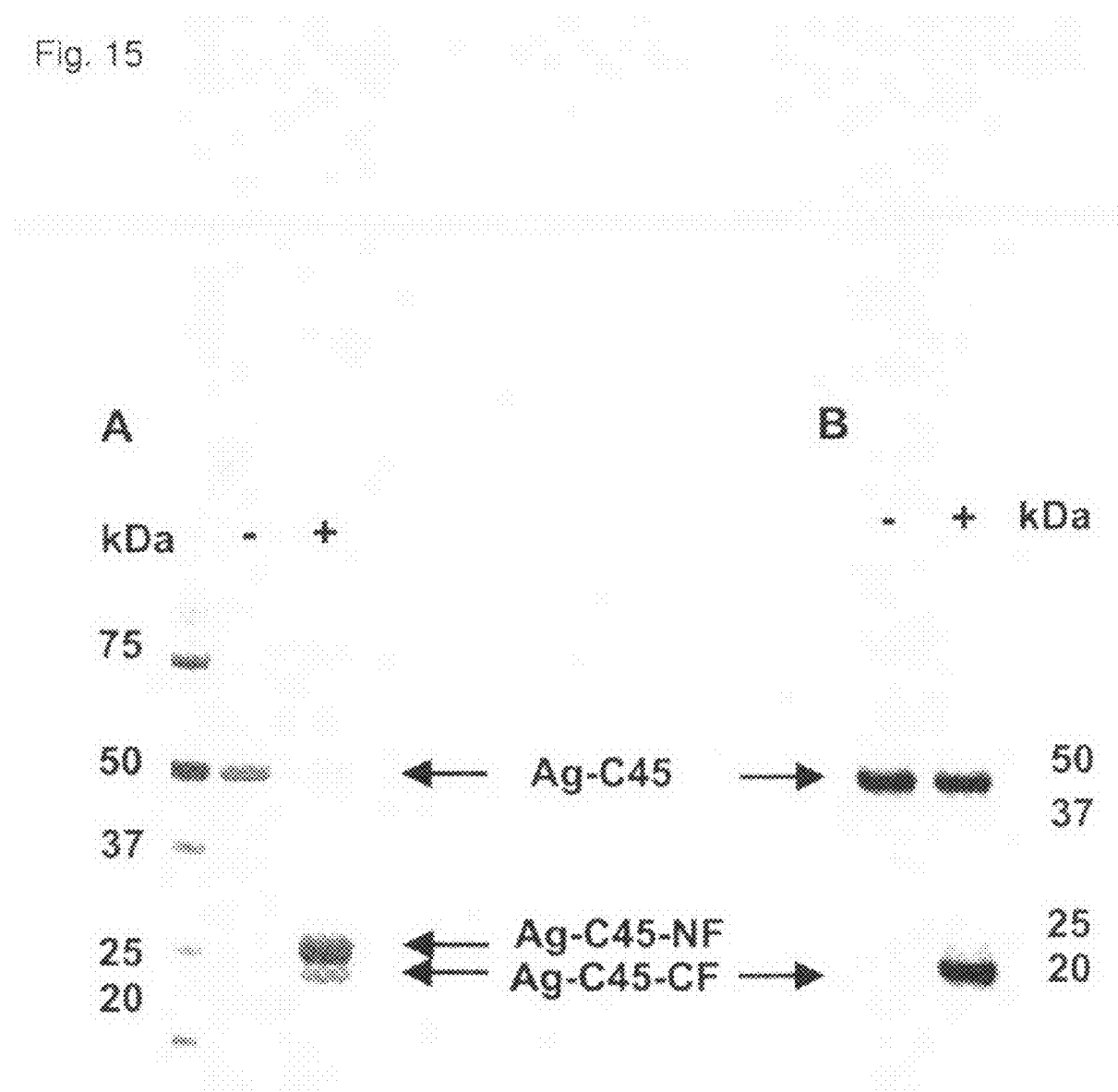

FIG. 15: Assay for neurotrypsin activity using agrin-C45 as a substrate.

To test for the activity of purified neurotrypsin on the cleavage site β of agrin, the substrate containing only the cleavage site β (agrin-C45) was incubated alone (−) and together with neurotrypsin (+), and then subjected to SDS-PAGE.

(A) Silver stained SDS-PAGE gel showing 250 ng agrin-C45 incubated in assay buffer for 3 hours without neurotrypsin (−) and 250 ng agrin-C45 incubated in assay buffer for 3 hours with the addition of neurotrypsin (+). Precision plus protein standard (BIORAD) shown on the left, numbers indicate molecular weights (kDa). Agrin-C45 (indicated by arrow) can be seen below 50 kDa. The cleavage products agrin-C45 are found between 20 and 25 kDa (indicated by arrows). Ag-C45-NF: N-terminal cleavage fragment of agrin-C45; Ag-C45-CF: C-terminal cleavage fragment of agrin-C45.

(B) Western blot of the same samples as in (A) where the uncleaved agrin-C45 and the cleaved C-terminal fragment of agrin-C45 are detected via their C-terminal Strep-tag, using StrepTactin (IBA GmbH). Ag-C45-CF: C-terminal cleavage fragment of agrin-C45 (indicated by arrow).

Figure 16:
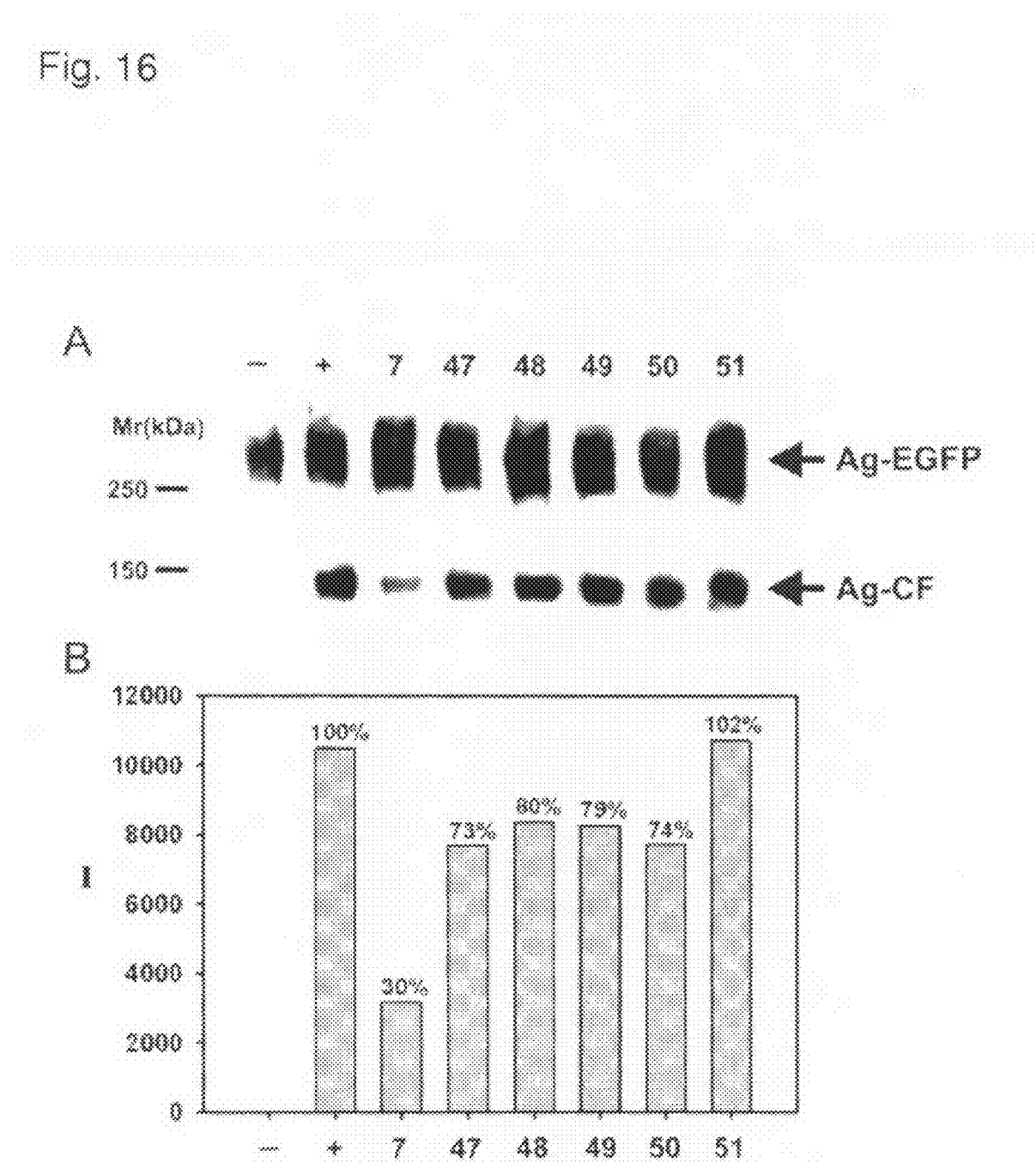

FIG. 16: Western blot-based screening assay for neurotrypsin inhibitors with antibody detection of agrin substrate and the C-terminal product.

The upper band shows the agrin-EGFP protein (arrow marked Ag-EGFP) with a molecular weight between 250 and 600 kDa used as substrate. The lower band shows the C-terminal fragment of agrin-EGFP generated by neurotrypsin with a molecular mass of approximately 150 kDa (arrow marked Ag-CF), which appears with different intensities, according to the inhibitory activity of the tested inhibitor molecules No. 7, 47, 48, 49, 50 and 51. The histogram shows the relative intensities (I) of the 150 kDa band (Ag-CF) generated by neurotrypsin-mediated cleavage of agrin-EGFP, with the positive control set to 100% and the negative control set to 0%. Negative control (−): only agrin-EGFP without neurotrypsin. Positive control (+): agrin-EGFP with addition of neurotrypsin.

No. 7: $N^1$-amidino-$N^4$-(3,5-dibromosalicylidene)-sulfanilamide

No. 47: 4-chlorocyclohex-4-ene-1,2-dicarboxylic acid $N^1$-amidinosulfanilamide

No. 48: $N^1$-amidino-$N^4$-(4-dimethylaminobenzylidene)-sulfanilamide

No. 49: $N^1$-amidino-$N^4$-benzylidene-sulfanilamide

No. 50: $N^1$-amidino-$N^4$-(2,4-dichlorobenzylidene)-sulfanilamide

No. 51: $N^1$-amidino-$N^4$-(4-methoxybenzylidene)-sulfanilamide

Figure 17:
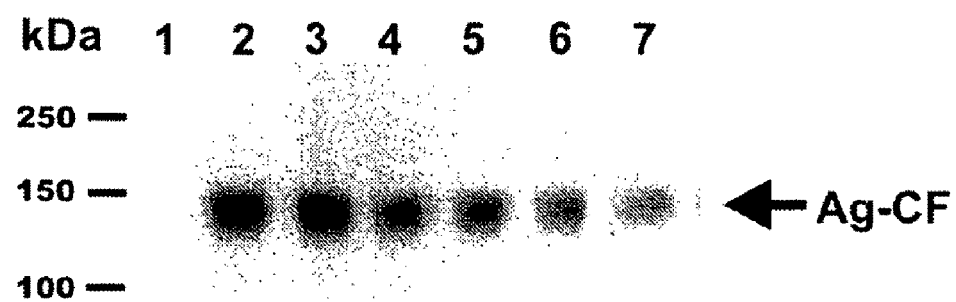
Figure 17:
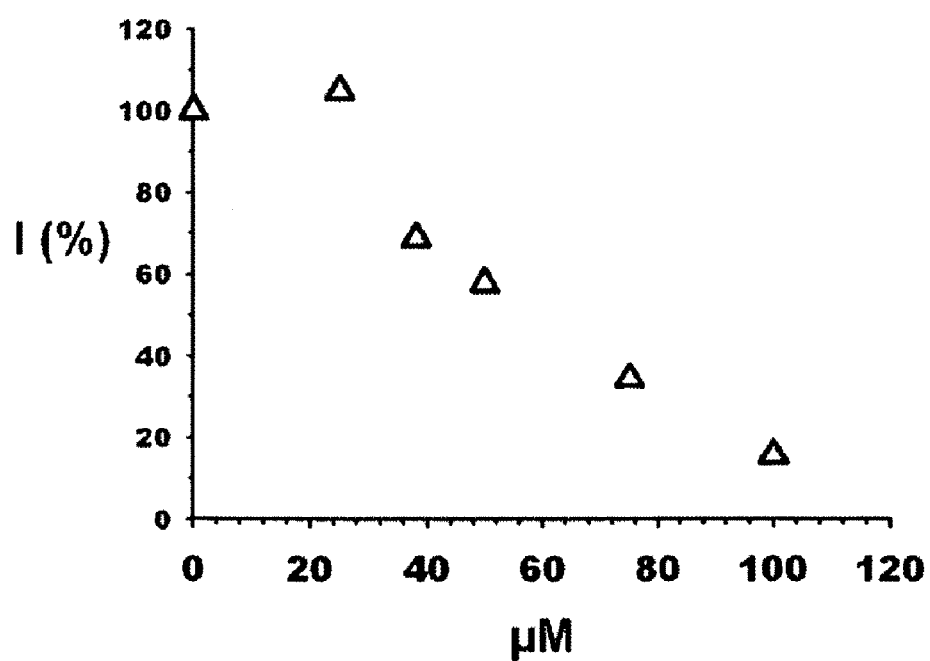
Figure 18:
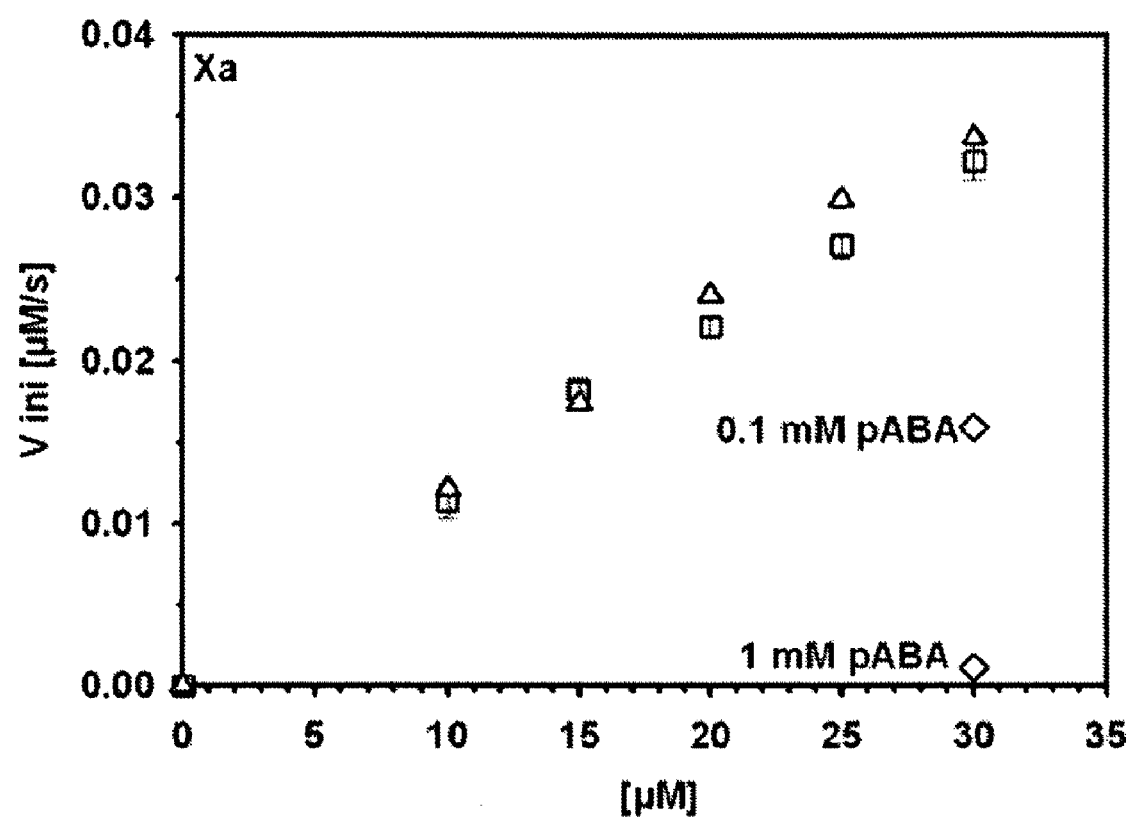
Figure 19:
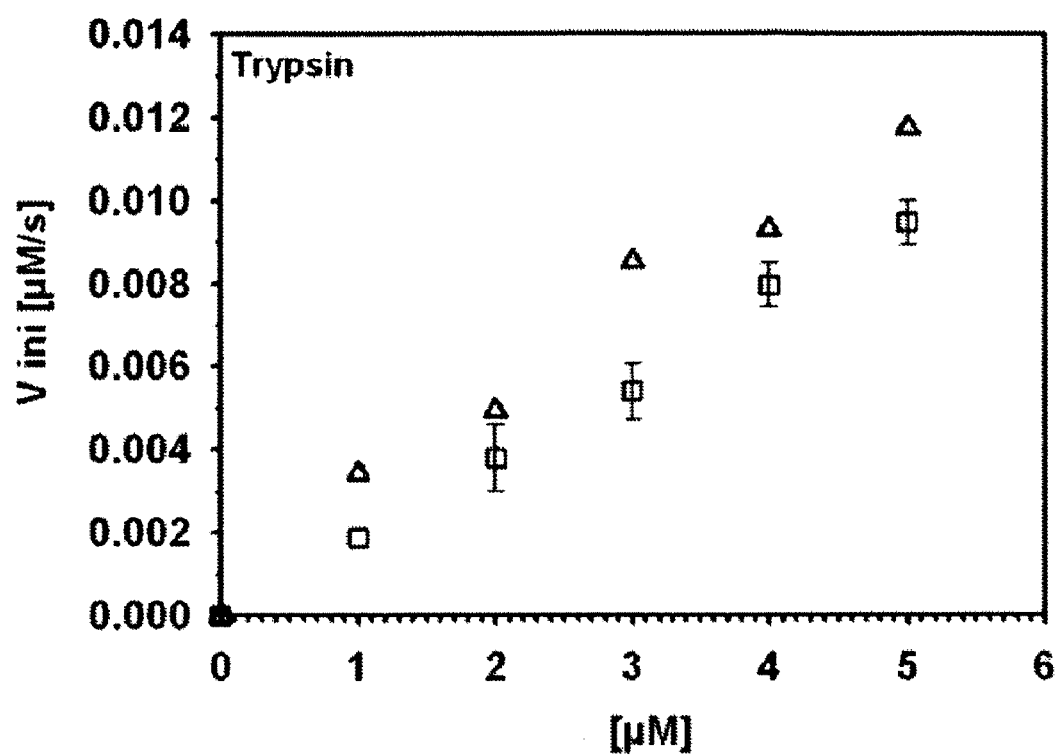
Figure 20:
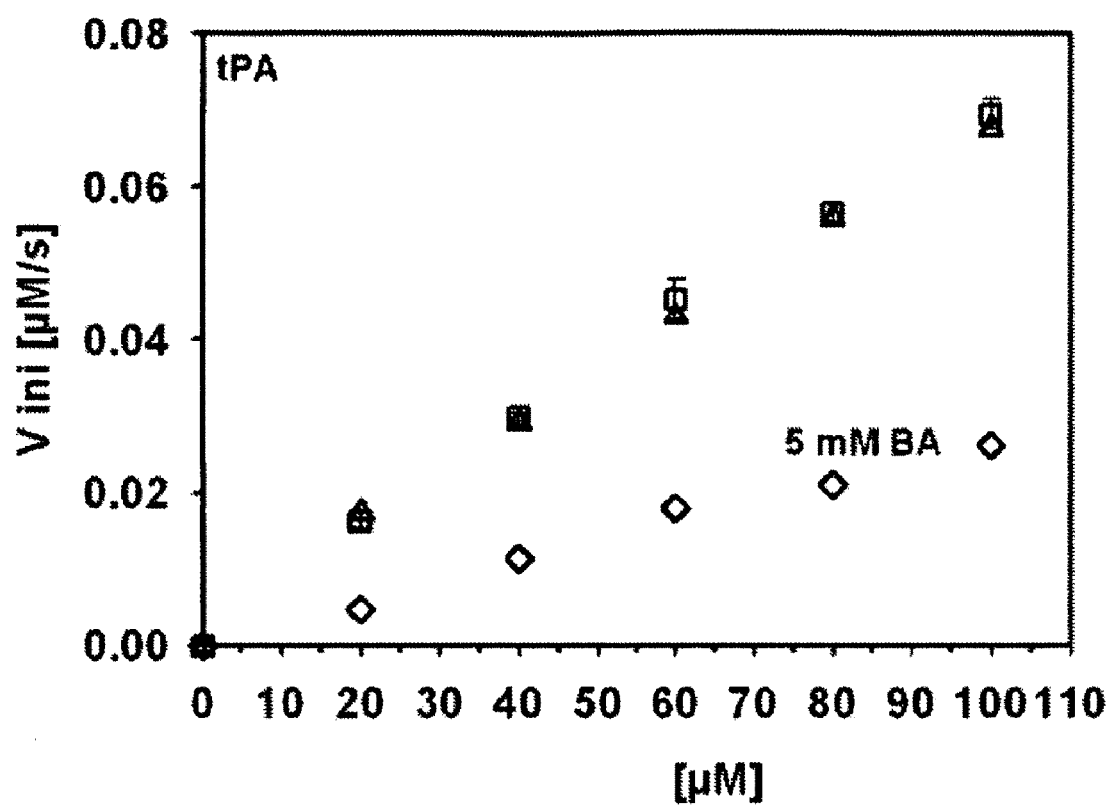
Figure 21:
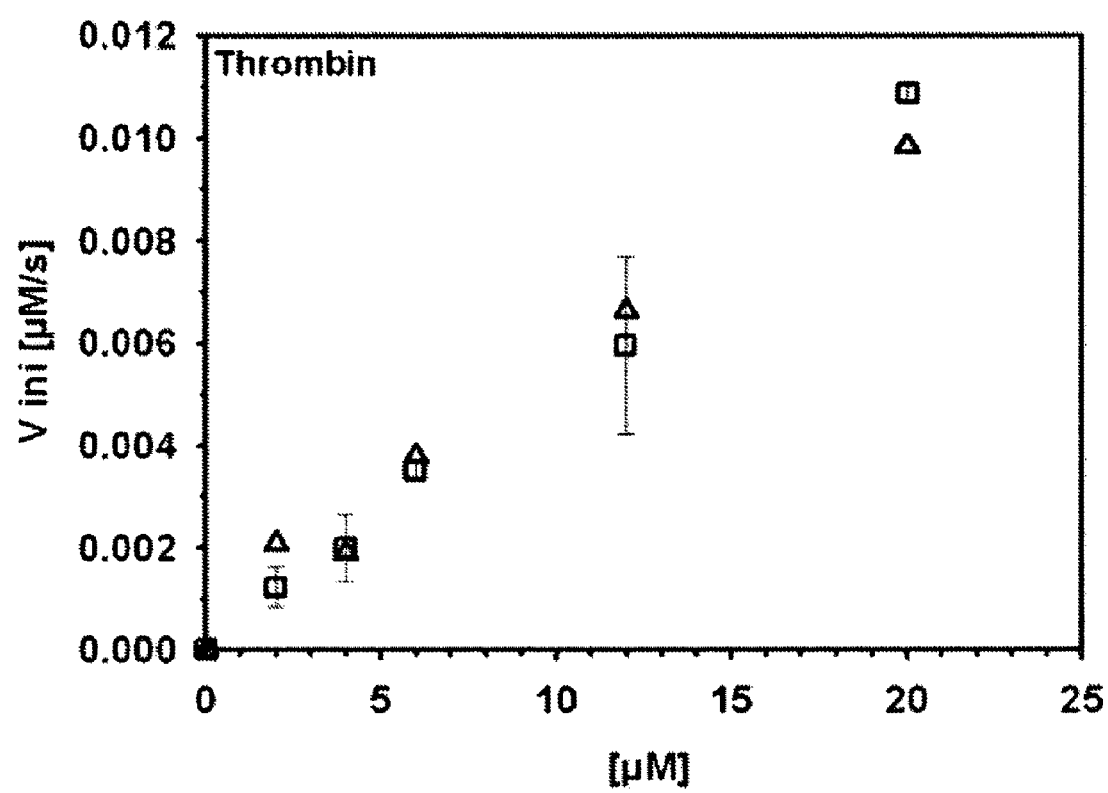
Figure 22:
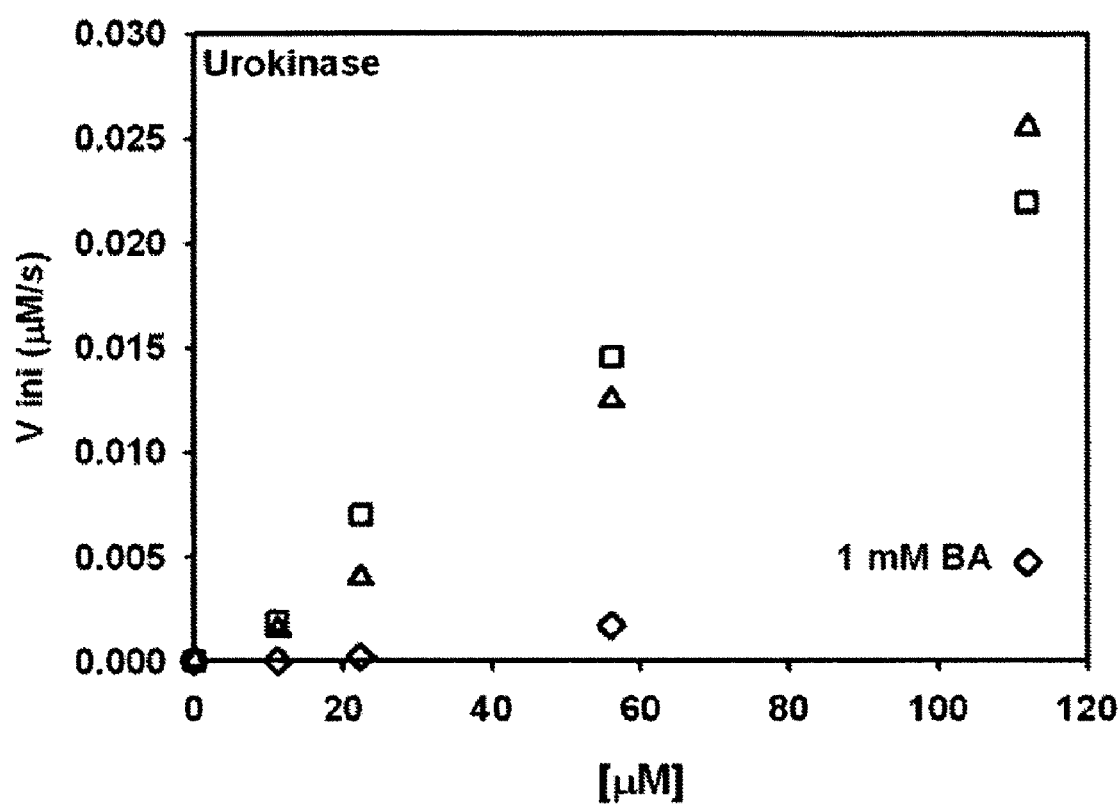
Figure 23:
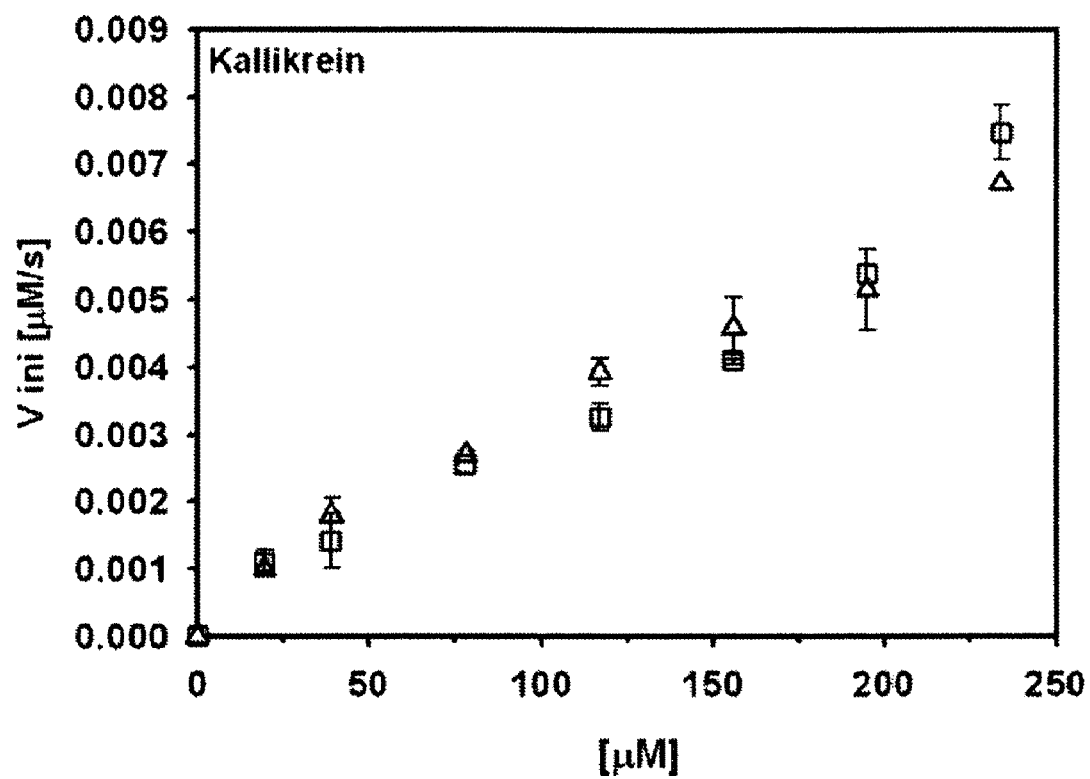
Figure 24:
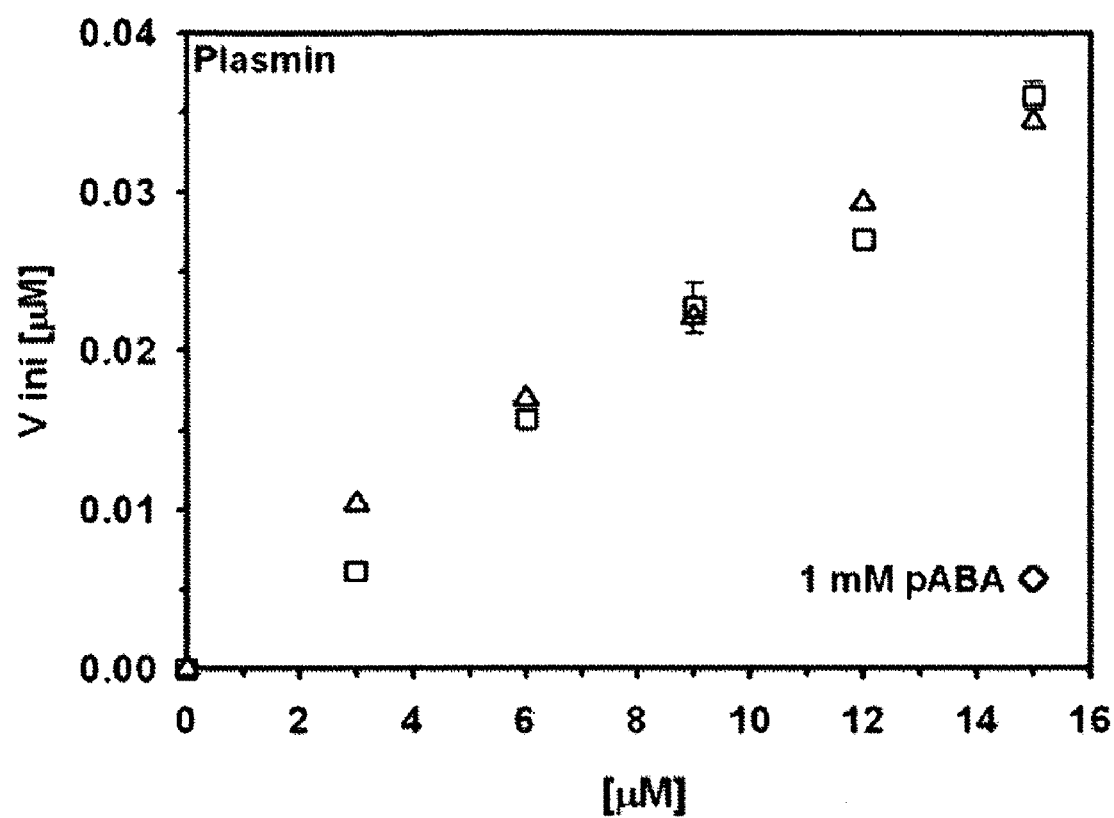

FIG. 17: Dose-dependent inhibition of neurotrypsin activity by compound No. 7.

(A) Western blot detection of the 150 kDa C-terminal fragment of agrin (Ag-CF) generated by neurotrypsin-mediated cleavage of agrin-EGFP in dependence of the concentration of compound No. 7, $N^1$-amidino-$N^4$-(3,5-dibromosalicylidene)-sulfanilamide.

Lane 1: Agrin-EGFP
Lane 2: Agrin+mouse neurotrypsin
Lane 3: Agrin+mouse neurotrypsin+25 μM compound No. 7
Lane 4: Agrin+mouse neurotrypsin+37.5 μM compound No. 7
Lane 5: Agrin+mouse neurotrypsin+50 μM compound No. 7
Lane 6: Agrin+mouse neurotrypsin+75 μM compound No. 7
Lane 7: Agrin+mouse neurotrypsin+100 μM compound No. 7

(B) Graphic plot of the intensity data from (A) against the inhibitor concentration with I=100% intensity for agrin+mouse neurotrypsin without addition of inhibitor compound No. 7.

FIG. 18-24: Specificity tests of compound No. 7 ($N^1$-amidino-$N^4$-(3,5-dibromo-salicylidene)-sulfanilamide): No inhibition of the tested proteases Xa, trypsin, tPA, thrombin, urokinase, kallikrein and plasmin.

The graphs show the initial reaction velocities (V ini) of the tested proteases Xa (FIG. 18), trypsin (FIG. 19), tPA (FIG. 20), thrombin (FIG. 21), urokinase (FIG. 22), kallikrein (FIG. 23), and plasmin (FIG. 24) plotted against the substrate concentrations (μM) in the absence (open squares) and the presence (open triangles) of compound No. 7. As positive control for competitive inhibition in the measurements for tPA (FIG. 20) and urokinase (FIG. 22) benzamidine (BA) and in the assays for Xa (FIG. 18) and plasmin (FIG. 24) para-aminobenzamidine (pABA) at the indicated concentrations were added (open diamonds).

DETAILED DESCRIPTION OF THE INVENTION

The invention is based on the fact that inhibition of neurotrypsin allows enhancing pro-synaptic (synapse-forming, synapse-differentiating, synapse-organizing, synapse-protecting, synapse-strengthening) activities. The neurotrypsin gene is expressed in many neurons of the central nervous system (Gschwend, T. P., et al., Molec. Cell Neurosci. 9: 207-219, 1997; Wolfer, D. P. et al., Molec. Cell. Neurosci. 18: 407-433, 2001), including the motoneurons of the spinal cord (Example 1), and the neurotrypsin protein is found in many CNS synapses (Molinari, F. et al., Science 298: 1779-1781, 2002), as well as at the neuromuscular junction. Neurotrypsin plays a substantial role in the development and/or the maintenance of a well balanced synaptic function. Too much neurotrypsin (overexpression) correlates with too few synaptic connections. Transgenic mice overexpressing neurotrypsin in CNS neurons show a reduced number of synapses in the cerebral cortex and the hippocampus, two brain structures that are highly important for cognitive functions, such as memory and learning. Likewise, transgenic mice over-expressing neurotrypsin in spinal motoneurons show a reduction of the neuromuscular junctions (NMJ), the synapses that mediate the neural control of muscular activity.

Alterations in the neuromuscular junctions of the diaphragm of transgenic mice which over-express neurotrypsin in motoneurons resemble those resulting from the targeted inactivation of the agrin gene. The proteoglycan agrin is a very well characterized pro-synaptic (synapse-forming, synapse-differentiating, synapse-organizing, synapse-protecting, synapse-strengthening) agent (Sanes, J. R. and Lichtman, J., Nature Rev. Neurosci. 2: 791-805, 2001). It has a core protein mass of approximately 220 kDa. Agrin exists in several isoforms. These encode both secreted extracellular matrix proteins and type-II transmembrane proteins that carry a very short N-terminal cytoplasmic segment. The region of agrin that bears the pro-synaptic activity is located in the C-terminal moiety of agrin, specifically in the $3^{rd}$ laminin G domain (Bezakova, G. and Ruegg, M. A., Nature Rev. Molec. Cell Biol. 4: 295-308, 2003). Agrin is a substrate of neurotrypsin (Example 2). Neurotrypsin cleaves agrin at two sites (Example 25). One site (termed α site) is located between arginine 995 (R995) and alanine 996 (A996). The other site (termed β site) is located between lysine 1754 (K1754) and serine 1755 (S1755). Amino acid numbers refer to membrane-anchored agrin (splice variant A4B0) of the rat (NP_786930). However, both the cleavage site α and the cleavage site β are well conserved in mammalian agrin, including human agrin. Agrin cleavage by neurotrypsin generates a fragment of approximately 100 kDa (kilo Dalton) ranging from A996 to K1754 and a fragment of approximately 22 kDa ranging from S1755 to the C-terminus. Cleavage of both the α and the β site separates agrin's synapse organizing activity from the N-terminal moiety of agrin. The cleavage of agrin occurs also in vivo. In wild-type mice, the 100-kDa fragment of agrin is found to occur most abundantly during the first postnatal weeks, the time when the developmental expression of neurotrypsin is at its peak (Example 3). The abundance of the 100-kDa fragment of agrin is markedly increased in transgenic mice overexpressing neurotrypsin in motorneurons (Examples 4 and 5).

Agrin is a natural substrate of neurotrypsin both at the NMJ (Example 6) and in the CNS (Example 14). By cleaving agrin, neurotrypsin counteracts the pro-synaptic activity of agrin. Excessive neurotrypsin at the neuromuscular junction of transgenic mice controls the disappearance of pre-established neuromuscular junctions within less than three days (Examples 4, 5, 6, and 7). These observations qualify neurotrypsin as a synapse-destabilizing or anti-synaptic agent.

The coexistence of pro- and anti-synaptic agents supports the concept that the neuronal circuitry of the nervous system is a dynamic rather than a fixed-wired system. A balanced match between pro-synaptic and anti-synaptic factors results in homeostasis. Adaptive changes that are required, for instance, when the synaptic connection need to be changed in order to satisfy altered needs, shift the balance between pro-synaptic and anti-synaptic forces in a controlled manner. This subtle, tightly controlled interplay between pro- and anti-synaptic forces is vulnerable to dysregulation resulting in an inappropriate synaptic homeostasis or inappropriate adaptation to the functional requirements. A synaptic disease may result when the extent of the dysregulation exceeds a threshold value.

The pharmaceutical tuning of neurotrypsin's activity provides an unprecedented access to the regulatory machinery of synaptic function. Inhibiting neurotrypsin's proteolytic activity will shift the synaptic balance towards strengthening the pro-synaptic activities at the expense of the anti-synaptic activities and thus towards increasing the number and/or the size and/or the strength of synapses.

Experiments with transgenic mice overexpressing neurotrypsin in spinal motoneurons show a correlation between skeletal muscle atrophy (Examples 8 and 10) and deterioration of synaptic connections (Example 9). Inhibitors of neurotrypsin will counterbalance the result of excess neurotrypsin and allow treatment and prophylaxis of skeletal muscle atrophy caused by loss of synaptic connections, for example skeletal muscle atrophy in old-age patients.

In transgenic mouse lines that overexpress neurotrypsin in motoneurons, a striking atrophy of skeletal muscles is observed that is mainly due to a marked reduction in the number of muscle fibers (Example 10). A quantitative assessment of the effect of excessive production of neurotrypsin by motoneurons is given in Table 1. Excessive levels of neurotrypsin produced by motoneurons result in a reduction in the number of muscle fibers of the soleus muscle of adult mice ranging from 18 to 48% depending on the level of neurotrypsin overexpression. Because neurotrypsin overexpression was restricted to motoneurons (for experimental details see Example 4), these results indicate that neurotrypsin expressed by motoneurons acts locally via the neuromuscular junction on the target muscle fiber. This local atrophic effect strictly depends on the proteolytic activity of neurotrypsin, since muscles of mice overexpressing a catalytically inactive form of neurotrypsin exhibit normal fiber numbers.

Mice overexpressing neurotrypsin in motoneurons exhibit a significantly enhanced fragmentation of the neuromuscular junctions (Example 9). Fragmentation combined with a decreased fiber number is a characteristical feature observed in skeletal muscles of aged humans and animals. As mentioned above, the deterioration of the neuromuscular junctions and the loss of muscle fibers are not elicited by the overexpression of catalytically inactive neurotrypsin. This characterizes motoneuron-derived neurotrypsin as a factor that reduces the innervation of muscle fibers and ultimately causes their loss. Agents with an innervation-reducing activity have been hypothesized to play a role during the stage of developmental synapse elimination, both at the neuromuscular junction and in the central nervous system. It is possible that a synapse-reducing activity persists throughout adult life and plays a role in the maintenance of a balance between presynaptic and postsynaptic elements. The temporal pattern of neurotrypsin expression supports this possibility, as it peaks during the period of developmental synapse elimination (first two postnatal weeks in mice and rats) and subsequently remains expressed at a lower level throughout adult life.

Neurotrypsin overexpression in motoneurons of transgenic mice results in a degradation of the neuromuscular junction (Example 7). Systematic analyses of the role of neurotrypsin for the maintenance of the neuromuscular junction in different types of muscles, including the diaphragm and the soleus muscle, reveals that overexpression of neurotrypsin in motoneurons reduces the size of the neuromuscular junction. Strong overexpression of neurotrypsin in motoneurons results in a complete dispersal of previously established neuromuscular junctions. As a consequence of the synapse-degrading effect of neurotrypsin, the motor nerves left without a postsynaptic specialization and/or with a structurally and functionally reduced postsynaptic specialization, start to grow beyond the site of the previous NMJ. The nerves now growing over the muscle fiber surface establish small ectopic synapses that appear immature upon electron-microscopic inspection, as concluded from the absence of secondary folds in the postsynaptic membrane.

Neurotrypsin overexpression in motoneurons of transgenic mice results in the cleavage of the proteoglycan agrin (Example 5). As a consequence, the C-terminal moiety of agrin disappears from the NMJ (Example 6). The region of agrin that bears the NMJ-conserving and NMJ-promoting activity of agrin is located in the C-terminal moiety of agrin, specifically in the $3^{rd}$ laminin G domain (Bezakova, G., Nature Reviews Molecular Cell Biology 4: 295-308, 2003). Therefore, the removal of the C-terminal domain of agrin leaves the NMJ unprotected from the so-called dispersal factor, and the NMJ decays and disappears within days. The upregulation of neurotrypsin in motoneurons at the time when the Thy-1 promoter starts to drive the expression of the neurotrypsin transgene (2-5 days after birth), results in the disappearance of agrin from the NMJ within a period of days (Example 6). Shortly after the disappearance of agrin, the postsynaptic acetylcholine receptor disappears as well (Example 7). In summary, these observations indicate a chain of events that starts with the upregulation of neurotrypsin in motoneurons. Excessive neurotrypsin, in turn, cleaves agrin at the NMJ and removes agrin's C-terminal moiety from the NMJ. Because the C-terminal moiety contains the active site of agrin's NMJ-protecting and NMJ-promoting capacity, the NMJ is now left unprotected against the dispersal factor and in turn is degraded.

The observation of a marked reduction of nerve fiber number in skeletal muscles of mice that overexpress neurotrypsin selectively in motoneurons indicates that neurotrypsin is causally related to endplate deterioration resulting in denervation followed by atrophy and ultimately loss of denervated muscle fibers. These observations are in accordance with the observations made at muscles and neuromuscular junctions of humans and animals with age-dependent skeletal muscle atrophy. In a situation, where age-dependent muscle fiber loss occurs due to the convergent action of multiple factors, controlled and subtle partial inhibition of neurotrypsin may interrupt the process of endplate deterioration, denervation, and muscle fiber loss. Therefore, the inhibition of neurotrypsin is expected to have a beneficial effect on age-dependent muscle fiber denervation, muscle fiber loss, and skeletal muscle atrophy.

Skeletal muscle atrophy is accompanied by a substantial loss of muscle strength and plays a major role in the pathogenesis of frailty and functional impairment that occurs with progressive old age. Weakness of the lower extremities has been implicated in a number of functional impairments, such as difficulties in rising from a chair or getting out of bed, slow speed of gait and other movements, and difficulties to maintain balance, resulting in falls and injuries. Skeletal muscle fiber loss has a negative effect on both the absolute strength that a muscle can develop and the speed with which a muscle can develop strength.

Increasing age is associated with a progressive decrease of the metabolic rate, which in turn has substantial physiological consequences, including a reduced tolerance against heat and cold as well as an increased propensity to develop obesity. Skeletal muscles comprise approximately 40% of the fat-free body mass and play an important homeostatic role in the body's metabolism. Therefore, a reduction of the skeletal muscle mass with increasing age is a major contributor to the decreased metabolic rate. By preventing the progressive fiber loss, the inhibition of neurotrypsin acts against these metabolic and physiological consequences.

Progressive loss of skeletal muscle mass and strength with age has been recognized as a major contributor to the gradual reduction of bone density observed with increasing age. Conversely, it is well known that the forces exerted on the bones by muscular activity stimulate bone formation. Thus, forces generated by muscle contraction are an important determinant of bone quality. Preventing muscle fiber loss by inhibition of peripheral neurotrypsin activity may therefore prevent or linder the adverse effects on skeletal muscle quality and indirectly antagonize progression of osteoporosis.

Beneficial effects of neurotrypsin inhibition may also be expected for skeletal muscle atrophies that occur in numerous clinical situations in which muscle wasting is an accompanying problem, including cancer, AIDS, and sepsis.

Neurotrypsin has also an anti-synaptic function in the central nervous system (CNS). Neurotrypsin mRNA is expressed by neurons of the grey matter of the CNS (Gschwend, T. P., et al., Molec. Cell Neurosci. 9: 207-219, 1997) and neurotrypsin protein is abundant in synapse-rich regions in many brain areas (Molinari, F. et al., Science 298: 1779-1781, 2002). Particularly high concentrations of neurotrypsin protein are found in synapse-rich regions of the cerebral cortex, the hippocampus, and the amygdala. However, other synapse-rich regions also exhibit abundant expression of neurotrypsin. At higher magnification, neurotrypsin protein is found in the membrane of the presynaptic terminal, in particular the membrane area lining the synaptic cleft (Molinari, F. et al., Science 298: 1779-1781, 2002). The most intensive immunostaining for neurotrypsin is found over the synaptic active zones of the presynaptic terminal. Occasionally, neurotrypsin immunoreactivity is also observed in vesicles of the presynaptic terminal. It is noteworthy, however, that the majority of the presynaptic vesicles are devoid of neurotrypsin immunoreactivity. Independent evidence for the synaptic localization of neurotrypsin is obtained by a biochemical approach, i.e. by the analysis of synaptosomes. The immunocytochemical localization of neurotrypsin in the membrane at the presynaptic active zone is identical in humans and mice. In summary, the results indicate that neurotrypsin is located in the presynaptic terminal, in particular in the presynaptic membrane lining the synaptic cleft at the presynaptic active zone.

By its localization at the synapse, in particular the presynaptic active zone, neurotrypsin is situated in a strategic position to control synaptic structure and function. The role of neurotrypsin as a modulator of synaptic structure and function, in particular its function as an anti-synaptic agent in the CNS, is demonstrated by experiments with transgenic mice overexpressing neurotrypsin in CNS neurons (Example 11). Excessive amounts of neurotrypsin produced by CNS neurons cause a significant reduction in number and size of the synapses in the central nervous system. Evidence for structural changes is found both with morphological and electrophysiological methods.

Counting synapses in neuropil regions shows a reduction in the number of synapses per area (Example 12). Inspection of the dendritic spines along dye-filled dendrites shows a reduction in the size and the number of spines in neurotrypsin-overexpressing mice (Examples 13). These results are in mutual agreement, because many synapses end on dendritic spines. Therefore, fewer synapses and fewer dendritic spines represent two readouts of the same phenomenon. Taken together, these observations clearly demonstrate an anti-synaptic function of neurotrypsin.

Also in the CNS, neurotrypsin mediates the cleavage of agrin (Examples 14 and 15). The proteoglycan agrin is present both at the neuromuscular junction (Sanes, J. R. and Lichtman, J., Nat. Rev. Neurosci. 2: 791-805, 2001) and at synapses of the central nervous system (Smith, M. A. and Hilgenberg, L. G., Neuroreport 13: 1485-1495, 2002; Kroger, S. and Schroder, J. E., News Physiol. Sci. 17: 207-212, 2002). In CNS homogenates of wild-type mice, the 100-kDa fragment of agrin is found to occur most abundantly during the first postnatal weeks, the time when the developmental expression of neurotrypsin is at its peak (Example 14). The abundance of the 100-kDa fragment of agrin is markedly increased in transgenic mice overexpressing neurotrypsin in CNS neurons (Example 15). In the presence of neurotrypsin that has been inactivated by replacing the active site serine by an alanine no cleavage of agrin occurs. Thus, the proteolytic activity of neurotrypsin clearly mediates cleavage of agrin and generation of the 100-kDa fragment of agrin in the CNS.

The form of agrin used in these experiments is the membrane-anchored form. This N-terminally linked form of agrin is predominantly found in the central nervous system and has been reported to control synapse differentiation in the CNS (Bose, C. M. et al., J. Neurosci. 20: 9086-9095, 2000).

In summary, neurotrypsin has an anti-synaptic function not only at the NMJ, but also in the CNS. Too much neurotrypsin (overexpression) correlates with too few synaptic connections in the cerebral cortex and in the hippocampus, two brain structures that are highly important for cognitive functions, such as memory and learning. The synapse-organizing proteoglycan agrin is also a physiological substrate of neurotrypsin in the CNS. By cleaving agrin, neurotrypsin counteracts the pro-synaptic activity of agrin.

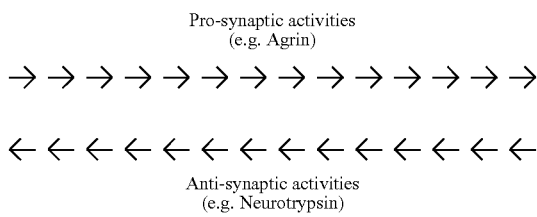

The coexistence and the interaction of the pro-synaptic agent agrin and the anti-synaptic agent neurotrypsin in the CNS support the concept that the neuronal circuitry of the nervous system is a dynamic rather than a fixed-wired system. Homeostasis is maintained by a balanced match between pro-synaptic and anti-synaptic factors. When adaptive changes are required, for instance, when the circuitry needs to be changed to store memories, the balance between pro-synaptic and anti-synaptic forces is shifted in a controlled manner. When the change in the circuitry is achieved, the balance between pro-synaptic and anti-synaptic forces is restored.

The subtle, tightly controlled interplay between pro- and anti-synaptic forces is vulnerable to dysregulation resulting in an inappropriate synaptic homeostasis or inappropriate adaptation to the functional requirements. A synaptic disease may result when the extent of the dysregulation exceeds a threshold value.

The pharmaceutical tuning of neurotrysin's activity provides an unprecedented access to the regulatory machinery of synaptic function. Inhibiting neurotrypsin's proteolytic activity results in a longer lifespan and, therefore, an increased concentration of agrin. Due to this linkage between neurotrypsin and agrin the reduced anti-synaptic activity, induced by neurotrypsin inhibition, boosts the pro-synaptic activity of agrin. As a consequence, the balance is shifted towards enhancement of pro-synaptic activity resulting in an increase in synapse number, size, and strength.

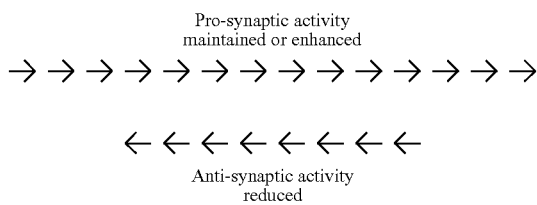

The concept of synapse tuning by reducing the anti-synaptic activity of neurotrypsin and, thereby, enhancing pro-synaptic activities at the expense of anti-synaptic activities, offers a wide range of applications in the area of disturbed cognitive brain functions. In particular, inhibition of neurotrypsin is beneficial in diseases and subclinical situations where synapse formation and the increase in the size and the strength of existing synapses is needed.

Inhibition of neurotrypsin is useful in the treatment of schizophrenia. Excessive neurotrypsin at the synapse drives synaptic pruning and, thus, generates a synaptic phenotype that is in accordance with the synaptic phenotype found in the brain of patients with schizophrenia. This experimental observation qualifies neurotrypsin as one of the factors that drive synaptic pruning. In a situation, where excessive synaptic pruning occurs due to the convergent action of multiple pruning-promoting factors, controlled and subtle partial inhibition of neurotrypsin diminishes the drive for synaptic pruning. This allows a recovery from the "schizophrenic synaptic phenotype" and results in the alleviation of the schizophrenic symptoms. The reduction of synapse numbers in the CNS of neurotrypsin-overexpressing mice indicates that inhibition of neurotrypsin results in a lesser degree of synaptic pruning and, thus, increased synaptic number and enhanced neuronal connectivity and communication. Compounds according to the invention inhibiting the enzymatic function of neurotrypsin are, therefore, useful in reverting the synaptic alterations in schizophrenia and in re-establishing normal synaptic structure and function and, thus, stop or shorten schizophrenic episodes and protect from new episodes.

Inhibition of neurotrypsin also supports cognitive enhancement in mild cognitive impairment and other clinical and subclinical states with reduced cognitive functions. Mild cognitive impairment, as well as other clinical and subclinical states of impaired cognitive functions have been found to be associated with evidence for cerebral tissue atrophy in several CNS areas. The reduction of synapse numbers in the CNS of neurotrypsin-overexpressing mice indicates that inhibition of neurotrypsin results in an increased synaptic number and enhanced neuronal connectivity and communication. Compounds according to the invention inhibiting the enzymatic function of neurotrypsin are, therefore, useful in reverting the synaptic alterations in all clinical and subclinical disorders in which a reduced number of synapses or a reduced function of synapses is involved, and in re-establishing normal synaptic structure and function. By this, pharmaceutical inhibition of neurotrypsin may improve cognitive functions in different states with reduced cognitive functions of heterogenous origins.

Based on these facts, the invention further relates to the use of neurotrypsin inhibitors of formula (1) as described above and below for the treatment and/or prophylaxis of diseases caused by deficiency of synapses, for example skeletal muscle atrophy, schizophrenia and cognitive disturbance. Skeletal muscle atrophy to be treated is in particular so-called sarcopenia, i.e. a skeletal muscle atrophy due to old age, skeletal muscle atrophy accompanied by osteoporosis, and skeletal muscle atrophy due to muscle wasting associated with a severe disease, such as cancer, AIDS and sepsis, or also skeletal muscle atrophy as a consequence of immobilization and/or bed rest due to a severe injury or a severe disease. Schizophrenia to be treated is a disorder in the entire field of schizophrenia and schizophrenia-like disorders, comprising chronic schizophrenia, chronic schizo-affective disorders, unspecific disorders, acute and chronic schizophrenia of various symptomatologies, as for example severe, non-remitting "Kraepelinic" schizophrenia or the DSM-III-R-prototype of the schizophrenia-like disorders, episodic schizophrenic disorders, delusionic schizophrenia-like disorders, schizophrenia-like personality disorders, as for example schizophrenia-like personality disorders with mild symptomatics, schizotypic personality disorders, the latent forms of schizophrenic or schizophrenia-like disorders, and non-organic psychotic disorders. Furthermore, neurotrypsin inhibitors as described herein may be used as cognitive enhancers, for improving brain performance and for ameliorating learning and memory functions. Cognitive deficiencies to be treated are mild cognitive impairment, e.g. in a potential early stage of Alzheimer's disease, impairment of cognitive function without dementia in elderly people, and impairment of cognitive functions in patients with Alzheimer's disease, Parkinson's disease, multiple sclerosis, stroke, and head trauma.

Likewise the invention relates to the use of such inhibitors of formula (1) for the manufacture of a medicament for the treatment and/or prophylaxis of diseases caused by deficiency of synapses, for example skeletal muscle atrophy, schizophrenia and cognitive disturbance. Furthermore the invention relates to the treatment and/or prophylaxis of diseases caused by deficiency of synapses, for example skeletal muscle atrophy, schizophrenia and cognitive disturbance, which comprises administering a compound of formula (1) or a pharmaceutically acceptable salt thereof, in a quantity effective against said disease, to a warm-blooded animal requiring such treatment. The compounds of formula (1) can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.05 g to approximately 5 g, preferably from approximately 0.25 g to approximately 1.5 g, of a compound of the present invention.

Figure 1:
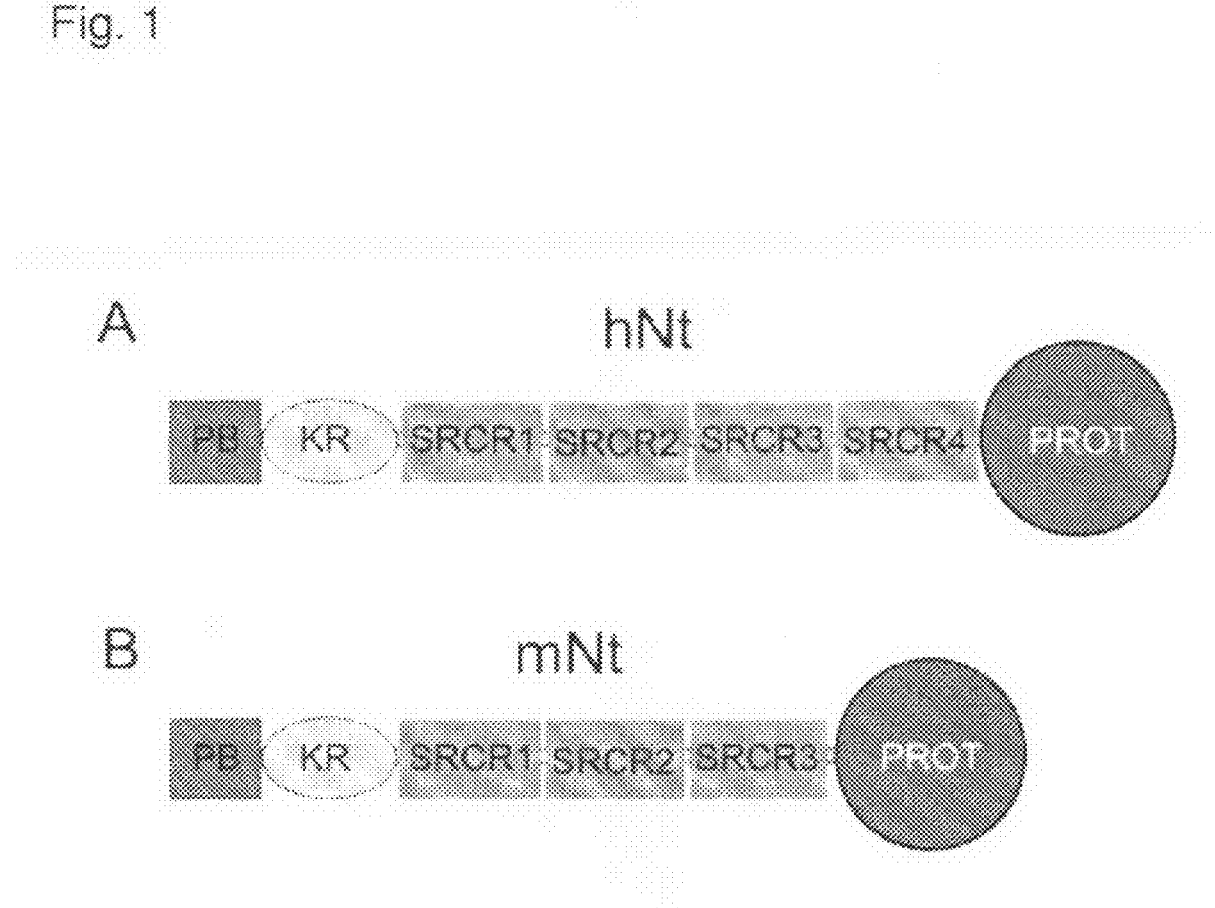
FIG. 1: Domain structure of neurotrypsin.

Neurotrypsin is composed of a proline-rich basic domain (PB), a kringle domain (KR), three (mouse neurotrypsin, mNT) or four (human neurotrypsin, hNT) scavenger receptor cysteine-rich domains (SRCR1, SRCR2, SRCR3, and SRCR4), and a protease domain (PROT) (FIG. 1). The zymogen activation (ZA) site represents a cleavage site at the N-terminus of the protease domain of neurotrypsin. Proteolytic cleavage at the ZA site converts the neurotrypsin protein from a catalytically inactive to a catalytically active form. By this cleavage, a fragment of approximately 55 kDa, comprising the non-catalytic region, and a fragment of approximately 30 kDa, comprising the protease domain, are generated in the case of mouse neurotrypsin. In the case of human neurotrypsin, the fragments generated have a molecular weight of 67 kDa and 30 kDa, respectively.

The biochemical analysis of human neurotrypsin and the search for neurotrypsin inhibitors requires protein amounts in the milligram to gram range. Several eukaryotic expression systems have been tested for optimal production and secretion of neurotrypsin, including stable expression in mouse myeloma cells, baculovirus-mediated expression in insect cells, and transient expression in human embryonic kidney (HEK) cells, transient expression in Chinese hamster ovary (CHO) cells, and stable expression in *Picchia pastoris*. These systems have the advantage that they can easily be adapted to serum-free conditions to reduce the amount of contaminating proteins in the supernatant and to set-ups for large-scale production. Expression of neurotrypsin can be accomplished in all of these expression systems. However, the most efficient production and secretion of neurotrypsin is obtained in myeloma cells, as described in Examples 16 and 17.

Expression in eucaryotic cells may, alternatively, be achieved with a variety of eucaryotic expression vectors (commercially available or self-made). Likewise, a variety of eucaryotic cell lines may be used, including HEK293T and HEK293-EBNA cells, COS cells, CHO cells, HeLa cells, H9 cells, Jurkat cells, NIH3T3 cells, C127 cells, CV1 cells, or Sf cells.

The production of neurotrypsin may also be based on mammalian cell lines exhibiting endogenous expression of neurotrypsin. Expression of endogenous human neurotrypsin has been observed at the RNA level in the human mast cell line HMC-1 (Poorafshar, M. and Hellman, L., Eur. J. Biochem. 261: 244-250, 1999). The HMC-1 cell line represents a naturally occurring source for properly processed and, therefore, very likely for active human neurotrypsin. These cells can be grown in suspension culture and constitutively express human neurotrypsin. The protein expressed from HMC-1 cells can be detected as 97 kDa band by a specific polyclonal antibody raised against the kringle domain in Western blot experiments.

For purification of neurotrypsin standard protein purification procedures are applied (Examples 18 and 19). Preferably, affinity purification on a heparin column, then a hydrophobic interaction column and an immobilized metal-chelate chromatography column are used. The eluted protein is then further purified by ion-exchange chromatography on a Mono S column. Depending on the experimental requirements, additional or alternative chromatography steps on ion-exchange (DEAE or Mono Q) columns or by gel filtration are also useful for the purification of neurotrypsin.

The invention relates to a method for measuring the catalytic activity of neurotrypsin, characterized in that neurotrypsin, a variant thereof or a fragment comprising the protease domain of neurotrypsin, and a protein or peptide comprising agrin, a variant thereof or a fragment comprising the cleavage site α or the cleavage site β of agrin (Examples 20 and 21), are incubated together in an aqueous buffer solution, and the amount of cleavage of agrin is measured (Example 24).

As used herein, "a protein or peptide comprising agrin, a variant thereof or a fragment" means human or other mammalin or avian agrin, a fusion protein of such agrin with one or more, e.g. two or three, other peptides or proteins, in particular with a marker protein, e.g. with green fluorescent protein (GFP), with enhanced green fluorescent protein (EGFP) or also with a short marker peptide such as 8× histidine, an agrin variant wherein one or more, for example one, two, three or four, amino acids are deleted or replaced by different amino acids, a fusion protein of such an agrin variant as defined hereinbefore, or an agrin fragment comprising at least 6, in particular at least 8 amino acids of agrin, for example between 8 and 20 or between 400 and 600 amino acids of agrin, either as such or fused to a marker peptide or protein, and wherein the agrin variant or agrin fragment retains the cleavage site α, cleavage site β or both cleavage sites, in particular wherein the agrin fragment comprises the consensus sequence of the cleavage site α and/or cleavage site β as defined hereinbelow. Such "a protein or peptide comprising agrin, a variant thereof or a fragment" may contain further non-peptidic markers, e.g. for spectroscopic detection, as described hereinafter.

In particular, the method for measuring the catalytic activity of neurotrypsin relates to the use of the full-length human or other mammalian or avian neurotrypsin or the protease domain of neurotrypsin, and the full-length agrin or a fragment thereof, e.g. an engineered variant of membrane-bound agrin, for example agrin-EGFP of sequence SEQ ID NO:9, or for example the C-terminal agrin fragment, agrin-C45, of sequence SEQ ID NO:12.

Particularly preferred reaction conditions for measuring the catalytic activity of neurotrypsin are a buffer solution between pH 7 and pH 8 comprising $Ca^{2+}$ ions, for example a buffer solution of 10 mM MOPS, pH 7.5, or also 50-100 mM Tris-HCl, including 100-200 mM NaCl, 1-20 mM $CaCl_2$, in particular 2-5 mM $CaCl_2$, and optionally up to 0.5% polyethylene glycol, e.g. polyethylene glycol 6000, a reaction temperature between 20° C. and 40° C., for example around 25° C., and a reaction time between 1 and 48 hours, for example between 2 and 16 hours, e.g. around 3 hours. Neurotrypsin is used at a concentration that results in the cleavage of approximately 80% of the substrate within 3 hours. Preferred concentration of neurotrypsin is 0.1 to 10 nM, for example around 1 nM, and agrin in a concentration of 10 times to 5'000 times the concentration of neurotrypsin, e.g. 1'000 times such a concentration.

The length of the agrin-derived substrate can be varied from full-length agrin to a small peptide including at least one of the cleavage sites for neurotrypsin. Neurotrypsin cleaves agrin at two distinct evolutionarily conserved sites (Example 25). The consensus amino acid sequence comprising the first cleavage site (cleavage site α) is . . . P-P/A-IN-E-R-A-S/T-C-Y . . . (SEQ ID NO: 14), where the cleavage occurs between the R995 and A996 residues. The consensus amino acid sequence comprising the second cleavage site (cleavage site β) is . . . G/A-L/I/T-I/V-E-K-S-V/A-G . . . (SEQ ID NO: 15), where the cleavage occurs between the K1754 and S1755 residue.

The assay measures the release of a protein or peptide fragment from the substrate protein or peptide. If a peptide containing the amino acid sequence immediately N-terminal of the cleavage site α or β is used in conjunction with a chromogenic or fluorogenic substrate that is covalently linked to the peptide's C-terminal, the released chromogenic or fluorogenic substrate is measured. Short peptide substrates spanning over cleavage site α or β can also be used for measuring the proteolytic activity of neurotrypsin by the fluorescence quenching method (Le Bonniec, B. F. et al., Biochemistry 35: 7114-7122, 1996).

The detection of the cleavage products of protein substrates containing the cleavage sites α or β are performed with specific antibodies against the one or the other of the fragments generated by the proteolytic activity of neurotrypsin (Examples 22 and 23) or by coupling a fluorescent, chromogenic, or other tag to one or the other end of agrin or agrin fragment. For the detection of the cleavage products any method for the detection of proteins or peptides and their cleavage products is applicable. For example, the cleavage of full-length agrin and larger fragments of agrin (larger than approximately 10 kDa) is detected by SDS-PAGE followed by Western blotting or direct visualization in the gel using fluorescently or otherwise tagged proteins by the appearance of smaller fragments at the expense of the initial substrate. Smaller fragments of agrin (smaller than approximately 10 kDa) may be immobilized by their binding to a plastic surface or a bead, and cleavage visualized by the solubilization of a fragment that may either be detected by specific recognition by an antibody or by means of a fluorescent or otherwise detectable compound (Patel, D. et al., BioTechniques 31: 1194-1203, 2001).

One agrin-derived substrate to study cleavage of agrin by neurotrypsin at the cleavage site α is, for example, an engineered agrin-EGFP based on the transmembrane form of agrin. A soluble form of this molecule is generated by replacement of the transmembrane part by the secretion signal peptide sequence of human calsyntenin-1 and an 8× histidine tag. This protein can be purified from cell culture supernatants using metal-affinity chromatography. To delete the cleavage site β, the LG3 domain and the loop connecting the EGF4 domain and the LG3 domain containing the β-site are replaced by an EGFP or another protein domain connected by a short linker (see Example 20). Useful working concentrations for a neurotrypsin activity assay are from low nanomolar up to micromolar, for example 1 nM to 10 μM. This protein substrate and its cleavage products can be measured using Western blot assays using antibodies detecting the C-terminal cleavage product of agrin that is generated by cleavage at the cleavage site α (Example 22) or in ELISA assays by binding the protein via its N-terminal poly-histidine tag and monitoring the release of the C-terminal fragment via appropriate antibodies (Example 22) or measuring the released fluorescence of the EGFP moiety in a plate reader.

Another agrin-derived substrate for monitoring the proteolytic activity of neurotrypsin consists of a C-terminal agrin fragment of about 45 kDa comprising the cleavage site β of agrin. It consists of the LG2-EGF4 and LG3 domains of agrin containing the cleavage site β between the EGF4 and LG3 domains. To produce the protein in secreted form in cell cultures the human calsyntenin-1 secretion signal peptide is fused N-terminally, followed by a 8× histidine tag for ease of purification and binding to Ni-NTA plates. For detection and further purification a C-terminal Streptag II can be added. This substrate (see Example 21) is suitable for neurotrypsin activity measurements from low nanomolar to micromolar concentrations, for example 1 nM to 10 μM. Neurotrypsin activity can be monitored by staining the uncleaved substrate and the cleavage products by protein dyes, such as Coomassie blue or Sypro Ruby, or via Western blot detecting the C-terminus of the cleavage product using StrepTactin (IBA, Göttingen) or an appropriate antibody detecting the LG3 domain (see Example 23). Further constructs containing a C-terminal EGFP or a SNAP-Tag (Covalys) labelled with appropriate dyes or other signal-giving proteins can be used for high throughput assays in plate tests detecting the release of fluorescence upon cleavage by neurotrypsin, by binding the N-terminal part of the protein substrate to a Ni-NTA plate or Ni-NTA beads (see for example: Patel, D., BioTechniques 31: 1194-1203, 2001).

Chromogenic proteolytic substrates typically contain natural or artificial peptides composed of 3 to 5 natural or artificial amino acids. They may be N-terminally protected to reduce undesired degradation by aminopeptidases. On their C-termini they are modified so that a chromogenic or fluorogenic group is released upon cleavage of the amide bond. Detection depends on the type of leaving group and may range from the UV- to the visible region of light. Others produce a fluorescent signal. Most commonly used groups are the p-nitroaniline (pNA), which absorbs light of the wavelength of 405 nm (Nall, T. A. et al., J. Biol. Chem. 279: 48535-48542, 2004), and the fluorogenic 7-amino-4-methylcoumarin (AMC) with an excitation wavelength of 342 nm and an emission wavelength of 440 nm (Niyomrattanakit, P. et al., J. Virol., 78: 13708-13716, 2004). For detection of neurotrypsin activity a short tripeptide IER-pNA can be used at a concentration of 20-50 μM in assay buffer (150 mM NaCl, 5 mM $CaCl_2$, 0.1% PEG 6000, 20 mM MOPS, pH 7.5) at 25 to 37° C. Upon cleavage by neurotrypsin at a concentration of 1-5 nM, an increase of the signal intensity at 410 nm can be followed in a spectrophotometer.

FRET substrates are widely used in proteolytic assays because they offer a homogenous and sensitive assay easily adaptable for high-throughput screening (HTS). The method is particularly useful for screening libraries of organic compounds for competitive neurotrypsin inhibitors in a high-throughput-assay setup. In a FRET assay the peptide substrate is synthesized with two fluorophores, a fluorescent donor (ortho-aminobenzoic acid, "Abz") and a quenching acceptor (ethylene-diamine-2,4-dinitrophenyl, "ED-DNP"). The distance between these two groups has been selected so that upon light excitation, the donor (Abz) fluorescence energy is significantly quenched by the acceptor (ED-DNP) through a quantum mechanical phenomenon known as fluorescence resonance energy transfer (FRET), which occurs without the emission of light. Upon cleavage of the substrate peptide by the protease, the fluorophore is separated from the quenching group, restoring the full fluorescence yield of the donor. The increase in fluorescence by a factor of 7-100 is linearly related to the rate of proteolysis (Le Bonniec, B. F. et al., Biochemistry 35: 7114-7122, 1996).

One agrin-based FRET substrate useful to detect neurotrypsin activity is a peptide (SEQ ID NO: 13) with the amino acid sequence Abz-PIERASCY-ED-DNP, containing the neurotrypsin recognition site α of agrin (Jerini AG, Berlin, Germany). The putative cleavage site is located between amino acids four (R) and five (A) of the substrate. Upon cleavage of the peptide at a concentration of 1-40 μM by 1-10 nM neurotrypsin in assay buffer (150 mM NaCl, 5 mM $CaCl_2$, 0.1% PEG 6000, 20 mM MOPS, pH 7.5) at 25 to 37° C., activity can be detected spectrofluorometrically due to increasing signal intensity at an excitation wavelength of 320 nm and an emission wavelength of 430 nm in a fluorescence spectrophotometer.

Another FRET substrate is based on two fluorescent proteins, cyan-fluorescent protein (CFP) and enhanced yellow-fluorescent protein (EYFP). In between the two proteins a 16 amino acid linker, containing the neurotrypsin recognition sequence a (PIERASCY) (SEQ ID NO: 13) and two 4 amino acid spacers, one downstream and one upstream of the neurotrypsin recognition sequence, is introduced (linker sequence: GAGSPIERASCYGSST) (SEQ ID NO: 16). Alternatively, the corresponding amino acid sequence flanking the cleavage site β can also be used. Cleavage of the sensitive linker sequence by neurotrypsin separates the two fluorophores and results in a loss of the energy transfer. Data collection is performed in assay buffer (150 mM NaCl, 5 mM $CaCl_2$, 0.1% PEG 6000, 20 mM MOPS, pH 7.5) at 25 to 37° C. using 1-10 nM neurotrypsin and 0.1-1 μM substrate. Thus, hydrolysis of the substrate can be evaluated by the measurement of increasing fluorescence intensity of the donor (Em. 485 nm) and simultaneously decreasing fluorescence of the acceptor (Em. 528 nm) after excitation at 400-450 nm (Pollock, B. A. et al., Trends in Cell Biol. 9: 57-60, 1999).

The invention further relates to a method for determining whether a compound is a neurotrypsin inhibitor, characterized in that the compound is incubated together with neurotrypsin, in particular human neurotrypsin, a variant thereof or a fragment comprising the protease domain and with a protein or peptide comprising agrin, a variant thereof or a fragment comprising the cleavage site α or the cleavage site β of agrin, in an aqueous buffer solution, and the amount of cleavage of agrin is measured.

In particular, the method for determining whether a compound is a neurotrypsin inhibitor relates to the use of the full-length human neurotrypsin or the protease domain of human neurotrypsin, and the full-length agrin or a fragment thereof, e.g. an engineered variant of membrane-bound agrin, for example agrin-EGFP of sequence SEQ ID NO:9, or, for example the C-terminal agrin fragment, agrin-C45, of sequence SEQ ID NO:12. Inhibitors of neurotrypsin are found using the assay for the proteolytic activity of neurotrypsin (Example 24) and testing for the activity-reducing effect of a candidate compound (Examples 26 and 27). To measure the proteolytic activity of neurotrypsin, purified neurotrypsin (Examples 18 and 19) and purified agrin, or a purified fragment of agrin containing at least one cleavage site (Example 20 and 21), are incubated together with the compound to be tested under appropriate conditions. At the end of the incubation period, the cleavage products that have been generated by the proteolytic activity of neurotrypsin are measured. By comparison of the amount of generated cleavage product in reactions containing potential neurotrypsin inhibitors with a control reaction without the addition of organic compounds the inhibitory effects of the compounds are determined (Example 27). The dose-dependence of the inhibitory activity of a compound found as an inhibitor of neurotrypsin is determined as described in Example 28. The specificity of a compound found as an inhibitor of neurotrypsin is investigated by testing for its inhibitory activity on other serine proteases as described in Example 29.

Particularly preferred reaction conditions for determining whether a compound is a neurotrypsin inhibitor are a buffer solution around pH 7 comprising $Ca^{2+}$ ions, for example 100-200 mM NaCl, 5-20 mM $CaCl_2$, 20 mM MOPS, pH 7.5, and optionally up to 0.5% polyethylene glycol, a reaction temperature between 20° C. and 40° C., for example around 25° C., and a reaction time between 1 and 48 hours, for example 3 hours. Preferred concentration of neurotrypsin is 0.1 to 10 nM, for example around 1 nM, and agrin in a concentration of 10 times to 5'000 times the concentration of neurotrypsin, e.g. 1'000 times such a concentration. The compound to be tested is added in increasing concentrations, preferably in concentrations between 0.001 and 500 µM. DMSO may be added up to 30% to improve the solubility of the compounds to be tested.

The invention further relates to methods of detecting the activity of neurotrypsin and the inhibitory effect on neurotrypsin of small-molecule organic compounds in high-throughput screening systems (HTS) in a way that neurotrypsin, a variant thereof or a fragment comprising the protease domain of neurotrypsin and a protein or peptide comprising agrin, a variant thereof or a fragment comprising the sequence for the cleavage site α or the cleavage site β of agrin, or any other protein comprising a sequence homologous to the sequence of the cleavage site α or β of agrin, are incubated together in an aqueous buffer solution and the amount of cleavage product is measured in processes suitable for HTS.

In particular, all methods described above referring to methods for measuring the catalytic activity of neurotrypsin could also be used in multiplate assays or dot blots with appropriate methods for a HTS readout.

Small peptide substrates containing either the cleavage site α or the cleavage site β with C-terminal chromogenic or fluorogenic leaving groups can easily be read out in a multiplate reader by measuring the increase of fluorescence or absorption at appropriate wavelengths. This method can also be applied to protein substrates with N-terminal or C-terminal affinity tags, for example a poly-histidine tag or a Streptag II or protein tags, and C-terminally or N-terminally fused signal-giving proteins or protein domains, for example fluorescent proteins, or proteins which can be labelled with chromophores or fluorophores, or even enzymes catalyzing chromogenic or fluorogenic reactions like β-galactosidase or others, by fixing one part of the protein to the surface of the well and detecting the generation of fluorescence or absorption or enzymatic activity in the supernatant of the well at appropriate wavelengths. The generation of cleavage products upon neurotrypsin activity in an HTS may also be monitored in ELISA applications by detecting the amount of cleavage products in the supernatant of wells coated with protein substrates suitable for neurotrypsin cleavage or the residual amount of uncleaved substrate with appropriate antibodies linked to signal giving enzymes or groups (Gutierrez, O. A. et al., Anal. Biochem. 307: 18-24, 2002).

The invention further relates to other non-plate assays suitable for HTS-like detection of cleavage products of small-peptide substrates or protein substrates of any described kind with methods like HPLC (Betageri, R. et al., J. Biochem. Biophys. Methods 27: 191-197, 1993), FPLC, mass spectrometry (Mathur, S. et al., J. Biomol. Screen. 8: 136-148, 2003), SELDI (Cyphergen) or other related applications.

Additionally, the invention relates to inhibitors of neurotrypsin found by this method, in particular to compounds of formula

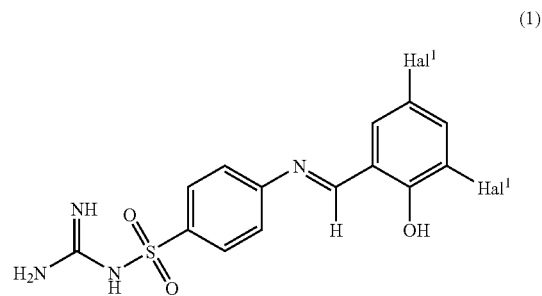

(1)

wherein $Hal^1$ and $Hal^2$ are, independently of each other, fluorine, chlorine or bromine; in particular bromine; and pharmaceutically acceptable addition salts thereof. Preferred are also compounds wherein on of $Hal^1$ and $Hal^2$ is bromine and the other one is chlorine or fluorine, and pharmaceutically acceptable addition salts thereof. Particularly preferred are pharmaceutically acceptable addition salts of a compound of formula (1) wherein $Hal^1$ and $Hal^2$ are bromine.

Such pharmaceutically acceptable salts are formed, for example, with organic or inorganic acids. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

Compounds of formula (1) are prepared by methods known in the art, for example by condensation of an amine of formula (2) or a precursor thereof, wherein the amidine function is in protected form or present as a functional group easily transformed into an amidine function, with an aldehyde of formula (3), and the optional protection group is cleaved after the condensation reaction or the functional group is transformed into the amidine function.

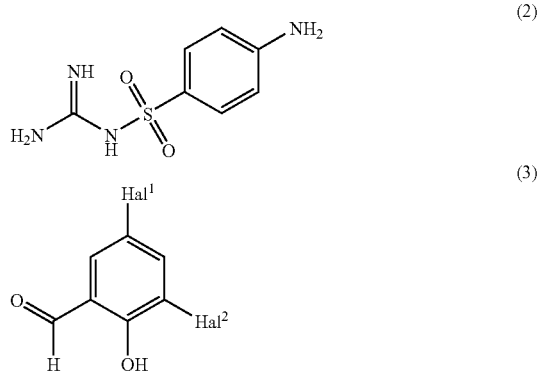

In particular, the invention relates to pharmaceutical compositions comprising compounds of formula (1) as described hereinbefore, and to the use of compounds of formula (1) as medicaments.

The present invention relates also to pharmaceutical compositions that comprise a compound of formula (1) as active ingredient and that can be used especially in the treatment of the diseases mentioned. Compositions for enteral administration, such as nasal, buccal, rectal or, especially, oral administration, and for parenteral administration, such as intravenous, intramuscular or subcutaneous administration, to warm-blooded animals, especially humans, are preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The pharmaceutical compositions comprise from approximately 1% to approximately 95% active ingredient, and are, for example, coated and uncoated tablets, ampoules, vials, suppositories, or capsules; or ointments, creams, pastes, foams, tinctures, drops, sprays, dispersions, etc. Examples are capsules containing from about 0.05 g to about 1.0 g active ingredient. The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene (20)sorbitan mono-oleate).

Suspensions in oil comprise as the oil component the vegetable, synthetic, or semi-synthetic oils customary for injection purposes.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methyl-cellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings known in the art.

Pharmaceutical compositions for oral administration also include hard capsules consisting of gelatin, and also soft, sealed capsules consisting of gelatin and a plasticizer, such as glycerol or sorbitol. Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

EXAMPLES

Example 1

Neurotrypsin is Strongly Expressed by Motoneurons of the Spinal Cord

The in situ hybridization pattern on transverse cryosections of the spinal cord of adult mice revealed a strong cellular expression of neurotrypsin mRNA in the gray matter (Gschwend, T. P., et al., Molec. Cell Neurosci. 9: 207-219, 1997). The strongest expression of neurotrypsin in the spinal cord was found in motoneurons in the ventral horn of the gray matter.

For immunohistochemical localization of neurotrypsin protein in the spinal cord antibodies against the catalytic domain of neurotrypsin were generated. To generate the antigen for immunization, the catalytic domain of human neurotrypsin, containing a His-tag at the C-terminus, was produced in E. coli, purified on a Ni-NTA column, and refolded. Portions of 50 µg were used for immunization of a goat (primary immunizations in complete Freund's adjuvans and booster injections in incomplete Freund's adjuvans). From the immune serum, IgG was isolated by affinity chromatography on immobilized protein G. Affinity-purified IgG was obtained by affinity chromatography on the immobilized proteolytic domain of neurotrypsin.

Adult (2 month old) mice were deeply anesthetized with sodium pentobarbital (80 mg/kg, Abbot) and perfused transcardially with 10 ml of 0.9% NaCl, followed by 150 ml of fixative containing 4% paraformaldehyde (Merck), 0.05% glutaraldehyde (Merck), and 0.2% picric acid (BDH) in 0.1 M phosphate buffer, pH 7.4 (PB). Coronal brain sections were cut on a vibrating microtome at 60 µm. To enhance the penetration of the immunoreagents, the sections were equilibrated in 30% sucrose in PB, rapidly frozen in liquid nitrogen and then thawed in PB and pretreated with 0.3% Triton-X100 for 10 min. After preincubation in 20% normal goat serum (NGS; Vector Labs, Servion, Switzerland) in 0.05 M Tris buffered saline (TBS; pH 7.4) for 45 min at room temperature (RT), the sections were incubated for 36-48 h at 4° C. with the primary antibody against neurotrypsin (1 µg/ml). For immuno-peroxidase light microscopy, the sections were incubated in biotinylated goat anti-rabbit IgG (1:200, Vector Labs) for 12 h at 4° C. followed by 3 h incubation in an avidin-biotin-peroxidase complex (Elite ABC; 1:100, Vector Labs) at RT. Antigenic sites were visualised by incubation in 3,3'-diaminobenzidine (Sigma; 0.05% in TBS, pH 7.6) in the presence of 0.004% $H_2O_2$. Sections were mounted on gelatinised slides, air dried, dehydrated, and coverslipped in Entelan (Merck).

The immunohistochemical staining pattern detected in this way on transverse sections of the spinal cord of adult mice revealed strong signals for the presence of neurotrypsin in the gray matter. The strongest expression level was found in the motoneurons of the ventral horn. Control sections treated with the same procedure, but under omission of the first or second antibody, did not show any staining.

In conclusion, these experiments clearly demonstrate that neurotrypsin is strongly expressed in the gray matter of the spinal cord. Particularly strong expression is found in the motoneurons, which are located in the ventral horn and innervate the skeletal muscles.

Example 2

Neurotrypsin Cleaves Agrin

The proteolytic effect of neurotrypsin versus agrin was tested by coexpression of the two proteins in HEK293T cells. A 2310 by KpnI-HindIII fragment comprising the coding sequence of mouse neurotrypsin was cloned into the eucaryotic expression vector pcDNA3.1(−) (Invitrogen) via KpnI and HindIII. A cDNA clone coding for rat agrin (Rupp, F. et al., Neuron 6: 811-823, 1991; GenBank Nr. M64780) consisting in the transmembrane isoform containing the splice variants Y4 and Z8 was inserted into the polylinker of pcDNA3 (Invitrogen) via KpnI and EcoRI. HEK293T cells were cultured in DMEM/10% FCS at 37° C. in humidified air with 10% $CO_2$. For transfection, cells were seeded in 3 ml DMEM/10% FCS onto glass cover slips placed into a 3 cm dish. The day after seeding, at a confluence of 40-60%, the cells were transiently transfected with cDNAs encoding neurotrypsin and agrin (5 µg DNA each) using calcium-phosphate precipitation. 4 h after transfections, the medium was carefully removed and replaced by 3 ml fresh DMEM/10% FCS.

The fate of agrin when coexpressed with neurotrypsin was analyzed by Western blotting. Fourty-eight h after transfection, the cells were washed with PBS and lysed by the addition of 250 µl buffer (20 mM Tris-HCl, pH 7.4, 150 mM NaCl, 1 mM EDTA, 1% Triton X-100, protease inhibitor cocktail). The extract was incubated at 4° C. for 20 min and then centrifuged for 20 min with 15000×g at 4° C. The supernatant was collected. After determination of protein concentration, the supernatant was mixed with 5× Laemmli loading buffer, boiled for 3 min, centrifuged and used for analysis. Proteins were separated by SDS-PAGE, using 7.5% acrylamide. After electrophoresis, proteins were transferred to a nitrocellulose membrane. Transfer quality was verified by Ponceau S staining. The membrane was then blocked with TBS containing 0.1% Tween-20 and 5% (w/v) blocking reagent (Amersham). All subsequent steps were done in TBS with 0.1% Tween-20. The membrane was incubated with the primary antibody (SZ177, 1:1000; AGR540, 1:1000; K-17, a polyclonal anti-agrin antibody (Santa Cruz), 1:1000) for 60 min. After extensive washing, the membrane was incubated with secondary peroxidase-coupled antibodies for 45 min. Detection was done with ChemiGlow (Alpha Innotech) according to the manufacturer's instruction. Images were taken with a Chemi-Imager (Alpha Innotech).

Agrin was clearly identified in detergent extracts of single transfectants (FIG. 2, lane 1). In extracts of double transfectants, agrin was strongly reduced (FIG. 2, lane 2). No agrin signal was found in cells transfected with empty vector. The production of neurotrypsin under all conditions was confirmed after reprobing the blot with anti-neurotrypsin antibodies. Analysis of the culture medium of these different conditions revealed that the immunoreactivity that was lost from the cell extract of the double transfected cells had been released into the supernatant medium. In 200 µl culture medium of double transfected HEK293T cells a 100-kDa band was detected with the anti-agrin antibody (FIG. 2, lane 3). This signal was not found in medium from single transfectants (FIG. 2, lane 4). Likewise, no signal was detected in medium of HEK293T cells transfected with agrin and catalytically inactive neurotrypsin.

In summary, the results indicate that (1) neurotrypsin produced in HEK293T cells has catalytic activity, that (2) agrin, an extracellularly present component of the neuromuscular junction and the synapses of the central nervous system, can be cleaved by neurotrypsin-dependent proteolysis, and (3) that this neurotrypsin-dependent cleavage leads to the formation of a truncated and a released form of agrin. The released part of agrin has an apparent molecular weight of approximately 100 kDa. Because the antibodies used for the detection of agrin were directed against epitopes in the C-terminal part of agrin, the solubilized fragment comprises the C-terminal side of agrin.

Example 3

Agrin Cleavage In Vivo Coincides with Expression of Neurotrypsin in the Spinal Cord During Neural Development To test for cleavage of agrin in vivo, spinal cord homogenates of developing and adult mice were analyzed by Western blot using specific antibodies for Nt and the C-terminal 100-kDa fragment of agrin. Tissue homogenates were prepared from the spinal cords of mice on postnatal days 4, 7, 9, 10, 15, and 25, as well as from 3, 6, and 12 months old mice. As demonstrated in FIG. 3, Nt is most strongly expressed in the first three postnatal weeks, with highest expression levels between days 7 and 10. Western blotting with antibodies versus the C-terminal moiety of agrin revealed a highly similar temporal pattern, indicating that agrin cleavage by neurotrypsin also occurs in vivo.

Example 4

Selective Overexpression of Neurotrypsin in Motoneurons Using Transgenic Mice Technology Neurotrypsin was overexpressed under the control of the promoter of the Thy-1 gene. The Thy-1 gene is expressed in the neurons of the nervous system of the mouse relatively late (postnatal day 4-10, depending on the location; Gordon, J. W. et al., Cell 50: 445-452, 1987). Therefore, the expression of neurotrypsin under the control of the Thy-1 promoter ensures that the earlier developmental stages are not perturbed by the presence of excessive amounts of neurotrypsin.

Neurotrypsin-overexpressing mice were generated with a conditional transgene that required activation. For this purpose, a removable transcriptional stop sequence flanked by loxP sites was introduced before the neurotrypsin cDNA. Thus, the stop sequence could be removed with the Cre recombinase/loxP recombination system (Sauer B. et al., Proc. Natl. Acad. Sci. (USA) 85: 5166-5170, 1988). The Cre (Cre-recombinase) protein is encoded by the E. coli bacteriophage P1 and efficiently promotes both intra- and intermolecular recombination of DNA. Recombination occurs at a specific site called loxP (Hamilton, D. L. and Abremski, K., J. Mol. Biol. 178: 481-486, 1984). This characteristic feature of the Cre recombinase allows deletion and insertion of specifically denoted strings of DNA between the loxP sequences. It can be used to generate specific functional mutations in vivo (Chen S. et al., Cell 51: 7-19, 1987).

Mice bearing the construct for conditional neurotrypsin-overexpression were crossed with heterozygous mice carrying Cre-recombinase DNA in the gene for the transcription factor HB9 in order to generate mice overexpressing active neurotrypsin in motoneurons. The HB9 promoter is active in vivo during motoneuron specification and, thus, all motoneurons express HB9-driven Cre-recombinase, resulting in the removal of the transcriptional stop sequence from the inactive transgene.

The transgenic mice were genotyped by PCR. The DNA for the PCR was extracted from the tail of the mice. The position of the PCR primers was chosen so that the detection of the native murine neurotrypsin gene was prevented. The 3'-primer corresponded to a DNA sequence inside the Thy-1 promoter and the 5'-primer to a sequence inside the neurotrypsin cDNA. This DNA fragment is unique to the neurotrypsin transgene. The primers for detection of the Cre insert were both equivalent to DNA sequences derived from inside the Cre gene, because Cre usually does not exist in mice. By this procedure, three mouse lines overexpressing the human neurotrypsin and four lines overexpressing the mouse neurotrypsin were raised. The expression of the transgene was verified at the mRNA level by Northern blotting and in situ hybridization and at the protein level by Western blotting. A typical overexpression was in the order of 2- to 10-fold.

The dependence of neurotrypsin-mediated alteration on its catalytic domain was verified by generating transgenic mice overexpressing a catalytically inactive form of neurotrypsin under the same, i.e. the Thy-1 promoter. Inactive neurotrypsin can readily be generated by mutating the essential active site serine 711 (corresponding to serine 195 of chymotrypsin) to an alanine. Because in all serine proteases, the active site serine is involved in a covalent intermediate of the proteolytic reaction, its mutation results in a complete loss of catalytic function. The transgenic mice overexpressing the inactive form of neurotrypsin were healthy and did not exhibit any abnormalities.

Example 5

Transgenic Overexpression of Neurotrypsin Enhances Agrin Cleavage In Vivo

Tissue homogenates were prepared from the spinal cords of adult mice overexpressing either human neurotrypsin (hNt) or mouse neurotrypsin (mNt). These mice were obtained by crossing mice with the inactive transgenes (lines 497, 489, and 533 for mNt and lines 493 and 494 for hNt) with mice expressing Cre recombinase under the control of the motoneuron-specific HB9 promoter. Wild-type mice were used for controls. The spinal cord homogenates were subjected to SDS-PAGE and Western blotting. The Western blots were probed with antibodies versus hNt and mNt, as well as the C-terminal 100-kDa fragment of agrin. As shown in FIG. 4, the C-terminal 100-kDa fragment of agrin was strongly increased in the transgenic mice overexpressing neurotrypsin. The increase of the amount of the C-terminal 100-kDa fragment of agrin was in a good correlation with the level of overexpression in the different transgenic mouse lines. Human and mouse Nt showed the same proteolytic effect on agrin. These results indicate that neurotrypsin cleaves agrin in vivo in a concentration-dependent manner.

Example 6

Transgenic Overexpression of Neurotrypsin in Motoneurons Results in the Removal of Agrin from the Nmj within Hours to Days The effect of transgenic overexpression of neurotrypsin (Nt) in spinal motoneurons was investigated by immunohistological analyses of the neuromuscular junction (NMJ). Of particular interest was the first postnatal week, because it is known that the Thy-1 promoter used for driving the expression of the transgenic Nt becomes active during the first postnatal week (with some variation depending on the location). For this analysis, the diaphragm was used because the surface localization of the NMJs makes this muscle an excellent model for such comparative analyses. The visualization of agrin was performed by immunohistological staining using affinity-purified antibodies against the C-terminal 100-kDa fragment of agrin. As demonstrated in FIG. 5, agrin immunoreactivity at P0, a time point before the onset of transgene activation, is identical in wild-type and transgenic mice (FIG. 5: P0). In both cases, agrin immunoreactivity clearly matches the α-Btx signals of the NMJs shown in FIG. 6 for the same muscles. At P8, a striking reduction of agrin immunoreactivity is found at the NMJs of the diaphragm of Nt-overexpressing mice, when compared with wild-type mice (FIG. 5: P8). The endplate band, which is densely populated with agrin-positive NMJs in age-matched wild-type mice, shows only very few large NMJ-like agrin-positive structures. The agrin immunoreactivity of P4 mice shows a transition stage, characteristic by a mixed pattern with structures of variable size, varying from well conserved NMJs to small structures reflecting residuals of NMJs (FIG. 5: P4). Most agrin immunoreactive structures in FIG. 5 were exactly matched to the α-Btx positive structures of FIG. 6. However, in a substantial proportion of the transition state synapses of Nt-overexpressing mice, the ratio between the agrin signal and the α-Btx signal was smaller than at P0 (See Example 7).

These results demonstrate that neurotrypsin cleaves agrin in vivo at the NMJ and that the C-terminal moiety of agrin disappears from the NMJ within hours to days after neurotrypsin-dependent cleavage. This is particularly remarkable because the C-terminal moiety contains the domain responsible for the pro-synaptic activity of agrin.

Example 7

Neurotrypsin-Induced Removal of Agrin from the NMJ Results in the Dispersal of the NMJ within Hours to Days The effect of neurotrypsin (Nt) overexpression in motoneurons and subsequent removal of agrin from the NMJs was investigated by visualization of the postsynaptic apparatus. The visualization of the postsynaptic apparatus was performed by staining the acetylcholine receptors with fluorescent α-bungarotoxin (α-Btx). As shown in FIG. 6 in a comparison of Nt overexpressing (Nt) mice with wild-type (wt) mice, the postsynaptic apparatus is well established at birth (postnatal day 0, P0). At the end of the first postnatal week (P8), most postsynaptic apparatuses of the NMJs have virtually disappeared in the Nt overexpressing mice. Only a few residual NMJs can be made out within the so-called endplate band, were the NMJs are found at high density in the wild-type mice. On the 4$^{th}$ day of postnatal development (P4), a heterogeneous pattern composed of a mixture of still well-shaped NMJs and partially dissolved NMJs is found. The reduction in the density of NMJs within the endplate band of the transgenic mice when compared with the wild-type mice suggests that a portion of the NMJs has already completely disappeared in the Nt-overexpressing mice at this stage.

Transition-state NMJs are characteristic by the absence or at least a strongly reduced presence of agrin within the α-Btx-decorated structure. Such transition-state NMJs are exclusively found in Nt-overexpressing mice. In wild-type mice, in contrast to the Nt-overexpressing mice, the immunostaining for agrin is always well matched with the α-Btx staining of the acetylcholine receptors of the postsynaptic apparatus.

In summary, these experiments demonstrate that an elevated expression of Nt in motoneurons results in the dispersal of already established NMJs. The dispersal of the NMJs follows the transgenic upregulation Nt with short delay (estimated to last between hours and a few days). The analysis of transition state synapses demonstrates that the dispersal of the postsynaptic apparatus follows the cleavage of agrin and the removal of the C-terminal 100-kDa fragment of agrin from the NMJ. This indicates that Nt plays an anti-synaptic role at the NMJ by counteracting the pro-synaptic role of agrin. If the anti-synaptic function is excessively enhanced by a strong overexpression of neurotrypsin in motoneurons, the pro-synaptic agent agrin is overwhelmed and, thus, the NMJ is disassembled.

Example 8

Adult Mice with Elevated Expression of Neurotrypsin in Spinal Cord Motoneurons Exhibit a Pronounced Neuromuscular Phenotype with Diminished Muscular Strength Transgenic mice that overexpress Nt in motoneurons were generated by crossing mice bearing the conditional Nt transgene (described in Example 4) with mice expressing Cre recombinase under the control of the HB9 promoter. The HB9 promoter drives the overexpression of Cre recombinase in spinal motoneurons and, thus, activates the inactive Thy1-Nt transgene in motoneurons by excision of the transcriptional stop segment. The double transgenic mice derived from such crossings exhibit a motor phenotype. They walk slowly, with an insecure gait and little steps. They also show a considerably reduced muscular strength.

In summary, the overexpression of Nt in motoneurons results in a peripheral motor phenotype, characterized mainly by a reduced strength of skeletal muscles.

Example 9

Neuromuscular Junctions of Adult Mice with Elevated Expression of Neurotrypsin Exhibit a Pronounced Fragmentation of the Pre- and Postsynaptic Apparatus The comparison neuromuscular junctions of transgenic mice overexpressing Nt and wild-type mice of the same age (young adult) revealed a marked fragmentation of the NMJs of the Nt-overexpressing mice. The typical Prezel structure of the NMJs that develops in the first three postnatal weeks in wild-type mice is not found in Nt-overexpressing mice (FIGS. 7 D, E, and F). Although the NMJs of Nt-overexpressing mice occupy approximately the same area on the surface of their target muscle fibers, their postsynaptic as well as their presynaptic contacts do not form a contiguous structure, but are broken up into numerous small contact sites. The fragmentation of the NMJs observerd in Nt-overexpressing mice is also found in NMJs of aged people suffering from sarcopenia, a form of muscle atrophy found in humans at old age.

In summary, elevated production of neurotrypsin in motoneurons results in a fragmentation of the NMJs that closely resembles the fragmentation of the NMJs that are reported from studies of humans suffering from sarcopenia.

Example 10

Muscles of Adult Mice with Elevated Expression of Neurotrypsin have a Significantly Reduced Number of Muscle Fibers The muscles of young adult mice overexpressing Nt in motoneurons were analyzed with regard to the number of muscle fibers. Individual muscles, e.g. the soleus muscle, were isolated and tissue sections were made perpendicular to the long axis of the muscle through the middle segment of the muscle. Section were stained with Hematoxyline-Eosine and the fibers were counted. FIG. 8 shows a comparison of a soleus muscle of a wild-type mouse (FIG. 8 A) and a Nt-overexpressing mouse (FIG. 8 B). The muscle of the Nt-overexpressing mouse is considerably thinner than the muscle of the wild-type mouse and has a markedly smaller number of muscle fiber. The number of muscle fibers were counted in the soleus muscle of four different lines of Nt-overexpressing mice (Table 1).

TABLE 1

| | Number of muscle fibers | | |
|---|---|---|---|
| Mouse Line | Muscle A | Muscle B | Ratio 2xTG/WT |
| 493xHb9-Cre 2xTG | 669/701 | 584/612 | 77% |
| 493xHb9-Cre WT | 752/905 | 803/863 | |
| 494xHb9-Cre 2xTG | 509/502 | 356/396 | 52% |
| 494xHb9-Cre WT | 826/827 | 822/901 | |
| 497xHb9-Cre 2xTG | 720/607 | 651/688 | 82% |
| 497xHb9-Cre WT | 774/764 | 883/822 | |
| 498xHb9-Cre 2xTG | 846/829 | 650/571 | 78% |
| 498xHb9-Cre WT | 906/893 | 946/989 | |

The results reveal a marked reduction of the fiber number in the Nt-overexpressing mice of all four independent transgenic mouse lines.

In summary, the quantification of the fiber numbers in mice demonstrate that elevated Nt in motoneurons results in a significant reduction of the number of muscle fibers.

Example 11

Overexpression of Neurotrypsin in CNS Neurons of Transgenic Mice

According to the procedure of Example 4 transgenic mice for conditional overexpression of neurotrypsin were obtained. These mice were crossed with heterozygous mice expressing the Cre-recombinase under the control of the cytomegalovirus (CMV) promoter. The CMV promoter is continuously active in vivo and, therefore, Cre-recombinase promotes recombination at the two loxP sequences at all times. This procedure removes the transcriptional stop sequence from the inactive transgene and allows transcription of the neurotrypsin cDNA. Genotyping by PCR and Southern blot hybridization was done as in Example 4.

Similarly, transgenic mice overexpressing a catalytically inactive form of neurotrypsin under the Thy-1 promoter were generated by mutating the active site serine (Serine 711) of neurotrypsin to an alanine.

Example 12

Increased Levels of Neurotrypsin in CNS Neurons Result in a Reduction in the Number of Synapses To quantify the number of synapses per volume of tissue of a synapse-rich region, and to measure the size parameters of the synapses (including the area of the presynaptic axon terminals, the area of the postsynaptic spines, and the length of the synapses (as measured by the length of the apposition of the pre- and postsynaptic membranes), two independent lines of neurotrypsin-overexpressing mice (Nt491/cre and Nt494/cre) and several lines of control mice (wild-type mice, CMV-Cre mice, and the transgenic parental lines bearing the inactive neurotrypsin transgene Nt491-inact.Nt and Nt494-inact.Nt) were investigated. The mice were deeply anesthetized at the age of 28 days with metiofane (Schering-Plough) and perfused through the heart with 0.9% sodium chloride followed by fixative consisting of 2% paraformaldehyde, and 1% glutaraldehyde in 0.1 M phosphate buffer (PB), pH 7.4. The brains were removed from the scull and sectioned into 100 µm thick serial sections with a vibratome. The sections were postfixed in 1% osmium tetroxide in PB, treated with 2% uranyl acetate, dehydrated in ethanol and propylene oxide and embedded in Durcupan ACM resin (Fluka). For electron microscopic analysis sections containing the CA1 region of the hippocampus at the anteriocaudal level Bregma—2 mm and mediolaterally 1.5 mm were ultrasectioned. The synaptic sampling procedure consisted of 15 to 23 EM samples of the neuropil of the stratum radiatum of the hippocampal CA1 region from three noncontiguous areas with at least 50 µm distance between each other at an initial magnification of 27,500-fold. The electron micrographs were printed at a final magnification of 80,000-fold which represented 90 to 135 µm² of tissue. A synapse was defined as two apposed thickened membranes of a presynaptic and postsynaptic profile, with the presynaptic profile containing at least three synaptic vesicles in close association with the differentiated membranes. The synapses were classified into axodendritic and axospinous synapses according to ultrastructural criteria. Dendritic shafts were identified by their size and the presence of mitochondria and microtubules. Dendritic spines were of smaller diameter, lacked mitochondria and microtubules, and occasionally contained a spine apparatus. The axodendritic synapses comprised an insignificantly small proportion in all samples and therefore were excluded from further statistical estimation. All axospinous synapses were counted in each micrograph with exception of those touching the exclusion lines. The cross-section areas of axonal terminals and postsynaptic spines and lengths of synaptic junctions of all axospinous synapses were measured directly from the prints using a magnetic tablet (Kurta) and the Macstereology 2.8 (Ranfurly Microsystems) analysis program. The numerical density of synapses were obtained using size-frequency method and formula $N_V = N_A/d$ (were $N_A$ is a number of synaptic profiles per unit area and d is the average length of synaptic junctions; DeFelipe, J., et al., Cereb. Cortex 9:722-732, 1999).

The number of synapses per mm³ was counted. The results are shown in FIG. 9. The number of synapses per mm³ was significantly reduced in neurotrypsin-overexpressing mice. In contrast, the numbers of synapses in control mice, i.e. the parental lines used for the generation of the double transgenic (DTG) neurotrypsin-overexpressing mice (491-inact.Nt, 494-inact.Nt, and CMV-Cre) were the same as in wild-type mice. Therefore, these results indicate a significant reduction of synapses in the neurotrypsin-overexpressing mice.

Example 13

Increased Levels of Neurotrypsin in CNS Neurons Result in a Reduced Number of Dendritic Spines (Postsynaptic Elements)

Parasagittal hippocampal slices (300 µm) of 17 to 32 days old neurotrypsin-overexpressing and wild-type mice were cut using a stainless steel razor blade (Electron Microscopy Sciences) and transferred to an incubation chamber filled with 34° C. warm and oxygenated ACSF and incubated for one hour, in order to provide sufficient time for the brain tissue to recover from the cutting injury. Thereafter, the slices were kept at room temperature until used later in the experiments.

For whole-cell patch clamp recording the slices were put into a standard submerged chamber also superfused with ACSF. Individual neurons were visualized with an Axioscope microscope (Zeiss) fit with differential interference contrast optics using infrared illumination. The experimental chamber was maintained at 35-36° C., which is near physiological temperature. The flow rate of ACSF through the chamber was between one and two ml per minute. The ASCF was oxygenated by oxycarbon prior to entering the recording chamber. The recordings were done using a whole-cell recording pipette (3-5 MΩ), pulled on the Flaming/Brown puller and filled with the same solution as in the chamber. For morphological reconstruction neurons were injected with a solution of 115 mM KOH, 20 mM K-gluconate, 10 mM KCl, 10 mM HEPES (Good's buffer), 10 mM phospho-kreatine, 4 mM ATP-Mg, 0.3 mM GTP, and 13.4 mM biocytin. Each slice with a biocytin-labeled CA1 pyramidal cell was placed between two pieces of Millipore filter paper to keep it flat during fixation for 2-3 hours at room temperature by immersion into fixative containing 1% glutaraldehyde, 2% paraformaldehyde and approx. 0.2% picric acid in 0.1 M phosphate buffer (PB), pH 7.4. Slices were stored in 0.5% paraformaldehyde in PB at 4° C. After several washes in PB, the slices were treated with 2% hydrogen peroxide for 15 min and then pre-incubated in 20% normal goat serum in 0.05 M Tris-buffered saline (pH 7.4) containing 0.5% Triton X-100 (TBST) for 30 min at room temperature. Subsequently they were subjected to overnight incubation in Vectastain Elite ABC (avidin-biotin-peroxidase) reagent (1:100; Vector Labs) in TBST at 4° C. Following 5 times 15 min washes in TBST and Tris buffer (TB, pH 7.6), biocytin containing cells were visualized by incubation in 3,3'-diaminobenzidine (0.05% in TB) in the presence of 0.0048% $H_2O_2$. The reaction was stopped by several washes in TB. Sections were mounted on slides and coverslipped in Mowiol (Hoechst).

As demonstrated in FIG. 10, CA1 hippocampal pyramidal neurons of transgenic mice overexpressing Nt in CNS neurons exhibited a marked reduction of both the number and the size of dendritic spines. Because dendritic spines represent the postsynaptic side of synapses in these neurons, these results confirm a reduction in synapse number in neurotrypsin-overexpressing mice by an independent method.

Example 14

Agrin Cleavage In Vivo Occurs Also in the CNS and Coincides with Expression of Neurotrypsin in CNS Neurons To test for cleavage of agrin in the CNS in vivo, brain homogenates of developing and adult mice were analyzed by Western blot using specific antibodies for Nt and the C-terminal 100-kDa fragment of agrin. Tissue homogenates were prepared from the spinal cords of mice on postnatal days 4, 7, 9, 10, 15, and 25, as well as from 3, 6, and 12 months old mice. It was found that Nt is most strongly expressed in the first three postnatal weeks, with highest expression levels between days 7 and 10. Western blotting with antibodies versus the C-terminal moiety of agrin revealed a highly similar temporal pattern, indicating that agrin cleavage by neurotrypsin also occurs in vivo in the CNS.

Example 15

Transgenic Overexpression of Neurotrypsin in CNS Neurons Enhances Agrin Cleavage In Vivo Tissue homogenates were prepared from the brains of adult mice overexpressing either human neurotrypsin (hNt) or mouse neurotrypsin (mNt) generated by crossing mice bearing the inactive transgenes (lines 497, 498, and 533 for mNt and lines 493 and 494 for hNt) with mice expressing Cre recombinase under the control of the CMV promoter and, for comparison, wild-type mice. The brain homogenates were subjected to SDS-PAGE and Western blotting. The Western blots were probed with antibodies versus hNt and mNt, as well as the C-terminal 100-kDa fragment of agrin. It was found that the C-terminal 100-kDa fragment of agrin is strongly increased in the transgenic mice overexpressing neurotrypsin. The increase in the amount of the C-terminal 100-kDa fragment of agrin was in good correlation with the level of overexpression in the different transgenic mouse lines. Human and mouse Nt showed the same proteolytic effect on agrin. These results indicate that Nt cleaves agrin in the CNS in vivo in a concentration-dependent manner.

Example 16

Production of Recombinant Neurotrypsin

Neurotrypsin is a secreted multi-domain protein with a length of 875 amino acids and an estimated size of 97 kDa for human neurotrypsin and 761 amino acids and a size of 85 kDa for mouse neurotrypsin (FIGS. 1, A and B). The expression of this serine protease as an active protein is dependent upon proper folding and very likely on post-translational modifications, e.g. N-glycosylation which has been proposed for 2 sites in the case of the human and 3 sites for the mouse protein (Gschwend, T. P. et al., Mol. Cell. Neurosci. 9: 207-219, 1997; Proba, K. et al., Biochim. Biophys. Acta 1396: 143-147, 1998). In addition, neurotrypsin contains a signal peptide directing the protein to the endoplasmatic reticulum from where it is secreted. Neurotrypsin is not an integral membrane protein since it is lacking a transmembrane domain as determined by a hydrophobicity plot (Kyte, J. and Doolittle, R. F., J. Mol. Biol. 157: 105-132, 1982). The zymogen activation site of neurotrypsin shows high similarity to the one of tPA (tissue-type plasminogen activator; Tate, K. M. et al., Biochemistry 26: 338-343, 1987). Cleavage at this site by a protease leads to the two fragments, one containing the non-catalytic domains with an apparent molecular weight of approx. 55 kDa (for mouse neurotrypsin) or approx. 67 kDa (for human neurotrypsin) and one containing only the protease domain with approx. 30 kDa. Production of neurotrypsin in myeloma cells. For the stable transfection of myeloma cells the coding regions of mouse and human neurotrypsin were inserted into a specially designed vector (Traunecker et al., Biotechnol. 9: 109-113, 1991). Expression by this vector is driven by an Ig κ promoter and enhancer. The 3' end of the transcript of interest is spliced onto an exon encoding the Ig κ constant domain in order to mimic stable Ig transcripts. The vector contains a histidinol dehydrogenase gene that allows the selection of stable transfectants in the presence of L-histidinol. L-histidinol is a precursor of L-histamine and an inhibitor of protein synthesis. The vector has been stably transfected into the mouse myeloma cell line J558L (ECACC #88032902; European Collection of Cell Cultures) for the production of recombinant neurotrypsin. Other suitable lines for stable transfection by protoplast fusion or electroporation include mouse P3-X63Ag8.653, mouse Sp2/0-Ag14, mouse NSO, and rat YB2/0 (Gillies et al., Biotechnology 7: 799-804, 1989; Nakatani et al., Biotechnology 7: 805-810, 1989; Bebbington et al., Biotechnology 10: 169-175, 1992; Shitara et al., J. Immunol. Meth. 167: 271-278, 1994).

Stable transfection of J558L cells can be achieved using electroporation. A total of $10^6$ cells are mixed with 10 µg linearized or supercoiled vector in PBS in a 1 cm cuvette. Electroporation is performed using a Bio-Rad Gene Pulser (Bio-Rad Chemical Division) with a pulse of 960 pF and 170-230 V. Cells are transferred to 50 ml DMEM containing 10% FCS and plated on five 96 well plates by adding 100 µl/well using a multi-channel pipetter.

Liposome transfection of J558L cells is performed using lipofectamine and PLUS reagent (Invitrogen). $1 \times 10^7$ myeloma cells are centrifuged at 500×g for 3 min and washed once with serum-free DMEM medium. After a second centrifugation the cells are resuspended in 3 ml serum-free DMEM medium. For transfection 40 µg of plasmid DNA encoding neurotrypsin are mixed with 320 µl serum-free DMEM and 80 µl PLUS reagent (Invitrogen). After incubation of 15 min at RT the pre-mixed 60 µl lipofectamine transfection reagent with 340 µl serum-free DMEM is added to the reaction and incubated 15 min at RT. One ml of serum-free DMEM are added to the DNA-liposome mix before addition to the J558L cells. Transfected cells are incubated in a 6 cm tissue culture dish at 37° C. with 10% $CO_2$. After 4 h the cells are diluted in 45 ml DMEM containing 10% FCS and plated in five 96 well plates by adding 100 µl/well using a multi-channel pipetter. For the preparation of protoplasts the glycerol stock of an E. coli strain 803 clone containing the mammalian expression vector is streaked on a LB agar/ampicillin plate and grown overnight at 37° C. (strain 803 available from ATCC #35581). One single colony is inoculated in 2 ml pre-warmed (37° C.) LB media containing 50 µg/ml ampicillin. After 4 h shaking at 250 rpm and 37° C. 100 µl of the culture are transferred to 100 ml fresh medium. After the culture reached an optical density of about 0.6 (OD at 600 nm), chloramphenicol is added to a final concentration of 120 µg/ml and grown overnight at 250 rpm and 37° C. Plasmids carrying the colE1 origin of replication can be amplified in the presence of chloramphenicol (Hershfield et al., Proc. Natl. Acad. Sci. USA 71, 4355-3459, 1974). The overnight culture is centrifuged at 2500×g for 10 min at 4° C. The pellet is resuspended in 2.5 ml ice-cold 20% (w/v) sucrose in 50 mM Tris-HCl, pH 8.0. 500 µl ice-cold 1 mg/ml lysozyme in 250 mM Tris-HCl, pH 8.0, are added before incubation on ice for 5 min. After addition of 1 ml ice-cold 250 mM EDTA, pH 8.0, and incubation on ice for 5 min, 1 ml ice-cold 50 mM Tris-HCl, pH 8.0, is added and the protoplast preparation incubated at RT for 10 min. During this incubation period, formation of spherical protoplasts from the usually rod-shaped bacteria can be observed using a microscope with 1000× magnification. About 90% protoplasts should be formed at the end of the incubation period. To the protoplast suspension 20 ml DMEM supplemented with 10% (w/v) sucrose, 10 mM $MgCl_2$ and 40 µl 10 mg/ml DNaseI are added. After incubation for 15 min at RT the protoplast preparation is spun at 2500×g for 30 min at RT. In the meantime myeloma cells J558L are prepared for the fusion. Myeloma cells were grown in DMEM supplemented with 10% (v/v) FCS and should reach a high cell density of approximately $1\times10^6$ cells/ml on the day of transfection. Per protoplast fusion $5\times10^6$ cells are spun down at 500×g for 10 min at RT. The cells are resuspended in 5 ml pre-warmed DMEM (37° C.) and slowly layered on top of the protoplast pellet after the last centrifugation. To mix protoplasts and myeloma cells the tube is spun at 500×g for 10 min at RT. After removal of the supernatant the cells are mixed by flicking the tube. For the fusion 2 ml PEG 1500 in DMEM supplemented with 10% DMSO are added and the pellet is resuspended by pipetting up and down several times. About 1 to 2 min after addition of the PEG solution, 10 ml pre-warmed DMEM supplemented with 10% (v/v) FCS (37° C.) are added. The cells are centrifuged at 500×g for 10 min at RT. The supernatant is removed by aspiration and the pellet resuspended in 50 ml pre-warmed DMEM supplemented with 10% (v/v) FCS and 100 µl 50 mg/ml kanamycin. Finally, the cells are plated in five 96-well tissue culture plates by adding 100 µl/well using a multi-channel pipetter.

For selection of the transfected cells L-histidinol is added in a final concentration of 5 mM after 48 h. Only transfected myeloma cells will survive the treatment with L-histidinol. Clones are visible about 12 to 14 days after the selection had started. In average 40 to 50 clones are obtained per protoplast fusion and liposome transfection. All clones were analyzed for expression by Western blot with neurotrypsin-specific antibodies. While the majority of myeloma cell clones expressed no or only moderate amounts of neurotrypsin, a small percentage of 5-10% revealed a very high expression level. Clones with high expression level were subcloned over three rounds of single cell dilutions to ensure the stability of neurotrypsin expression. From the stably expressing clones cell extracts and supernatants were collected and separated on a 10% SDS PAGE. Proteins were transferred to a nitrocellulose membrane. Detection of neurotrypsin was performed with either a neurotrypsin-specific antibody recognizing the non-catalytic segment and a secondary goat-anti-rabbit antibody coupled to peroxidase or a neurotrypsin-specific antibody recognizing the protease domain and a rabbit-anti-goat antibody coupled to peroxidase. While full-length neurotrypsin is predominately detected in the cell extract, the 65 kDa band corresponding to the non-catalytic fragment and the 30 kDa band of the proteolytic domain are detected in the supernatant.

Example 17

Intermediate-Scale Production of Neurotrypsin

The source of neurotrypsin used was a conditioned cell-culture supernatant resulting from the cultivation of a neurotrypsin-expressing myeloma cell line. These cells have been adapted to growth in a serum-free medium (Stoll, T. S. et al., J. Biotechnol. 45: 111-123, 1996; Ackermann, G. E. and Fent, K., Marine Environmental Research 46: 363-367, 1998) in the TechnoMouse fermenter (Integra Biosciences). Starting from a medium composed of DMEM (Gibco, No. 41966-029) containing 2 mM glutamine and 10% FCS, the cells were stepwise adapted to grow in this medium with 1% FCS. Adaptation was performed in 24 well plates and the medium was exchanged approximately every second day. When cells reached confluency, they were split into another well. Throughout the whole procedure, cells were kept at a density near confluency. Adapted cells growing well in DMEM containing 1% FCS were then transferred to the serum-free, but protein-containing medium HL-1 (Bio-Whittacker, No. 77201) supplemented with 0.5% FCS. In HL-1 medium the cells were then stepwise adapted to grow in HL-1 medium only (without FCS). To adapt the cells to the protein-free medium TurboDoma (Cell Culture Technologies GmbH, Zurich, No. THP) the HL-1 medium was stepwise exchanged by TurboDoma. The adaptation steps from HL-1 to TurboDoma medium were performed analogously to the reduction of FCS.

Example 18

Purification of Full-Length Neurotrypsin 20 liters of supernatant from the preceding example were filtered through a 1 µm polygard CR optical filter (Millipore) and concentrated to 5 liters by cross-flow filtration (SKAN AG).

Heparin-affinity chromatography. NaCl was added to the concentrated supernatant to reach a final concentration of 0.3 M prior to loading it on a 120 ml heparin column (Heparin sepharose 6 Fast Flow XK 50/20 column; Amersham Biosciences). The column was equilibrated with 20 mM MOPS, 300 mM NaCl, pH 7.2 (buffer A). The sample was loaded onto the column at a flow rate of 1 ml/min at 20° C. on an Aekta Purifier (Amersham Biosciences Europe GmbH). The column was washed with four column volumes (CV) of buffer A. Bound proteins were eluted by a gradient in 20 mM MOPS, 1 M NaCl, pH 7.2 (buffer B). The gradient was as follows: In 1 CV from 0% B to 43% B, 3 CV at 43% B, in 2 CV from 43 to 100% B, and 3 CV at 100% B. Neurotrypsin starts to elute at a concentration of 450 mM sodium chloride. The elution fractions containing neurotrypsin (full-length protein and protease domain) were pooled, aliquoted and stored at −20° C.

Hydrophobic-interaction chromatography was carried out on a butyl-substituted polymer matrix (Butyl sepharose 4 Fast Flow, Amersham Biosciences Europe GmbH). To adjust the sample to the loading conditions, dry sodium chloride was slowly added under constant stirring. After adjusting the sodium chloride concentration the sample was centrifuged in a Sorvall RC-5B centrifuge for 30 min at 12000 rpm in an SS34 rotor at 4° C. The supernatant was loaded at a flow rate of 1 ml/min onto an equilibrated 25 ml column (20 mM MOPS, 1.5 M sodium chloride, pH 7.2) on an Aekta Purifier chromatography system (Amersham Biosciences Europe GmbH) at 20° C. Bound proteins were eluted applying a linear gradient of decreasing concentration of sodium chloride (1.5 M-0.05 M) in 20 mM MOPS, pH 7.2, at 1 ml/min. Full-length neurotrypsin starts to elute at a concentration of 900 mM sodium chloride. The full-length protein containing elution fractions were pooled, and stored at −20° C.

Immobilized-metal-affinity (IMAC) chromatography. $Cu^{2+}$ ions were coupled to sepharose (Chelating Sepharose Fast Flow, Amersham Biosciences Europe GmbH) according to the manufacturer's instructions. Solid sodium chloride was added to the sample to increase the concentration to over 0.5 M. The sample was subsequently centrifuged in a Sorvall RC-5B centrifuge for 30 min at 12000 rpm in an SS34 rotor at 29° C. The resulting supernatant was applied to the 1 ml copper sepharose column at a flow rate of 1 ml/min on an Ettan chromatography system (Amersham Biosciences Europe GmbH) at 4° C. Proteins were eluted with an imidazol gradient from 10-250 mM in 20 mM MOPS, 0.5 M sodium chloride, pH 7.2. The gradient was as follows: In 15 CV from 0% B to 10% B, in 5 CV from 10% B to 100% B, and 10 CV at 100% B. Full-length neurotrypsin starts to elute at 150 mM imidazol. The full-length neurotrypsin containing fractions were pooled and stored at 4° C.

Ion-exchange chromatography. For ion-exchange chromatography the sample was diluted 2.5 times to a final sodium chloride concentration of 0.2 M, and centrifuged in a Sorvall RC-5B centrifuge for 30 min at 12000 rpm in a SS34 rotor at 4° C. The clear supernatant was applied at a flow rate of 0.1 ml/min on a MonoS PC 1.6/5 column (Amersham Biosciences Europe GmbH) equilibrated with 20 mM MOPS, 200 mM NaCl, pH 7.2. Bound proteins were eluted by a linear gradient of sodium chloride (0.05 M-1 M). Full-length neurotrypsin starts to elute at 300 mM sodium chloride. The protease domain containing fractions were pooled and stored at 20° C.

In this way full-length neurotrypsin is produced in electrophoreticly pure form. FIG. 11 shows purified full-length neurotrypsin, as visualized by Silver staining on an SDS-PAGE gel (A), and as visualized by immunostaining using a neurotrypsin-specific antibody on a Western blot (B).

Example 19

Purification of the Protease Domain of Neurotrypsin

The fractions from the heparin affinity chromatography of the preceding example containing full-length protein and protease domain were subjected to hydrophobic-interaction chromatography as above. The supernatant of the centrifuged solution was loaded at a flow rate of 1 ml/min onto an equilibrated 12 ml column (20 mM MOPS, 1.75 M sodium chloride, pH 7.2). Bound proteins were eluted applying a linear gradient of decreasing concentration of sodium chloride (1.75 M-0.05 M) in 20 mM MOPS, pH 7.2, at 1 ml/min. The protease domain starts to elute at a concentration of 1 M sodium chloride. The protease domain containing fractions were pooled and stored at −20° C.

IMAC (Immobilized-metal-affinity chromatography) was performed as for full-length Nt. Ion-exchange chromatography was performed as for full-length Nt.

In this way, the isolated catalytic domain of neurotrypsin is produced in electrophoreticly pure form.

Example 20

Cloning, Expression, and Purification of an Engineered Agrin Protein Suitable as a Substrate Containing the Cleavage Site α, but not the Cleavage Site β

The pcDNA-Agrin SN Y4Z19 codes for the membrane bound agrin form. First, a secreted, soluble agrin variant was constructed using the primers 5'-AAAGTTAACAAACCTG-GAAT CCACTTCACACCAGC-3' (SEQ ID NO:1) introducing a HpaI site and 5'-AAAAGCGGCC GCTCATTTTTC-GAACTGCGGGTGGCTCCAGGGAGTGGGGCAGGGTCTTAG-3' (SEQ ID NO:2) introducing a NotI site. The resulting PCR product was cut with HpaI and NotI and cloned into a pEAK8 vector containing the coding sequence for human calsyntenin-1 cut with the same restriction endonucleases. Previously, an additional HpaI site in the vector was removed using the quick change strategy (Stratagene). The resulting construct codes for a secreted agrin with the signal sequence of human calsyntenin-1 which is cleaved off during translation. Based on this construct a N-terminal 8×His tag was added by cloning the PCR product with the primers 5'-AAAAGTTAAC-CATCACCATCATCACCAT CACCATAAACCTG-GAATCCACTTCACACCAG-3' (SEQ ID NO:3) and 5'-TTTATCATGA CACAGTCGTTTTCATAG-3' (SEQ ID NO:4) using the HpaI and BspHI sites in the agrin gene. In a third step the LG3 domain at the C-terminus was replaced by EGFP in a SOE PCR with the primers 5'-GCTGGATATCAA-CAATCAGCAG-3' (SEQ ID NO:5) and 5'-GGT GAA-CAGCTCCTCGCCCTTGCTCACCATG-GAGCCAACTAGCCCCTGTTCGCAGTGC-3'(SEQ ID NO:6) with the construct described before as template and 5'-GGTGAACAGCTC CTCGCCCTTGCTCACCATG-GAGCCAACTAGCCCCTGTTCGCAGTGC-3' (SEQ ID NO: 7) and 5'-GGCTGCGGCCGCTCATTTTTCGAACT-GCGGGTGGCTCCAGTTATCTAGATC CGGTGGATC-3' (SEQ ID NO:8) with pEGFP as template. The resulting PCR fragments were combined in the SOE PCR and cloned via EcoRV and NotI site in the identically cut vector. The resulting secreted protein has the sequence SEQ ID NO:9.

HEK 293T cells were transfected with the engineered agrin-EGFP construct and grown in DMEM medium supplemented with 10% FCS and cultured for 6 h. The medium was exchanged to DMEM without FCS and incubated for 50 h at 37° C. Two hundred ml supernatant were centrifuged (4° C., 30 min GS3, 5000 rpm) to get rid of cells and insoluble material. The cleared solution was dialysed two times after a 1:25 dilution against 50 mM Tris-HCl, 150 mM NaCl, 0.1% PEG 6000, pH 8.0, at 4° C. overnight. After filtration (0.45 μm pore size) the solution was subjected to further purification by chromatography.

IMAC chromatography. After equilibration with 5 CV of 50 mM Tris-HCl, 150 mM NaCl, pH 8.0 the protein sample was loaded at 10 ml/min. The column was washed with 10 CV of 50 mM Tris-HCl, 150 mM NaCl, pH 8.0. For elution a gradient from 0 to 500 mM imidazole in washing buffer within 25 CV was used. Agrin-EGFP eluted at 20-50 mM imidazole. Fractions containing the desired protein as determined by Western blotting and SDS-PAGE were pooled and diluted 1:125, and dialyzed against 20 mM Tris-HCl, 150 mM NaCl, 0.1% PEG 6000, pH 8.0, at 4° C. overnight.

Anion-exchange chromatography. After loading the dialysate, the 8 ml POROS HQ20 column was washed with 2 CV of 20 mM Tris-HCl, 150 mM NaCl, pH 8.0. Elution was with a gradient of 150-2000 mM sodium chloride in washing buffer. Agrin-EGFP eluted at a sodium chloride concentration of about 900-1100 mM. Fractions containing the desired protein as determined by Western blotting and SDS-PAGE were pooled, diluted 1:25, and dialyzed against 20 mM Tris-HCl, 150 mM NaCl, 0.1% PEG 6000, pH 8.0 at 4° C. overnight. The resulting neurotrypsin was 90% pure and suitable for in vitro activity assays. The protein was frozen in liquid nitrogen and stored at −20° C.

The agrin-EGFP fusion protein generated this way contains the cleavage site α, but not the cleavage site β. Agrin-EGFP has a molecular mass higher than 250 kDa. Cleavage of the agrin-EGFP fusion protein by neurotrypsin generates a C-terminal fragment of approximately 150 kDa. FIG. 12 shows purified agrin-EGFP fusion protein, as visualized by Silver staining on an SDS-PAGE gel (A), and as visualized by immunostaining using an antibody against the C-terminal half of agrin (Example 22) on a Western blot (B). Note that EGFP is not essential for the described application, but rather represents a place holder. Replacing EGFP by another protein or using full-length agrin that is mutated at the cleavage site β are equivalent alternatives to the described product.

Example 21

Cloning, expression, and purification of a small C-terminal agrin fragment (agrin-C45) suitable as a substrate containing the cleavage site 6, but not the cleavage site α

Using the primers 5'-GCGAGTTAACCACCATCACCAT-CACCATCACCATGGAAGCC TGGCTGACTTTAATG-GCTTCTCCTACC-3' (SEQ ID NO:10) introducing a HpaI site (HisBNterm) and 5'-ACCTGCGGCCGCTCATTTTTC-GAACTGCGGGTGGCTCCAGCCAG AGCCAGAGC-CGGGAGTGGGGCAGGGTCTTAGCTC-3' (SEQ ID NO:11) introducing a NotI site (BStreplink) and pcDNA3.1-AgrinY0Z0 as template a DNA fragment was amplified coding for the last two LG domains and the last EGF like domain of agrin. Using this strategy, DNA sequences which encode an N-terminal 8×His tag and a C-terminal Strep tag were inserted. The resulting PCR product was cleaved with the restriction enzymes NotI and HpaI (boldface in the primer sequences) and cloned into pEAK8 vector containing the coding sequence for the signal peptide of human calsyntenin-1 cut with the same restriction enzymes. The resulting construct pEAK8-C45agrin contains the coding region of the signal sequence of human calsyntenin-1 as a secretion signal for C45agrin. Cloning was performed in E. coli as well as amplification of the plasmid. For expression HEK 293T cells were transfected using the calcium phosphate method. During expression in HEK 293T cells the signal peptide is cleaved off. The resulting secreted protein has the sequence (SEQ ID NO:12).

HEK 293T cells were cultivated to 80% confluency in 7×500 cm² culture plates (CORNING) with 100 ml DMEM medium (GIBCO) supplemented with 10% FCS each. For transfection 35 ml of 500 mM $CaCl_2$ and 35 ml of HBS buffer (50 mM HEPES, 140 mM NaCl, 1.5 mM $Na_2HPO_4$, pH 7.1) were equilibrated to RT. Two mg pEAK8-agrin-C45 DNA were added to the $CaCl_2$ solution and mixed with the HBS buffer. The transfection mixture was incubated at RT for 30 min. For transfection of 500 cm² HEK cells 10 ml of the transfection mixture were added dropwise to the culture and incubated for 4 h at 37° C. in the incubator at 37° C. The transfection mixture was then removed by washing once with PBS and addition of DMEM medium without FCS. After 60 h the conditioned medium was harvested and filtered using a Steritop 0.22 μm filter (MILLIPORE). The supernatant was directly submitted to IMAC purification using a Ni-NTA column (8 ml POROS) on a BioCAD perfusion chromatography system (Perseptive Biosystems) after adjusting the pH of the solution to pH 8.5 with 1 M Tris buffer pH 8.5. The conditioned medium was loaded with a flow rate of 10 ml/min, the column was washed with 20 CV of 100 mM Tris-HCl, 150 mM NaCl, pH 8.0. For elution a linear gradient from 0 to 1 M imidazole in washing buffer for 10 CV was used. Fractions containing the pure agrin-C45 fragment were pooled and the buffer was exchanged with a NAP 25 column (Pharmacia) to 100 mM Tris-HCl, 150 mM NaCl, 10 mM $CaCl_2$, 0.1% PEG 6000, pH 8.0. The purified protein was frozen in liquid nitrogen and stored at −20° C. The agrin fragment purified with this procedure is suitable as a substrate for neurotrypsin.

The agrin-C45 fragment generated this way contains the cleavage site β, but not the cleavage site α. Agrin-C45 has a molecular mass of approximately 45 kDa. Cleavage of the agrin-C45 protein by neurotrypsin generates an N-terminal fragment of approximately 23 kDa and a C-terminal fragment of approximately 22 kDa. FIG. 13 shows purified agrin-C45 protein, as visualized by Silver staining on an SDS-PAGE gel (A), and as visualized by staining its C-terminal Strep-tag using StrepTactin on a Western blot (B).

Example 22

Generation of a Polyclonal Antibody Against the C-Terminal Half of Rat Agrin

HEK 293T cells were grown to 80% confluency in 16×150 cm² tissue culture flasks. Each flask was used to inoculate 4×500 cm² plates. The 500 cm² plates contained 80 ml of culture medium and were coated with poly-L-lysine. The cells grew to 60-80% confluency within two days. Cells were transfected with the calcium phosphate method, with 1 μg of each pcDNA-agrinY4Z8 and pcDNA-hNT per ml of culture medium (DMEM/10% FCS). The medium was changed to DMEM without FCS the next morning. Cells grew for 4 days at 37° C./10% $CO_2$. The supernatant was harvested, centrifuged for 30 min at 3000 rpm at 4° C. and filtrated (0.45 μm pore size) at RT. The pH of the filtrate was set to 7.0 with 1 M HEPES buffer, but not exceeding a final concentration of 20 mM. It was loaded at 1 ml/min on a heparin column (17 ml heparin sepharose; capacity about 2 mg/ml gel matrix). The column was equilibrated with 5 CV of 20 mM HEPES, 80 mM NaCl, pH 7.5, and washed with 2CV of 20 mM HEPES, 80 mM NaCl, pH 7.5. Bound proteins were eluted by a linear gradient over 8 CV from 80-1000 mM NaCl in 20 mM HEPES, pH 7.5. The 100-kDa fragment eluted at about 400-600 mM NaCl. Fractions that contain the target protein were pooled, as monitored by SDS-PAGE and Western blot. The pooled fractions were dialyzed overnight at 4° C. against 20 mM HEPES, pH 7.5 1:100, so that the NaCl concentration was reduced to less than 5 mM. The dialysate was centrifuged for 30 min with 12000 rpm at 4° C. and loaded on a MonoQ column (7.8 ml HQ POROS column, capacity: 10-20 mg/ml matrix) equilibrated with 20 mM Tris, pH 8.0. Bound proteins were eluted with a linear gradient of 20 CV from 0-1000 mM NaCl in 20 mM Tris, pH 8.0. The 100-kDa fragment eluted at 100-200 mM NaCl. Fractions containing the target protein, as determined by SDS-PAGE and western blot were pooled.

Immunization. The purified protein was rapidly frozen by dripping into tube filled with liquid nitrogen and stored at −80° C. Rabbits were immunized using 50 µg portions of the protein with standard procedures. The resultant antibodies are suitable for the detection of full-length agrin, as well as agrin fragments containing the C-terminal part of agrin, specifically, agrin fragments containing the part of agrin situated between the cleavage sites α and β.

Example 23

Generation of a Polyclonal Antibody Against the LG3 Domain of Rat Agrin

HEK 293T cells were cultivated to 80% confluency in 5×500 cm² culture plates (CORNING) in 100 ml DMEM (GIBCO) supplemented with 10% FCS each. For transfection 25 ml of 500 mM $CaCl_2$ and 25 ml of HBS buffer (50 mM HEPES, 140 mM NaCl, 1.5 mM $Na_2HPO_4$, pH 7.1) were supplemented with 1.5 mg pEAK8-agrin-C45 DNA and 15 µg pcDNA-hNT DNA. The transfection mixture was incubated at RT for 45 min. For the transfection of 500 cm² HEK cells 10 ml of the transfection mixture were added dropwise to the culture and incubated for 4 h at 37° C. The transfection mixture was removed by washing three times with PBS and addition of DMEM medium without FCS. After 60 h the conditioned medium was harvested and filtered using a Steritop 0.22 µm filter (MILLIPORE). By cotransfecting the cells with pcDNA-hNT the agrin-C45 fragment is cleaved and the LG3 domain of rat agrin is released. To get rid of the major contaminants the conditioned medium was diluted 1:10 and dialyzed 5 times against 50 mM Tris-HCl, 50 mM NaCl, pH 8.0, and subjected to anion-exchange chromatography. The dialyzed medium was loaded at 10 ml/min on a 4 ml MonoQ column (self packed with Uno Sphere MonoQ material from BioRAD, 2×4 cm) connected to a BioCAD chromatography system (Perseptive Biosystems). The column was washed with 20 CV 50 mM Tris-HCl, 50 mM NaCl, pH 8.0. A gradient from 50 mM NaCl to 2000 mM NaCl in 50 mM Tris-HCl, pH 8.0, was used for elution. (This first step can optionally be replaced by a metal-affinity chromatography using a $Ni^{2+}$-chelated sepharose column.) The desired proteins were found in the flow through fraction and directly subjected to affinity chromatography using a 10 ml StrepTactin column previously equilibrated with 50 mM Tris-HCl, 150 mM NaCl, pH 8.0. After binding of the proteins at gravity flow the column was washed with 10 CV equilibration buffer. Elution was performed using 6 times 0.5 CV of equilibration buffer supplemented with 2.5 mM desthiobiotin. The elution was analyzed using SDS-PAGE and fractions containing the agrin-C45 fragment and LG3 domain were concentrated using Centriprep 10.000 concentrators (MILLIPORE) to a volume of 200 µl. The resulting concentrate was loaded onto a Superdex S75 gelfiltration column (Amersham Pharmacia, 1.6×30). Chromatography was performed with a flow rate of 0.3 ml/min using 50 mM Tris-HCl, 250 mM NaCl, pH 8.0. Elution was analyzed using SDS-PAGE, fractions containing the pure LG3 domain were pooled and frozen in liquid nitrogen.

Immunization. For generating polyclonal antibodies against the LG3 domain of agrin 50 µg fragment were used for immunizing rabbits. The resultant antibody is useful for the detection of full-length agrin, as well as for the detection of agrin fragments containing the LG3 domain of agrin.

Example 24

Assay for Proteolytic Activity of Neurotrypsin

Measuring neurotrypsin activity is performed in 150 mM NaCl, 5 mM $CaCl_2$, 0.1% PEG, and 20 mM MOPS, pH 7.5 in low protein-binding tubes (Eppendorf). Neurotrypsin activity measurements can also be performed using the same buffer including up to 30% DMSO. Human neurotrypsin is used in a concentration that results in the cleavage of approximately 80% of the substrate within 3 hours. As substrate, 0.1-1 µM agrin-EGFP or 0.1-3 µM agrin-C45 is used. The reaction mixture is incubated for 3 hours at 37° C. The reaction is then stopped by the addition of conventional SDS-PAGE sample buffer and heating at 70° C. for 5 min. The generated cleavage products are inspected after SDS-PAGE.

FIG. 14 gives an example for an assay using engineered agrin-EGFP as substrate and an antibody against the C-terminal moiety of agrin for detection of the C-terminal cleavage product of agrin-EGFP after SDS-PAGE and Western blotting. FIG. 15 gives an example for an assay using agrin-C45 as substrate. In this case, Streptactin (IBA GmbH) was used for the detection of the C-terminal cleavage product. Antibodies against the LG3 domain of agrin (generated as described in Example 23) may also be used for this purpose.

Alternatively, the SDS-PAGE gels are stained with conventional protein staining methods, such as silver staining (FIG. 15A), Coomassie brilliant blue, or, for quantification, with Sypro ruby (BioRad).

Example 25

Determination of the Cleavage Sites for Neurotrypsin within Agrin: Cleavage Sites α and β

To determine the exact cleavage position of the cleavage site α a membrane-bound agrin variant was coexpressed with human neurotrypsin in HEK293T cells. The resulting 100-kDa cleavage product appeared in the culture supernatant, was purified (see Example 22) and N-terminally sequenced by Edman degradation on a Procise 492 cLC Sequencer (Applied Biosystems). The determined sequence was ASXYNS-PLGXXSGDK (SEQ ID NO: 17) where X stands for cysteine residues. From this one can conclude that the cleavage occurs in the sequence stretch VVTHGPPIERASCYNS-PLGCCSDK (SEQ ID NO: 18) after the arginine at position 995.

Sequence alignments of several mammalian agrin sequences and the agrin sequence of the chicken (*Gallus gallus*) indicate a high degree of evolutionary conservation of the amino acids flanking the cleavage site α of agrin.

| Organism | Cleavage site α |
|---|---|
| Homo sapiens | PPVERASCY |
| Rattus norvegicus | PPIERASCY |
| Mus musculus | PPIERASCY |
| Gallus gallus | PAIERATCY |

These four sequences correspond, respectively, to SEQ ID NO: 19, SEQ ID NO: 20, SEQ ID NO: 21, and SEQ ID NO: 22.

The 5 amino acids on the N-terminal and the 4 amino acids on the C-terminal side of the cleavage site α of agrin (the cleavage site α of agrin is located between Arginine 995 and Alanine 996) define the consensus sequence P—P/A-I/V-E-R-A-S/T-C-Y (SEQ ID NO: 14) for the cleavage site α agrin.

For the determination of the exact cleavage position of the cleavage site β, agrin-C45 was coexpressed with human neurotrypsin in HEK293T cells. The resulting 21-kDa-cleavage product was purified (see Example 23) and N-terminally sequenced. The resulting sequence was SVGDLETLAF (SEQ ID NO: 23). This sequence is found in the stretch GLVEKSVGDLETLAFDGRT (SEQ ID NO: 24). From this one can conclude that agrin is cleaved by neurotrypsin after the lysine at position1754 between the EGF4 and LG3 domains.

Sequence alignments of several mammalian agrin sequences and the agrin sequence of the chicken (*Gallus gallus*) indicate a high degree of evolutionary conservation of the amino acids flanking the cleavage site β of agrin.

| Organism | Cleavage site β |
|---|---|
| *Homo sapiens* | GLVEKSAG |
| *Rattus norvegicus* | GLVEKSVG |
| *Mus musculus* | GIVEKSVG |
| *Gallus gallus* | ATIEKSAG |

These four sequences correspond, respectively, to SEQ ID NO: 25, SEQ ID NO: 26, SEQ ID NO: 27, and SEQ ID NO: 28.

The 5 amino acids on the N-terminal and the 4 amino acids on the C-terminal side of the cleavage site β of agrin (the cleavage site β of agrin is located between Lysine 1754 and Serine 1755) define the consensus sequence G/A-L/I/T-V/I-E-K-S-V/A-G (SEQ ID NO: 29) for the cleavage site β of agrin.

The results described above could be confirmed using the in vitro activity assays with purified human neurotrypsin and purified agrin substrate variants by transferring the resulting cleavage products onto a PVDF membrane and subsequent N-terminal sequencing.

In summary, agrin is cleaved by neurotrypsin at two positions. The first cleavage site (cleavage site α) is found at position R995-A996 (counting from accession number NP_786930, rat agrin), i.e. cleavage occurs C-terminally of the arginine in the sequence stretch PPIERASCY (SEQ ID NO: 20) of agrin of the rat (*Rattus norvegicus*) between the serine-threonine rich segment and the SEA domain. Comparison of mammalian and avian sequences flanking the cleavage site α of agrin define the consensus sequence P—P/A-I/V-E-R-A-S/T-C-Y (SEQ ID NO: 14) for the cleavage site α of agrin, where cleavage by neurotrypsin occurs C-terminally of the arginine (R) residue. The second cleavage (cleavage site β) locates at position K1754-51755 (counting from accession number NP_786930, rat agrin), i.e. cleavage occurs C-terminally of the lysine in the sequence context LVEKSVGD (SEQ ID NO: 30) in the segment connecting the EGF4 and LG3 domain of agrin. Comparison of mammalian and avian sequences flanking the cleavage site β of agrin define the consensus sequence G/A-L/I/T-V/I-E-K-S-V/A-G (SEQ ID NO: 29) for the cleavage site β of agrin, where cleavage by neurotrypsin occurs C-terminally of the Lysine (K) residue.

Example 26

Preparation of the Small-Molecule Compounds for Inhibition Assay

Compounds were dissolved in DMSO to a final concentration of 10 mM. For the assay the solution in DMSO was diluted with 10 mM MOPS, pH 7.5, to a concentration of 500 µM and 5% DMSO (1:20 dilution). Insoluble and precipitated material was removed by centrifugation (15 min, 16 krcf, RT). The cleared supernatant was used for the inhibition assay, as described in Example 27.

Example 27

Assay for Determining Inhibitory Activity of Small Molecule Compounds on Neurotrypsin The inhibitory activity of small-molecule compounds on the catalytic activity of neurotrypsin is measured in 150 mM NaCl, 5 mM $CaCl_2$, 5% DMSO, 0.1% PEG 6000, and 20 mM MOPS, pH 7.5 in 0.5 ml low protein-binding Eppendorf tubes in a total volume of 15 µl. Human or murine neurotrypsin or catalytically active truncated versions of neurotrypsin are used at a concentration that results in cleavage of 80% of the substrate within 3 hours. As substrate, engineered soluble agrin, for example 0.1-1 µM agrin-EGFP (Example 20) or 0.1-3 µM engineered agrin-C45 (Example 21), is used. Inhibitor solution in 10 mM MOPS, pH 7.5, containing 5% DMSO is added to a final concentration of either 25 or 150 µM. The reaction mixture is incubated for 3 h at 37° C. The 5% DMSO in the reaction mixture are required to maintain the solubility of the small inorganic compound inhibitors. The reaction is started by the addition of the substrate or the enzyme. At the end of the incubation period, the reaction is stopped by the addition of conventional SDS-PAGE sample buffer and heating at 70° C. for 5 min. The digested sample is separated by SDS-PAGE and inspected after visualization of the substrate.

One way of substrate visualization is Western blotting. For analysis, the proteins are transferred onto nitrocellulose membranes. From the intensities of the 150-kDa digestion fragment generated by the cleavage of agrin-EGFP or the 22-kDa digestion fragment generated by the cleavage of agrin-C45, the inhibitory activities of the screened small-molecule compounds on neurotrypsin are estimated. FIG. 16 shows a typical result of the inhibitor screening by Western blot analysis with an assay using agrin-EGFP as the substrate and an antibody against the C-terminal moiety of agrin for detection. The intensity of the 150-kDa fragments of agrin-EGFP generated by neurotrypsin-mediated cleavage in the presence of the putative inhibitory compounds (FIG. 16 A) are measured and the relative intensities are plotted (FIG. 16 B).

Compound No. 7 (identification number 1672-3440 from ChemDiv, San Diego, Calif., USA, $N^1$-amidino-$N^4$-(3,5-dibromosalicylidene)-sulfanilamide, IUPAC name: amino{[(4-{[(1E)-(3,5-dibromo-2-hydroxyphenyl)methylene]amino}phenyl)sulfonyl]amino}methaniminium) was found to have a significant inhibitory activity on neurotrypsin.

Alternatively, visualization and quantification of the digested sample is achieved directly in the gel by staining with conventional protein staining methods, such as silver staining, Coomassie brilliant blue staining, or, for quantification, by staining with Sypro ruby (BioRad).

Example 28

Dose Dependence of Inhibitory Compound No. 7, $N^1$-amidino-$N^4$-(3,5-dibromosalicylidene)-sulfanilamide Different concentrations of compound No. 7 from 0 to 200 µM were tested with the assay described in Example 27 with engineered agrin-EGFP as substrate. The generated product was detected by Western blot (FIG. 17A) and quantified (FIG. 17B). The half-maximum amount of product compared to the reaction without compound No. 7 was found at a concentration of approximately 60 µM, thus the $IC_{50}$ value for compound No. 7 is in the range of approximately 60 µM.

Example 29

Determining the Specificity of Neutrotrypsin Inhibition for Compound No. 7, $N^1$-amidino-$N^4$-(3,5-dibromosalicylidene)-sulfanilamide To check the specificity of a compound found to have an inhibitory effect on human neurotrypsin, standard enzyme kinetic measurements with a set of common serine proteases were performed. A standard photometric assay with commercially available proteases and para-nitroanilide-coupled small peptide substrates was used.

Proteases:
Factor Xa activated from bovine plasma (6.1 mg protein/ml; Sigma Aldrich Chemie GmbH, D-89552 Steinheim, Germany).
Trypsin from hog pancreas (16099 U/mg; Fluka Chemie AG, CH-9471 Buchs, Switzerland).
tPA: Actilyse (10 mg; Dr. Karl Thomae GmbH, Birkendorfer Straße 65, D-88397 Biberach, Germany).
Thrombin from bovine plasma (50 NIH/mg, Merck, D-64271 Darmstadt, Germany). Urokinase HS medac (100000 I.E.; medac Gesellschaft für klinische Spezialpräparate mbH, D-22880 Wedel, Germany).
Kallikrein from porcine pancreas (43 U/mg solid; Sigma Aldrich Chemie GmbH). Plasmin from human plasma (3.2 U/mg solid; Sigma Aldrich Chemie GmbH).

Substrates:
Bz-IEGR-pNA: S-2222, Chromogenix-Instrumentation Laboratory SpA, 1-20128 Milano, Italy.
Bz-FVR-pNA: N-Benzoyl-Phe-Val-Arg-p-nitroanilide HCl, Bachem AG, CH-4416 Bubendorf, Switzerland.
IPR-pNA: S-2288, Chromogenix-Instrumentation Laboratory SpA.
Bz-VGR-pNA: N-Benzoyl-Val-Gly-Arg-p-nitroanilide, Sigma Aldrich Chemie GmbH.
N-Tosyl-GPK-pNA: N-Tosyl-Gly-Pro-Lys-p-nitroanilide, #90178, Fluka Chemie AG.

Assay Conditions:
The assay was performed in 100 mM Tris-HCl, 150 mM NaCl, 1 mM $CaCl_2$, 5% DMSO, 0.1% PEG 6000, pH 8.0, with the appropriate amount of protease to measure initial velocities and varying amounts of peptide-p-nitroanilide substrates in a range smaller than 0.1 times $K_M$. For inhibition studies 100 µM compound No. 7 were used. Measurements were done at 25° C. in a Cary 50 Spectrophotometer (VARIAN). Initial velocities were determined using various substrate concentrations below 0.1 times $K_M$ to be in the range of direct dependency of the initial velocity from the substrate concentration. Initial velocities were plotted against substrate concentrations in the absence or the presence of the candidate inhibitor No. 7. The compound was used in a concentration of 100 µM.

| Protease | concentration | Substrate | concentration range |
| --- | --- | --- | --- |
| factor Xa | 10 nM | Bz-IEGR-pNA | 5-30 µM |
| trypsin | 2.8 nM | Bz-FVR-pNA | 1-5 µM |
| tPA | 212 nM | IPR-pNA | 10-100 µM |
| thrombin | 28.4 nM | Bz-FVR-pNA | 2-20 µM |
| urokinase | 285.7 I.E. | Bz-VGR-pNA | 5-280 µM |
| plasma kallikrein | 5 U | Bz-FVR-pNA | 20-240 µM |
| plasmin | 0.08 U | N-Tosyl-GPK-pNA | 3-15 µM |

None of the investigated enzymes showed a significant inhibition by compound No. 7 at a concentration of 100 µM. FIGS. 18-24 show the results of the enzyme kinetic measurements in the presence and the absence of compound No. 7 for factor Xa, trypsin, tPA, thrombin, urokinase, kallikrein, and plasmin.

---

The invention claimed is:

1. A method for determining whether a compound is a neurotrypsin inhibitor, said method comprising: incubating neurotrypsin or a variant or a fragment thereof, said variant or fragment comprising the protease domain of neurotrypsin, and agrin or a variant or a fragment thereof, said variant or fragment comprising the α- and/or the β-cleavage site of agrin, in the presence and in the absence of a test compound, and measuring the amount of cleavage of agrin in the presence or in the absence of the test compound, wherein a reduction in the amount of cleavage of agrin in the presence of the test compound compared to the cleavage of agrin in the absence of the test compound indicates that said test compound is a neurotrypsin inhibitor.

2. The method of claim 1, wherein neurotrypsin is human neurotrypsin.

3. The method of claim 1, wherein the agrin or variant or fragment thereof further comprises a marker protein or peptide.

4. The method of claim 1, wherein the agrin or variant or fragment thereof further comprises a non-peptidic marker for spectroscopic detection.

5. The method of claim 1, wherein the agrin fragment comprises at least 6 amino acids retaining the cleavage site α and/or cleavage site β.

6. The method of claim 1, wherein the agrin variant comprises at least 8 amino acids of the consensus sequence P—P/A-I/V-E-R-A-S/T-C-Y of the cleavage site α.

7. The method of claim 1, wherein the agrin variant comprises at least 8 amino acids of the consensus sequence G/A-L/I/T-I/V-E-K-S-V/A-G of the cleavage site β.

8. The method of claim 1, wherein the agrin fragment is a C-terminal agrin fragment C45 having the sequence of SEQ ID NO: 12.

9. A method for measuring the catalytic activity of neurotrypsin, said method comprising incubating neurotrypsin or a variant or fragment thereof, wherein said variant or fragment comprises the protease domain of neurotrypsin, with agrin or a variant or fragment thereof comprising the α- and/or the β-cleavage site of agrin and measuring the amount of cleavage of agrin, which indicates the catalytic activity of neurotrypsin.

10. The method of claim 9, wherein the agrin or variant or fragment thereof further comprises a marker protein or peptide.

11. The method of claim 9, wherein the agrin or variant or fragment thereof further comprises a non-peptidic marker for spectroscopic detection.

* * * * *

SEQUENCE LISTING

<160> NUMBER OF SEQ ID NOS: 30

<210> SEQ ID NO 1
<211> LENGTH: 35
<212> TYPE: DNA
<213> ORGANISM: Artificial sequence
<220> FEATURE:
<223> OTHER INFORMATION: Synthetic construct; primer for soluble agrin variant introducing HpaI site

<400> SEQUENCE: 1
aaagttaaca aacctggaat ccacttcaca ccagc                                 35

<210> SEQ ID NO 2
<211> LENGTH: 60
<212> TYPE: DNA

```
<213> ORGANISM: Artificial sequence
<220> FEATURE:
<223> OTHER INFORMATION: Synthetic construct; primer for soluble
      agrin variant introducing NotI site

<400> SEQUENCE: 2
aaaagcggcc gctcattttt cgaactgcgg gtggctccag ggagtggggc agggtcttag        60

<210> SEQ ID NO 3
<211> LENGTH: 59
<212> TYPE: DNA
<213> ORGANISM: Artificial sequence
<220> FEATURE:
<223> OTHER INFORMATION: Synthetic construct; forward primer for
      soluble agrin variant introducing 8xHis

<400> SEQUENCE: 3
aaaagttaac catcaccatc atcaccatca ccataaacct ggaatccact tcacaccag         59

<210> SEQ ID NO 4
<211> LENGTH: 27
<212> TYPE: DNA
<213> ORGANISM: Artificial sequence
<220> FEATURE:
<223> OTHER INFORMATION: Synthetic construct; reverse primer for
      soluble agrin variant

<400> SEQUENCE: 4
tttatcatga cacagtcgtt ttcatag                                            27

<210> SEQ ID NO 5
<211> LENGTH: 22
<212> TYPE: DNA
<213> ORGANISM: Artificial sequence
<220> FEATURE:
<223> OTHER INFORMATION: Synthetic construct; forward primer for
      soluble agrin variant replacing LG3

<400> SEQUENCE: 5
gctggatatc aacaatcagc ag                                                 22

<210> SEQ ID NO 6
<211> LENGTH: 58
<212> TYPE: DNA
<213> ORGANISM: Artificial sequence
<220> FEATURE:
<223> OTHER INFORMATION: Synthetic construct; reverse primer for
      soluble agrin variant replacing LG3

<400> SEQUENCE: 6
ggtgaacagc tcctcgccct tgctcaccat ggagccaact agcccctgtt cgcagtgc          58

<210> SEQ ID NO 7
<211> LENGTH: 58
<212> TYPE: DNA
<213> ORGANISM: Artificial sequence
<220> FEATURE:
<223> OTHER INFORMATION: Synthetic construct; forward primer for
      soluble agrin variant introducing EGFP

<400> SEQUENCE: 7
ggtgaacagc tcctcgccct tgctcaccat ggagccaact agcccctgtt cgcagtgc          58

<210> SEQ ID NO 8
<211> LENGTH: 60
<212> TYPE: DNA
<213> ORGANISM: Artificial sequence
```

```
<220> FEATURE:
<223> OTHER INFORMATION: Synthetic construct; reverse primer for
      soluble agrin variant introducing EGFP

<400> SEQUENCE: 8
ggctgcggcc gctcattttt cgaactgcgg gtggctccag ttatctagat ccggtggatc    60

<210> SEQ ID NO 9
<211> LENGTH: 1981
<212> TYPE: PRT
<213> ORGANISM: Artificial sequence
<220> FEATURE:
<223> OTHER INFORMATION: Synthetic construct; fusion protein of
      soluble agrin variant and EGFP

<400> SEQUENCE: 9
```

| | | | | | | | | | | | | | | | |
|---|---|---|---|---|---|---|---|---|---|---|---|---|---|---|---|
| Ala | Arg | Val | Asn | His | His | His | His | His | His | Lys | Pro | Gly | Ile |
| 1 | | | | 5 | | | | | 10 | | | | 15 |
| His | Phe | Thr | Pro | Ala | Pro | Pro | Thr | Pro | Pro | Asp | Val | Cys | Arg | Gly | Met |
| | | | 20 | | | | | 25 | | | | | 30 | | |
| Leu | Cys | Gly | Phe | Gly | Ala | Val | Cys | Glu | Pro | Ser | Val | Glu | Asp | Pro | Gly |
| | | 35 | | | | | 40 | | | | | 45 | | | |
| Arg | Ala | Ser | Cys | Val | Cys | Lys | Lys | Asn | Ala | Cys | Pro | Ala | Thr | Val | Ala |
| | 50 | | | | | 55 | | | | | 60 | | | | |
| Pro | Val | Cys | Gly | Ser | Asp | Ala | Ser | Thr | Tyr | Ser | Asn | Glu | Cys | Glu | Leu |
| 65 | | | | | 70 | | | | | 75 | | | | | 80 |
| Gln | Arg | Ala | Gln | Cys | Asn | Gln | Gln | Arg | Arg | Ile | Arg | Leu | Leu | Arg | Gln |
| | | | | 85 | | | | | 90 | | | | | 95 | |
| Gly | Pro | Cys | Gly | Ser | Arg | Asp | Pro | Cys | Ala | Asn | Val | Thr | Cys | Ser | Phe |
| | | | 100 | | | | | 105 | | | | | 110 | | |
| Gly | Ser | Thr | Cys | Val | Pro | Ser | Ala | Asp | Gly | Gln | Thr | Ala | Ser | Cys | Leu |
| | | 115 | | | | | 120 | | | | | 125 | | | |
| Cys | Pro | Thr | Thr | Cys | Phe | Gly | Ala | Pro | Asp | Gly | Thr | Val | Cys | Gly | Ser |
| | 130 | | | | | 135 | | | | | 140 | | | | |
| Asp | Gly | Val | Asp | Tyr | Pro | Ser | Glu | Cys | Gln | Leu | Leu | Ser | His | Ala | Cys |
| 145 | | | | | 150 | | | | | 155 | | | | | 160 |
| Ala | Ser | Gln | Glu | His | Ile | Phe | Lys | Lys | Phe | Asn | Gly | Pro | Cys | Asp | Pro |
| | | | | 165 | | | | | 170 | | | | | 175 | |
| Cys | Gln | Gly | Ser | Met | Ser | Asp | Leu | Asn | His | Ile | Cys | Arg | Val | Asn | Pro |
| | | | 180 | | | | | 185 | | | | | 190 | | |
| Arg | Thr | Arg | His | Pro | Glu | Met | Leu | Leu | Arg | Pro | Glu | Asn | Cys | Pro | Ala |
| | | 195 | | | | | 200 | | | | | 205 | | | |
| Gln | His | Thr | Pro | Ile | Cys | Gly | Asp | Asp | Gly | Val | Thr | Tyr | Glu | Asn | Asp |
| | 210 | | | | | 215 | | | | | 220 | | | | |
| Cys | Val | Met | Ser | Arg | Ile | Gly | Ala | Thr | Arg | Gly | Leu | Leu | Leu | Gln | Lys |
| 225 | | | | | 230 | | | | | 235 | | | | | 240 |
| Val | Arg | Ser | Gly | Gln | Cys | Gln | Thr | Arg | Asp | Gln | Cys | Pro | Glu | Thr | Cys |
| | | | | 245 | | | | | 250 | | | | | 255 | |
| Gln | Phe | Asn | Ser | Val | Cys | Leu | Ser | Arg | Arg | Gly | Arg | Pro | His | Cys | Ser |
| | | | 260 | | | | | 265 | | | | | 270 | | |
| Cys | Asp | Arg | Val | Thr | Cys | Asp | Gly | Ser | Tyr | Arg | Pro | Val | Cys | Ala | Gln |
| | | 275 | | | | | 280 | | | | | 285 | | | |
| Asp | Gly | His | Thr | Tyr | Asn | Asn | Asp | Cys | Trp | Arg | Gln | Gln | Ala | Glu | Cys |
| | 290 | | | | | 295 | | | | | 300 | | | | |
| Arg | Gln | Gln | Arg | Ala | Ile | Pro | Pro | Lys | His | Gln | Gly | Pro | Cys | Asp | Gln |
| 305 | | | | | 310 | | | | | 315 | | | | | 320 |

-continued

```
Thr Pro Ser Pro Cys His Gly Val Gln Cys Ala Phe Gly Ala Val Cys
            325                 330                 335
Thr Val Lys Asn Gly Lys Ala Glu Cys Glu Cys Gln Arg Val Cys Ser
            340                 345                 350
Gly Ile Tyr Asp Pro Val Cys Gly Ser Asp Gly Val Thr Tyr Gly Ser
            355                 360                 365
Val Cys Glu Leu Glu Ser Met Ala Cys Thr Leu Gly Arg Glu Ile Gln
            370                 375                 380
Val Ala Arg Arg Gly Pro Cys Asp Pro Cys Gly Gln Cys Arg Phe Gly
385                 390                 395                 400
Ser Leu Cys Glu Val Glu Thr Gly Arg Cys Val Cys Pro Ser Glu Cys
                    405                 410                 415
Val Glu Ser Ala Gln Pro Val Cys Gly Ser Asp Gly His Thr Tyr Ala
                    420                 425                 430
Ser Glu Cys Glu Leu His Val His Ala Cys Thr His Gln Ile Ser Leu
                    435                 440                 445
Tyr Val Ala Ser Ala Gly His Cys Gln Thr Cys Gly Glu Lys Val Cys
            450                 455                 460
Thr Phe Gly Ala Val Cys Ser Ala Gly Gln Cys Val Cys Pro Arg Cys
465                 470                 475                 480
Glu His Pro Pro Gly Pro Val Cys Gly Ser Asp Gly Val Thr Tyr
                    485                 490                 495
Leu Ser Ala Cys Glu Leu Arg Glu Ala Ala Cys Gln Gln Val Gln
                    500                 505                 510
Ile Glu Glu Ala His Ala Gly Pro Cys Glu Pro Ala Glu Cys Gly Ser
            515                 520                 525
Gly Gly Ser Gly Ser Gly Glu Asp Glu Cys Glu Gln Glu Leu Cys
            530                 535                 540
Arg Gln Arg Gly Gly Ile Trp Asp Glu Asp Ser Glu Asp Gly Pro Cys
545                 550                 555                 560
Val Cys Asp Phe Ser Cys Gln Ser Val Pro Arg Ser Pro Val Cys Gly
                    565                 570                 575
Ser Asp Gly Val Thr Tyr Gly Thr Glu Cys Asp Leu Lys Lys Ala Arg
                    580                 585                 590
Cys Glu Ser Gln Gln Glu Leu Tyr Val Ala Ala Gln Gly Ala Cys Arg
                    595                 600                 605
Gly Pro Thr Leu Ala Pro Leu Leu Pro Val Ala Phe Pro His Cys Ala
            610                 615                 620
Gln Thr Pro Tyr Gly Cys Cys Gln Asp Asn Phe Thr Ala Ala Gln Gly
625                 630                 635                 640
Val Gly Leu Ala Gly Cys Pro Ser Thr Cys His Cys Asn Pro His Gly
                    645                 650                 655
Ser Tyr Ser Gly Thr Cys Asp Pro Ala Thr Gly Gln Cys Ser Cys Arg
                    660                 665                 670
Pro Gly Val Gly Gly Leu Arg Cys Asp Arg Cys Glu Pro Gly Phe Trp
            675                 680                 685
Asn Phe Arg Gly Ile Val Thr Asp Gly His Ser Gly Cys Thr Pro Cys
            690                 695                 700
Ser Cys Asp Pro Arg Gly Ala Val Arg Asp Asp Cys Glu Gln Met Thr
705                 710                 715                 720
Gly Leu Cys Ser Cys Arg Pro Gly Val Ala Gly Pro Lys Cys Gly Gln
                    725                 730                 735
Cys Pro Asp Gly Gln Val Leu Gly His Leu Gly Cys Glu Ala Asp Pro
```

```
                740                 745                 750
Met Thr Pro Val Thr Cys Val Glu Ile His Cys Glu Phe Gly Ala Ser
            755                 760                 765
Cys Val Glu Lys Ala Gly Phe Ala Gln Cys Ile Cys Pro Thr Leu Thr
    770                 775                 780
Cys Pro Glu Ala Asn Ser Thr Lys Val Cys Gly Ser Asp Gly Val Thr
785                 790                 795                 800
Tyr Gly Asn Glu Cys Gln Leu Lys Ala Ile Ala Cys Arg Gln Arg Leu
                805                 810                 815
Asp Ile Ser Thr Gln Ser Leu Gly Pro Cys Gln Glu Ser Val Thr Pro
            820                 825                 830
Gly Ala Ser Pro Thr Ser Ala Ser Met Thr Thr Pro Arg His Ile Leu
            835                 840                 845
Ser Lys Thr Leu Pro Phe Pro His Asn Ser Leu Pro Leu Ser Pro Gly
        850                 855                 860
Ser Thr Thr His Asp Trp Pro Thr Pro Leu Pro Ile Ser Pro His Thr
865                 870                 875                 880
Thr Val Ser Ile Pro Arg Ser Thr Ala Trp Pro Val Leu Thr Val Pro
                885                 890                 895
Pro Thr Ala Ala Ala Ser Asp Val Thr Ser Leu Ala Thr Ser Ile Phe
            900                 905                 910
Ser Glu Ser Gly Ser Ala Asn Gly Ser Gly Asp Glu Glu Leu Ser Gly
        915                 920                 925
Asp Glu Glu Ala Ser Gly Gly Gly Ser Gly Gly Leu Glu Pro Pro Val
            930                 935                 940
Gly Ser Ile Val Val Thr His Gly Pro Pro Ile Glu Arg Ala Ser Cys
945                 950                 955                 960
Tyr Asn Ser Pro Leu Gly Cys Cys Ser Asp Gly Lys Thr Pro Ser Leu
                965                 970                 975
Asp Ser Glu Gly Ser Asn Cys Pro Ala Thr Lys Ala Phe Gln Gly Val
            980                 985                 990
Leu Glu Leu Glu Gly Val Glu Gly  Gln Glu Leu Phe Tyr  Thr Pro Glu
        995                 1000                1005
Met Ala  Asp Pro Lys Ser Glu  Leu Phe Gly Glu Thr  Ala Arg Ser
    1010                1015                1020
Ile Glu  Ser Thr Leu Asp Asp  Leu Phe Arg Asn Ser  Asp Val Lys
    1025                1030                1035
Lys Asp  Phe Trp Ser Val Arg  Leu Arg Glu Leu Gly  Pro Gly Lys
    1040                1045                1050
Leu Val  Arg Ala Ile Val Asp  Val His Phe Asp Pro  Thr Thr Ala
    1055                1060                1065
Phe Gln  Ala Ser Asp Val Gly  Gln Ala Leu Leu Arg  Gln Ile Gln
    1070                1075                1080
Val Ser  Arg Pro Trp Ala Leu  Ala Val Arg Arg Pro  Leu Gln Glu
    1085                1090                1095
His Val  Arg Phe Leu Asp Phe  Asp Trp Phe Pro Thr  Phe Phe Thr
    1100                1105                1110
Gly Ala  Ala Thr Gly Thr Thr  Ala Ala Met Ala Thr  Ala Arg Ala
    1115                1120                1125
Thr Thr  Val Ser Arg Leu Pro  Ala Ser Ser Val Thr  Pro Arg Val
    1130                1135                1140
Tyr Pro  Ser His Thr Ser Arg  Pro Val Gly Arg Thr  Thr Ala Pro
    1145                1150                1155
```

```
Pro Thr Thr Arg Arg Pro Pro Thr Thr Ala Thr Asn Met Asp Arg
    1160                1165                1170

Pro Arg Thr Pro Gly His Gln Gln Pro Ser Lys Ser Cys Asp Ser
    1175                1180                1185

Gln Pro Cys Leu His Gly Gly Thr Cys Gln Asp Gln Asp Ser Gly
    1190                1195                1200

Lys Gly Phe Thr Cys Ser Cys Thr Ala Gly Arg Gly Gly Ser Val
    1205                1210                1215

Cys Glu Lys Val Gln Pro Pro Ser Met Pro Ala Phe Lys Gly His
    1220                1225                1230

Ser Phe Leu Ala Phe Pro Thr Leu Arg Ala Tyr His Thr Leu Arg
    1235                1240                1245

Leu Ala Leu Glu Phe Arg Ala Leu Glu Thr Glu Gly Leu Leu Leu
    1250                1255                1260

Tyr Asn Gly Asn Ala Arg Gly Lys Asp Phe Leu Ala Leu Ala Leu
    1265                1270                1275

Leu Asp Gly Arg Val Gln Phe Arg Phe Asp Thr Gly Ser Gly Pro
    1280                1285                1290

Ala Val Leu Thr Ser Leu Val Pro Val Glu Pro Gly Arg Trp His
    1295                1300                1305

Arg Leu Glu Leu Ser Arg His Trp Arg Gln Gly Thr Leu Ser Val
    1310                1315                1320

Asp Gly Glu Thr Pro Val Val Gly Glu Ser Pro Ser Gly Thr Asp
    1325                1330                1335

Gly Leu Asn Leu Asp Thr Asn Leu Tyr Val Gly Gly Ile Pro Glu
    1340                1345                1350

Glu Gln Val Ala Met Val Leu Asp Arg Thr Ser Val Gly Val Gly
    1355                1360                1365

Leu Lys Gly Cys Ile Arg Met Leu Asp Ile Asn Asn Gln Gln Leu
    1370                1375                1380

Glu Leu Ser Asp Trp Gln Arg Ala Ala Val Gln Ser Ser Gly Val
    1385                1390                1395

Gly Glu Cys Gly Asp His Pro Cys Leu Pro Asn Pro Cys His Gly
    1400                1405                1410

Gly Ala Leu Cys Gln Ala Leu Glu Ala Gly Met Phe Leu Cys Gln
    1415                1420                1425

Cys Pro Pro Gly Arg Phe Gly Pro Thr Cys Ala Asp Glu Lys Ser
    1430                1435                1440

Pro Cys Gln Pro Asn Pro Cys His Gly Ala Ala Pro Cys Arg Val
    1445                1450                1455

Leu Ser Ser Gly Gly Ala Lys Cys Glu Cys Pro Leu Gly Arg Ser
    1460                1465                1470

Gly Thr Phe Cys Gln Thr Val Leu Glu Thr Ala Gly Ser Arg Pro
    1475                1480                1485

Phe Leu Ala Asp Phe Asn Gly Phe Ser Tyr Leu Glu Leu Lys Gly
    1490                1495                1500

Leu His Thr Phe Glu Arg Asp Leu Gly Glu Lys Met Ala Leu Glu
    1505                1510                1515

Met Val Phe Leu Ala Arg Gly Pro Ser Gly Leu Leu Leu Tyr Asn
    1520                1525                1530

Gly Gln Lys Thr Asp Gly Lys Gly Asp Phe Val Ser Leu Ala Leu
    1535                1540                1545
```

-continued

```
His Asn Arg His Leu Glu Phe Cys Tyr Asp Leu Gly Lys Gly Ala
1550                1555                1560

Ala Val Ile Arg Ser Lys Glu Pro Ile Ala Leu Gly Thr Trp Val
1565                1570                1575

Arg Val Phe Leu Glu Arg Asn Gly Arg Lys Gly Ala Leu Gln Val
1580                1585                1590

Gly Asp Gly Pro Arg Val Leu Gly Glu Ser Pro Lys Ser Arg Lys
1595                1600                1605

Val Pro His Thr Met Leu Asn Leu Lys Glu Pro Leu Tyr Ile Gly
1610                1615                1620

Gly Ala Pro Asp Phe Ser Lys Leu Ala Arg Gly Ala Ala Val Ser
1625                1630                1635

Ser Gly Phe Ser Gly Val Ile Gln Leu Val Ser Leu Arg Gly His
1640                1645                1650

Gln Leu Leu Thr Gln Glu His Val Leu Arg Ala Val Asp Val Ser
1655                1660                1665

Pro Phe Ala Asp His Pro Cys Thr Gln Ala Leu Gly Asn Pro Cys
1670                1675                1680

Leu Asn Gly Gly Ser Cys Val Pro Arg Glu Ala Thr Tyr Glu Cys
1685                1690                1695

Leu Cys Pro Gly Gly Phe Ser Gly Leu His Cys Glu Gln Gly Leu
1700                1705                1710

Val Gly Ser Met Val Ser Lys Gly Glu Glu Leu Phe Thr Gly Val
1715                1720                1725

Val Pro Ile Leu Val Glu Leu Asp Gly Asp Val Asn Gly His Lys
1730                1735                1740

Phe Ser Val Ser Gly Glu Gly Glu Gly Asp Ala Thr Tyr Gly Lys
1745                1750                1755

Leu Thr Leu Lys Phe Ile Cys Thr Thr Gly Lys Leu Pro Val Pro
1760                1765                1770

Trp Pro Thr Leu Val Thr Thr Leu Thr Tyr Gly Val Gln Cys Phe
1775                1780                1785

Ser Arg Tyr Pro Asp His Met Lys Gln His Asp Phe Phe Lys Ser
1790                1795                1800

Ala Met Pro Glu Gly Tyr Val Gln Glu Arg Thr Ile Phe Phe Lys
1805                1810                1815

Asp Asp Gly Asn Tyr Lys Thr Arg Ala Glu Val Lys Phe Glu Gly
1820                1825                1830

Asp Thr Leu Val Asn Arg Ile Glu Leu Lys Gly Ile Asp Phe Lys
1835                1840                1845

Glu Asp Gly Asn Ile Leu Gly His Lys Leu Glu Tyr Asn Tyr Asn
1850                1855                1860

Ser His Asn Val Tyr Ile Met Ala Asp Lys Gln Lys Asn Gly Ile
1865                1870                1875

Lys Val Asn Phe Lys Ile Arg His Asn Ile Glu Asp Gly Ser Val
1880                1885                1890

Gln Leu Ala Asp His Tyr Gln Gln Asn Thr Pro Ile Gly Asp Gly
1895                1900                1905

Pro Val Leu Leu Pro Asp Asn His Tyr Leu Ser Thr Gln Ser Ala
1910                1915                1920

Leu Ser Lys Asp Pro Asn Glu Lys Arg Asp His Met Val Leu Leu
1925                1930                1935

Glu Phe Val Thr Ala Ala Gly Ile Thr Leu Gly Met Asp Glu Leu
```

```
                    1940                  1945                  1950
Tyr Lys Ser Gly Leu Arg Ser Arg Ala Gln Ala Ser Asn Ser Ala
        1955                  1960                  1965

Val Asp Gly Thr Ala Gly Pro Gly Ser Thr Gly Ser Arg
        1970                  1975                  1980

<210> SEQ ID NO 10
<211> LENGTH: 68
<212> TYPE: DNA
<213> ORGANISM: Artificial sequence
<220> FEATURE:
<223> OTHER INFORMATION: Synthetic construct; primer introducing HpaI
      site

<400> SEQUENCE: 10
gcgagttaac caccatcacc atcaccatca ccatggaagc ctggctgact ttaatggctt    60
ctcctacc                                                             68

<210> SEQ ID NO 11
<211> LENGTH: 78
<212> TYPE: DNA
<213> ORGANISM: Artificial sequence
<220> FEATURE:
<223> OTHER INFORMATION: Synthetic construct; primer introducing NotI
      site

<400> SEQUENCE: 11
acctgcggcc gctcattttt cgaactgcgg gtggctccag ccagagccag agccgggagt    60
ggggcagggt cttagctc                                                  78

<210> SEQ ID NO 12
<211> LENGTH: 436
<212> TYPE: PRT
<213> ORGANISM: Artificial sequence
<220> FEATURE:
<223> OTHER INFORMATION: Agrin C-45 fragment containing 8 x His

<400> SEQUENCE: 12

Ala Arg Val Asn His His His His His His His His Gly Ser Leu Ala
1               5                   10                  15

Asp Phe Asn Gly Phe Ser Tyr Leu Glu Leu Lys Gly Leu His Thr Phe
            20                  25                  30

Glu Arg Asp Leu Gly Glu Lys Met Ala Leu Glu Met Val Phe Leu Ala
        35                  40                  45

Arg Gly Pro Ser Gly Leu Leu Leu Tyr Asn Gly Gln Lys Thr Asp Gly
    50                  55                  60

Lys Gly Asp Phe Val Ser Leu Ala Leu His Asn Arg His Leu Glu Phe
65                  70                  75                  80

Cys Tyr Asp Leu Gly Lys Gly Ala Ala Val Ile Arg Ser Lys Glu Pro
                85                  90                  95

Ile Ala Leu Gly Thr Trp Val Arg Val Phe Leu Glu Arg Asn Gly Arg
            100                 105                 110

Lys Gly Ala Leu Gln Val Gly Asp Gly Pro Arg Val Leu Gly Glu Ser
        115                 120                 125

Pro Val Pro His Thr Met Leu Asn Leu Lys Glu Pro Leu Tyr Ile Gly
    130                 135                 140

Gly Ala Pro Asp Phe Ser Lys Leu Ala Arg Gly Ala Ala Val Ser Ser
145                 150                 155                 160

Gly Phe Ser Gly Val Ile Gln Leu Val Ser Leu Arg Gly His Gln Leu
```

```
                    165                 170                 175

Leu Thr Gln Glu His Val Leu Arg Ala Val Asp Val Ser Pro Phe Ala
            180                 185                 190

Asp His Pro Cys Thr Gln Ala Leu Gly Asn Pro Cys Leu Asn Gly Gly
            195                 200                 205

Ser Cys Val Pro Arg Glu Ala Thr Tyr Glu Cys Leu Cys Pro Gly Gly
    210                 215                 220

Phe Ser Gly Leu His Cys Glu Lys Gly Leu Val Glu Lys Ser Val Gly
225                 230                 235                 240

Asp Leu Glu Thr Leu Ala Phe Asp Gly Arg Thr Tyr Ile Glu Tyr Leu
                245                 250                 255

Asn Ala Val Ile Glu Ser Glu Lys Ala Leu Gln Ser Asn His Phe Glu
            260                 265                 270

Leu Ser Leu Arg Thr Glu Ala Thr Gln Gly Leu Val Leu Trp Ile Gly
            275                 280                 285

Lys Ala Ala Glu Arg Ala Asp Tyr Met Ala Leu Ala Ile Val Asp Gly
            290                 295                 300

His Leu Gln Leu Ser Tyr Asp Leu Gly Ser Gln Pro Val Val Leu Arg
305                 310                 315                 320

Ser Thr Val Lys Val Asn Thr Asn Arg Trp Leu Arg Ile Arg Ala His
                325                 330                 335

Arg Glu His Arg Glu Gly Ser Leu Gln Val Gly Asn Glu Ala Pro Val
            340                 345                 350

Thr Gly Ser Ser Pro Leu Gly Ala Thr Gln Leu Asp Thr Asp Gly Ala
            355                 360                 365

Leu Trp Leu Gly Gly Leu Gln Lys Leu Pro Val Gly Gln Ala Leu Pro
    370                 375                 380

Lys Ala Tyr Gly Thr Gly Phe Val Gly Cys Leu Arg Asp Val Val Val
385                 390                 395                 400

Gly His Arg Gln Leu His Leu Leu Glu Asp Ala Val Thr Lys Pro Glu
                405                 410                 415

Leu Arg Pro Cys Pro Thr Pro Gly Ser Gly Ser Gly Trp Ser His Pro
            420                 425                 430

Gln Phe Glu Lys
            435

<210> SEQ ID NO 13
<211> LENGTH: 8
<212> TYPE: PRT
<213> ORGANISM: Artificial Sequence
<220> FEATURE:
<223> OTHER INFORMATION: Synthetic construct

<400> SEQUENCE: 13

Pro Ile Glu Arg Ala Ser Cys Tyr
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa can be Pro or Ala
<220> FEATURE:
<221> NAME/KEY: MISC_FEATURE
```

```
<222> LOCATION: (3)..(3)
<223> OTHER INFORMATION: Xaa can be Ile or Val
<220> FEATURE:
<221> NAME/KEY: MISC_FEATURE
<222> LOCATION: (7)..(7)
<223> OTHER INFORMATION: Xaa can be Ser or Thr

<400> SEQUENCE: 14

Pro Xaa Xaa Glu Arg Ala Xaa Cys Tyr
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa can be Gly or Ala
<220> FEATURE:
<221> NAME/KEY: MISC_FEATURE
<222> LOCATION: (2)..(2)
<223> OTHER INFORMATION: Xaa can be Leu or Ile or Thre
<220> FEATURE:
<221> NAME/KEY: MISC_FEATURE
<222> LOCATION: (3)..(3)
<223> OTHER INFORMATION: Xaa can be Ile or Val
<220> FEATURE:
<221> NAME/KEY: MISC_FEATURE
<222> LOCATION: (7)..(7)
<223> OTHER INFORMATION: Xaa can be Val or Ala

<400> SEQUENCE: 15

Xaa Xaa Xaa Glu Lys Ser Xaa Gly
1               5

<210> SEQ ID NO 16
<211> LENGTH: 16
<212> TYPE: PRT
<213> ORGANISM: Artificial Sequence
<220> FEATURE:
<223> OTHER INFORMATION: Synthetic construct

<400> SEQUENCE: 16

Gly Ala Gly Ser Pro Ile Glu Arg Ala Ser Cys Tyr Gly Ser Ser Thr
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa stands for a cysteine residue
<220> FEATURE:
<221> NAME/KEY: MISC_FEATURE
<222> LOCATION: (10)..(10)
<223> OTHER INFORMATION: Xaa stands for a cysteine residue
<220> FEATURE:
<221> NAME/KEY: MISC_FEATURE
<222> LOCATION: (11)..(11)
<223> OTHER INFORMATION: Xaa stands for a cysteine residue

<400> SEQUENCE: 17

Ala Ser Xaa Tyr Asn Ser Pro Leu Gly Xaa Xaa Ser Gly Asp Lys
1               5                   10                  15
```

```
<210> SEQ ID NO 18
<211> LENGTH: 24
<212> TYPE: PRT
<213> ORGANISM: Artificial Sequence
<220> FEATURE:
<223> OTHER INFORMATION: Synthetic construct

<400> SEQUENCE: 18

Val Val Thr His Gly Pro Pro Ile Glu Arg Ala Ser Cys Tyr Asn Ser
1               5                   10                  15

Pro Leu Gly Cys Cys Ser Asp Lys
            20

<210> SEQ ID NO 19
<211> LENGTH: 9
<212> TYPE: PRT
<213> ORGANISM: Homo sapiens

<400> SEQUENCE: 19

Pro Pro Val Glu Arg Ala Ser Cys Tyr
1               5

<210> SEQ ID NO 20
<211> LENGTH: 9
<212> TYPE: PRT
<213> ORGANISM: Rattus norvegicus

<400> SEQUENCE: 20

Pro Pro Ile Glu Arg Ala Ser Cys Tyr
1               5

<210> SEQ ID NO 21
<211> LENGTH: 9
<212> TYPE: PRT
<213> ORGANISM: Mus musculus

<400> SEQUENCE: 21

Pro Pro Ile Glu Arg Ala Ser Cys Tyr
1               5

<210> SEQ ID NO 22
<211> LENGTH: 9
<212> TYPE: PRT
<213> ORGANISM: Gallus gallus

<400> SEQUENCE: 22

Pro Ala Ile Glu Arg Ala Thr Cys Tyr
1               5

<210> SEQ ID NO 23
<211> LENGTH: 10
<212> TYPE: PRT
<213> ORGANISM: Artificial Sequence
<220> FEATURE:
<223> OTHER INFORMATION: Synthetic construct

<400> SEQUENCE: 23

Ser Val Gly Asp Leu Glu Thr Leu Ala Phe
1               5                   10

<210> SEQ ID NO 24
<211> LENGTH: 19
<212> TYPE: PRT
<213> ORGANISM: Artificial Sequence
<220> FEATURE:
```

```
<223> OTHER INFORMATION: Synthetic construct

<400> SEQUENCE: 24

Gly Leu Val Glu Lys Ser Val Gly Asp Leu Glu Thr Leu Ala Phe Asp
1               5                   10                  15

Gly Arg Thr

<210> SEQ ID NO 25
<211> LENGTH: 8
<212> TYPE: PRT
<213> ORGANISM: Homo sapiens

<400> SEQUENCE: 25

Gly Leu Val Glu Lys Ser Ala Gly
1               5

<210> SEQ ID NO 26
<211> LENGTH: 8
<212> TYPE: PRT
<213> ORGANISM: Rattus norvegicus

<400> SEQUENCE: 26

Gly Leu Val Glu Lys Ser Val Gly
1               5

<210> SEQ ID NO 27
<211> LENGTH: 8
<212> TYPE: PRT
<213> ORGANISM: Mus musculus

<400> SEQUENCE: 27

Gly Ile Val Glu Lys Ser Val Gly
1               5

<210> SEQ ID NO 28
<211> LENGTH: 8
<212> TYPE: PRT
<213> ORGANISM: Gallus gallus

<400> SEQUENCE: 28

Ala Thr Ile Glu Lys Ser Ala Gly
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa can be Gly or Ala
<220> FEATURE:
<221> NAME/KEY: MISC_FEATURE
<222> LOCATION: (2)..(2)
<223> OTHER INFORMATION: Xaa can be Leu or Ile or Thr
<220> FEATURE:
<221> NAME/KEY: MISC_FEATURE
<222> LOCATION: (3)..(3)
<223> OTHER INFORMATION: Xaa can be Val or Ile
<220> FEATURE:
<221> NAME/KEY: MISC_FEATURE
<222> LOCATION: (7)..(7)
<223> OTHER INFORMATION: Xaa can be Val or Ala

<400> SEQUENCE: 29
```

```
Xaa Xaa Xaa Glu Lys Ser Xaa Gly
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic construct

<400> SEQUENCE: 30

Leu Val Glu Lys Ser Val Gly Asp
1               5
```